(12) United States Patent
Baucke et al.

(10) Patent No.: US 7,144,902 B1
(45) Date of Patent: Dec. 5, 2006

(54) PRODRUGS OF THROMBIN INHIBITORS

(75) Inventors: Dorit Baucke, Mannheim (DE);
Helmut Mack, Ludwigshafen (DE);
Werner Seitz, Plankstadt (DE);
Wilfried Hornberger, Neustadt (DE);
Gisela Backfisch, Dossenheim (DE);
Juergen Delzer, Speyer (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/958,349

(22) PCT Filed: Apr. 5, 2000

(86) PCT No.: PCT/EP00/03009

§ 371 (c)(1),
(2), (4) Date: Mar. 28, 2002

(87) PCT Pub. No.: WO00/61609

PCT Pub. Date: Oct. 19, 2000

(30) Foreign Application Priority Data

| Apr. 9, 1999 | (DE) | ................................. 199 15 930 |
| Jul. 23, 1999 | (DE) | ................................. 199 34 123 |
| Oct. 6, 1999 | (DE) | ................................. 199 47 920 |

(51) Int. Cl.
*A61K 31/425* (2006.01)
*C07D 277/20* (2006.01)

(52) U.S. Cl. ...................... 514/365; 514/422; 514/444; 514/461; 548/202; 548/517; 548/527; 548/950

(58) Field of Classification Search ................ 548/204, 548/202, 517, 527, 950; 514/365, 422, 444, 514/461
See application file for complete search history.

(56) References Cited

U.S. PATENT DOCUMENTS

| 6,114,358 | A | 9/2000 | Baucke et al. ............... 514/336 |
| 6,492,402 | B1 * | 12/2002 | Lee et al. .................... 514/365 |
| 6,683,055 | B1 * | 1/2004 | Hillen et al. ................... 514/19 |
| 6,740,647 | B1 * | 5/2004 | Baucke et al. ......... 514/210.18 |

FOREIGN PATENT DOCUMENTS

| DE | 196 32 773 | 2/1998 |
| EP | 0 672 658 | 9/1995 |
| WO | WO 95/23609 | 9/1995 |
| WO | WO 97/31939 | 2/1997 |
| WO | WO 97/23499 | 7/1997 |
| WO | WO 99/37611 | 7/1999 |
| WO | WO 99/37668 | 7/1999 |

* cited by examiner

*Primary Examiner*—Joseph K. McKane
*Assistant Examiner*—Robert Shiao
(74) *Attorney, Agent, or Firm*—Wood, Phillips, Katz, Clark & Mortimer

(57) ABSTRACT

The present invention relates to prodrugs of pharmacologically active five-membered heterocyclic amidines from which are produced in vivo compounds which are competitive inhibitors of trypsin-like serine proteases, in particular thrombin and kininogenases such as kallikrein, to the preparation thereof and to the use thereof as medicines. The invention also relates to pharmaceutical compositions which comprise the prodrugs of the active compounds as ingredients, and to the use of the compounds as thrombin inhibitors, anticoagulants and as antiinflammatory agents.

4 Claims, No Drawings

PRODRUGS OF THROMBIN INHIBITORS

The present invention relates to prodrugs of pharmacologically active five-membered heterocyclic amidines from which are produced in vivo compounds which are competitive inhibitors of trypsin-like serine proteases, in particular thrombin, and kininogenases such as kailikeins to the preparation thereof and to the use thereof as medicines. The invention also relates to pharmaceutical compositions which comprise the prodrugs of the active compounds as ingredients, and to the use of the compounds as thrombin inhibitors, anticoagulants and as antiinflammatory agents.

Thrombin belongs to the group of serine proteases and plays a central part in the blood coagulation cascade as terminal enzyme. Both the intrinsic and the extrinsic coagulation cascade lead via a plurality of amplifying stages to the production of thrombin from prothrombin. Thrombin-catalyzed cleavage of fibrinogen to fibrin then initiates blood coagulation and aggregation of platelets which, in turn, due to the binding of platelet factor 3 and coagulation factor XIII, and a large number of highly active mediators, enhance thrombin formation.

The formation and action of thrombin are central events in the development of white, arterial, and of red, venous, thrombi and are therefore potentially effective points of attack for drugs. Thrombin inhibitors are, by contrast with heparin, able independently of cofactors completely to inhibit simultaneously the effects of free thrombin and of that bound to platelets. They are able to prevent in the acute phase thromboembolic events after percutaneous transluminal coronary angioplasty (PTCA) and lysis, and to act as anticoagulants in an extracorporeal circulation (heart-lung machine, hemodialysis). They can also be used generally for the prophylaxis of thrombosis, for example after surgical operations.

It is known that synthetic arginine derivatives influence the enzymatic activity of thrombin by interacting with the active serine residue of the protease thrombin. Peptides based on Phe-Pro-Arg in which the N-terminal amino acid is in the D form have proven particularly beneficial. D-Phe-Pro-Arg-isopropyl ester is described as a competitive thrombin inhibitor (C. Mattson et al., Folia Haematol, 109, 43–51, 1983). WO 94/29336, EP 0 601 459 and WO 95/23609 and WO 95/35309 represent a further development in which the agmatine residue is replaced by an arylamidine residue.

EP 0 672 658 describes not only thrombin inhibitors having an agmatine or benzamidine residue but also a thrombin inhibitor with an amidinothiophene (Example 65).

WO 98/06741 describes thrombin inhibitors with five-membered heterocyclic amidines.

Although these compounds have a significant antithrombotic action, an improvement in their pharmacokinetic properties after oral or parenteral administration is advantageous. It is desirable inter alia to influence the following pharmacokinetic properties:

I. Improving the absorption from the gastrointestinal tract, aiming at high bioavailability.
II. Minimizing the inter- and intraindividual variability of the bioavailability through a constant absorption basis.
III. Achieving therapeutically relevant active levels which are as constant as possible over the time course. In relation to the therapeutic index, plasma concentrations which are as constant as possible over the time course are indispensable, because excessive fluctuations may lead to unwanted side effects. If the plasma concentration of the active substance is too high, hemorrhages may be expected, and if the concentration is too low there is an increased risk of thrombus formation.
IV. Prolonging the duration of action of the active substance: Active substance means the pharmacologically active substance (drug) in contrast to the substance (prodrug) which must first be converted metabolically into the active substance.

A further advantage of prodrugs over drugs is that there are no high local concentrations of the drugs outside the target area. Moreover, when using less selective drugs, the side effects are minimised, since e.g. in the gastrointestinal tract no further serine proteases are inhibited when the drug is essentially only produced after or during the gastrointestinal passage by metabolising the prodrug.

The aim of this invention is to improve the pharmacokinetic properties of the thrombin inhibitors mentioned in particular in WO 98/6741 through suitable prodrugs.

The invention relates to compounds of the formula I

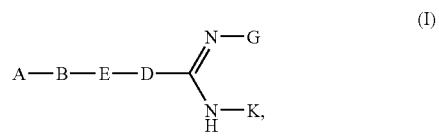

in which A, B, D, E, G and K have the following meanings:

A: $R^1OOC-CH_2-$, $R^1OOC-CH_2-CH_2-$, $R^1OOC-CH(CH_3)-$, $R^1OOC-C(CH_3)_2-R^1OOC-CH(C_2H_5)-$, $C_{1-4}$-alkyl-$SO_2-(CH_2)_{2-6}-$, $HO_3S-(CH_2)_{2-6}-$, 5-te-trazolyl-$(CH_2)_{1-6}-$, $C_{1-4}$-alkyl-$O-(CH_2)_{2-6}-$, $R^2R^3N-(CH_2)_{2-6}-$, $R^2S(CH_2)_{2-6}-$, $R^2R^3NSO_2-(CH_2)_{2-6}-$, $HO-(CH_2)_{2-6}-$, $R^{1a}S(O)C-CH_2-$, $R^{1a}O(S)C-CH_2-$, $R^2R^3N(O)C-CH_2-$, $R^2R^3N-O-CO-CH_2-$, $R^2N(OH)-CO-CH_2-$, where $R^2$ and $R^3$ are, independently of one another, H, $C_1-C_6$-alkyl, $C_3-C_8$-cycloalkyl or $C_{3-8}$-cycloalkyl-$C_{1-3}$-alkyl- or $R^2$ and $R^3$ form together a $C_{4-6}$-alkylene chain, in which $R^1$: is H—, $C_1-C_6$-alkyl, $H_3C-[O-CH_2-CH_2]_q$ (q=1–4), $C_7-C_{12}$-bicycloalkyl, $C_{10}$-tricycloalkyl, $C_3-C_8$-cycloalkyl, $C_{3-8}$-cycloalkyl-$C_{1-3}$-alkyl-, pyranyl-, piperidinyl-, aryl- or phenyl-$C_1-C_4$-alkyl-, it being possible for all the radicals mentioned apart from H to carry optionally up to four identical or different radicals selected from $C_1-C_4$-alkyl, $CF_3$, F, Cl, $NO_2$, HO or $C_1-C_4$-alkoxy radicals, or $R^1$ is 2-oxo-1,3-dioxol-4-ylmethyl which may be substituted in position 5 by $C_1-C_{16}$-alkyl or aryl, $R^{1a}$: is H—, $C_1-C_{16}$-alkyl, $H_3C-[O-CH_2-CH_2]_q$ (q=1–4), $C_7-C_{12}$-bicycloalkyl, $C_{10}$-tricycloalkyl, $C_3-C_8$-cycloalkyl, $C_3-C_8$-cycloalkyl-$C_1-C_3$-alkyl, aryl- or phenyl-$C_1-C_3$-alkyl, it being possible for all the radicals mentioned apart from H to carry optionally up to three identical or different radicals selected from $C_1-C_4$-alkyl, $CF_3$, F, Cl, $NO_2$, HO or $C_1-C_4$-alkoxy radicals, or $R^1$: $R^{1b}-C(O)O-C(R^{1c})_2-$, $R^{1b}-(CO)NR^2-C(R^{1c})_2-$, where $R^{1b}$ can be $C_1-C_4$-alkyl, $C_3-C_8$-cycloalkyl-$C_1-C_3$-alkyl, $C_3-C_8$-cycloalkyl, $C_1-C_4$-alkyloxy, $C_3-C_8$-cycloalkyl-$C_1-C_3$-alkyloxy, $C_3-C_8$-cycloalkoxy, aryl or phenyl-$C_1-C_6$-alkyl, the two $R^{1c}$ radicals are, independently of one another, H, $CH_3$ or $C_2H_5$, and $R^2$ has the same meaning as above, or $R^2OOC-C_1-C_6$-alkyl, $R^2R^3N(O)C-C_1-C_6$-alkyl, $R^2R^3N-C_2-C_6$-alkyl, and in which $R^2$ and $R^3$ have the same meanings as above or, if $R^1$ is $R^2R^3N(O)C$—$C_1$–$C_6$-alkyl, $R^2$ and $R^3$ together form a $C_4$–$C_6$-alkyl chain,

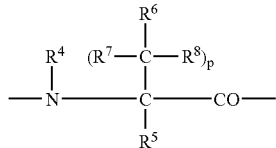

in which p is 0, 1, $R^4$: is H—, $R^9OOC$— with $R^9=C_{1-16}$-alkyl, $C_{3-8}$-cycloalkyl-, phenyl-, phenyl-$C_{1-4}$-alkyl-, $R^{10}C(O)$—O—$CH_2$—, $R^{10}C(O)$—O—$CH(CH_3)$—, where $R^{10}$ can be $C_1$–$C_4$-alkyl, phenyl, benzyl, $C_3$–$C_8$-cycloalkyl or cyclohexyl-$CH_2$—, $R^5$ is H—, $R^6$ is H—, $C_{1-8}$-alkyl, $C_7$–$C_{12}$-bicycloalkyl or $C_{10}$-tricycloalkyl, phenyl which may carry up to three identical or different radicals from the group of $C_{1-4}$-alkyl, $CF_3$—, $C_{1-4}$-alkoxy, F— or Cl—, or $C_{3-8}$-cycloalkyl which may carry up to four identical or different $C_{1-4}$-alkyl radicals, or where one or two C—C single bonds in the ring can be replaced by a C=C double bond, or a phenyl ring can be fused on, $R^7$ is H—, $C_{1-8}$-alkyl, phenyl which may carry up to three identical or different radicals from the group of $C_{1-4}$-alkyl, $CF_3$—, $C_{1-4}$-alkoxy, F— or Cl—, or $C_{3-8}$-cycloalkyl which may carry up to four identical or different $C_{1-4}$-alkyl radicals, $R^8$ is H—, $CH_3$—,

E

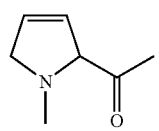 (II)

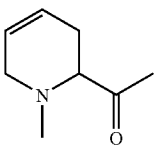 (III)

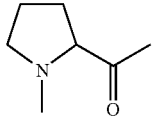 (IV)

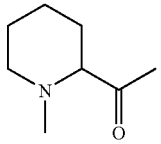 (V)

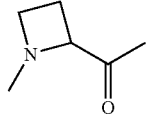 (VI)

D

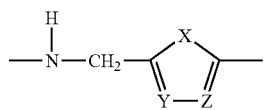 (VII)

with
X=S, O
Y=CH, C—$CH_3$, C—Cl, C—$CF_3$ and
Z=CH, C—$CH_3$, C—Cl, C—$CF_3$
or X=S, O Y=N Z=CH, C—$CH_3$, C—$CF_3$
or X=S, O Y=CH, C—$CH_3$, C—$CF_3$ Z=N,

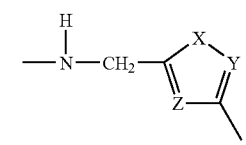 (VIII)

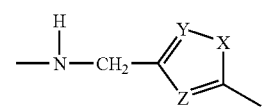 (IX)

with
X=S, O
Y=CH, C—$CH_3$ and C—$CF_3$
Z=CH, C—$CH_3$, C—Cl and C—$CF_3$
or X=O Y=N Z=CH, C—$CH_3$, C—$CF_3$
or X=O, S Y=CH, C—$CH_3$, C—$CF_3$ Z=N G: —H, —OH, —$OR^{18}$, —$OC(O)R^{19}$, —$C(O)OR^{20}$, —$SR^{18}$, —$C(S)SR^{20}$, in which $R^{18}$: is —$C_{1-8}$-alkyl, —$C_1$–$C_3$-alkyl-$C_3$–$C_8$-cycloalkyl, -aryl or —$C_1$–$C_6$-alkylphenyl, each of which may carry optionally up to three $C_1$–$C_4$-alkyl, $CF_3$, F, Cl, $NO_2$ or $C_1$–$C_4$-alkoxy radicals $R^{19}$: is —$C_{1-3}$-alkyl, -phenyl, $R^{20}$: is —$C_{1-8}$-alkyl, —$CH_2CCl_3$, —$C_1$–$C_3$-alkyl-$C_3$–$C_8$-cycloalkyl, —$C_3$–$C_8$-cycloalkyl, -phenyl or $C_1$–$C_3$-alkylphenyl, each of which may carry optionally up to three identical or different radicals selected from the group of $C_1$–$C_4$-alkyl, $CF_3$, F, Cl, $NO_2$ or $C_1$–$C_4$-alkoxy radicals, or $CH_2O$—$C(O)R^{10a}$, —$CH(CH_3)O$—$C(O)R^{10a}$, where $R^{10a}$ can be $C_1$–$C_{10}$-alkyl, -phenyl, benzyl, —$C_3$–$C_8$-cycloalkyl or —$CH_2$-cyclohexyl, or —$C(R^{10b})_2$—$CH_2$—O—$(O)C$—$R^{10c}$, where the two $R^{10b}$ radicals can be, independently of one another, H, $CH_3$ or ethyl, and $R^{10c}$ is —$C_1$–$C_3$-alkyl-$C_3$–$C_8$-cycloalkyl, —$C_3$–$C_8$-cycloalkyl or —$C_1$–$C_4$-alkyl,

K: H, or G and K together form a —C(O)O—, —C(O)S—, C(S)S— or —C(S)O— group, the configurational isomers thereof and the salts thereof with physiologically tolerated acids, where the following applies, with retention of the meanings of D:

(i)

when E is II or III, and G and K are H, then A and B have the following meanings:

A: $R^1OOC-CH_2-$, $R^1OOC-CH_2-CH_2-$, $R^1OOC-CH(CH_3)-$, $R^1OOC-CH(C_2H_5)-$, $R^1OOC-C(CH_3)_2-$, $R^{1a}S(O)C-CH_2-$, $R^{1a}O(S)C-CH_2-$, $R^2R^3N(O)C-CH_2-$, $R^2R^3N-CO-CH_2-$, $R^2N(OH)-CO-CH_2-$, $C_{1-4}$-alkyl-$SO_2-(CH_2)_{2-6}-$, $HO_3S-(CH_2)_{2-6}-$, 5-tetrazoylyl-$(CH_2)_{1-6}-$, $C_{1-4}$-alkyl-$O-(C_2)_{2-6}-$, $R^2R^3N-(CH_2)_{2-6}-$, $R^2S(CH_2)_{2-6}-$, $R^2R^3NSO_2-(CH_2)_{2-6}-$, where $R^2$ and $R^3$ are, independently of one another, H or $C_1-C_6$-alkyl, or $C_{3-8}$-cycloalkyl, or $R^2$ and $R^3$ form together a $C_{4-6}$-alkyl chain, in which $R^1$: is $C_7-C_{16}$-alkyl-, $H_3C-[O-CH_2-CH_2]_q$ (q=1-4), $C_7-C_{12}$-bicycloalkyl-, $C_{10}$-tricycloalkyl-, $C_3-C_8$-cycloalkyl-, $C_3-C_8$-cycloalkyl-$C_1-C_3$-alkyl-, pyranyl-, piperidinyl-, it being possible for all the radicals mentioned to carry optionally up to four $C_1-C_4$-alkyl, $CF_3$, F, Cl, $NO_2$, HO or $C_1-C_4$-alkoxy radicals, or $R^1$ is 2-oxo-1,3-dioxol-2-ylmethyl which may be substituted in position 5 by $C_1-C_{16}$-alkyl or aryl, $R^{1a}$: is H—, $C_1-C_{16}$-alkyl, $H_3C-[O-CH_2-CH_2]_q$ (q=1-4), $C_3-C_8$-cycloalkyl, $C_3-C_8$-cycloalkyl-$C_1-C_3$-alkyl, aryl or phenyl-$C_1-C_3$-alkyl, it being possible for all the radicals mentioned apart from H to carry optionally up to three $C_1-C_4$-alkyl, $CF_3$, F, Cl, $NO_2$, HO or $C_1-C_4$-alkoxy radicals, or $R^1$: is $R^{1b}-C(O)O-C(R^{1c})_2-$, $R^{1b}-C(O)NR^2-C(R^{1c})_2-$, where $R^{1b}$ can be $C_1-C_4$-alkyl, $C_3-C_8$-cycloalkyl-$C_1-C_3$-alkyl, $C_3-C_8$-cycloalkyl, $C_1-C_4$-alkyloxy, $C_3-C_8$-cycloalkyl-$C_1-C_3$-alkyloxy, $C_3-C_8$-cycloalkoxy, aryl or phenyl-$C_1-C_6$-alkyl, the two $R^{1c}$ radicals are, independently of one another, H, $CH_3$ or $C_2H_5$, or $R^2OOC-C_1-C_6$-alkyl, $R^2R^3N(O)C-C_1-C_6$-alkyl, $R^2R^3N-C_2-C_6$-alkyl, where $R^2$ and $R^3$ have the same meanings as above or, if $R^1$ is $R^2R^3N(O)C-C_1-C_6$-alkyl, $R^2$ and $R^3$ together form a $C_4-C_6$-alkyl chain,

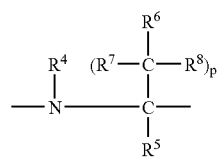

in which p is 0, 1, $R^4$ is H—, $R^9OOC-$ with $R^9=C_{1-16}$-alkyl, phenyl-$C_1-C_4$-alkyl, $R^{10}C(O)-O-CH_2-$, $R^{10}C(O)-O-CH(CH_3)-$, where $R^{10}$ can be $C_1-C_4$-alkyl, phenyl, benzyl, $C_3-C_8$-cycloalkyl or cyclohexyl-$CH_2-$, and $R^5$, $R^6$, $R^7$ and $R^8$ have the same meanings as above;

(ii)

when E is II or III, and G and K are H, then A and B have the following meanings A: $R^1OOC-CH_2-$, $R^1OOC-CH_2-CH_2-$, $R^1OOC-CH(CH_3)-$, $R^1OOC-CH(C_2H_5)-$, $HO-CH_2-CH_2-$, in which $R^1$: is H—, $C_1-C_9$-alkyl, aryl or phenyl-$C_1-C_3$-alkyl, it being possible for all the radicals mentioned apart from H to carry optionally up to three identical or different radicals selected from $C_1-C_4$-alkyl, $CF_3$, F, Cl, $NO_2$, HO or $C_1-C_4$-alkoxy radicals, in which p is 0, 1, $R^4$ is $R^9OOC-$ with $R^9=C_{7-16}$-alkyl, $R^{10}C(O)-O-CH_2-$, $R^{10}C(O)-O-CH(CH_3)-$, where $R^{10}$ can be $C_1-C_4$-alkyl, phenyl, benzyl, $C_3-C_8$-cycloalkyl or cyclohexyl-$CH_2-$, and $R^5$, $R^6$, $R^7$ and $R^8$ have the same meanings as above;

(iii)

when E is II or III, and G is —OH, —$OR^{18}$, —$OC(O)R^{19}$, $C(O)OR^{20}$, —$SR^{18}$, —$C(S)SR^{20}$, where $R^{18}$, $R^{19}$ and $R^{20}$ have the same meanings as above, and K is H, or G and K together form a $C(O)O-$, —$C(O)S-$, —$C(S)S-$ or —$C(S)O-$ group, then A and B have the following meanings:

A: $R^1OOC-CH_2-$, $R^1OOC-CH_2-CH_2-$, $R^1OOC-CH(CH_3)-$, $R^1OOC-C(CH_3)_2-$$R^1OOC-CH(C_2H_5)-$, $C_{1-4}$-alkyl-$SO_2-(CH_2)_{2-6}-$, $HO_3S-(CH_2)_{2-6}-$, 5-te-trazoylyl-$(CH_2)_{1-6}-$, $C_{1-4}$-alkyl-$O-(CH_2)_{2-6}-$, $R^2R^3N-(CH_2)_{2-6}-$, $R^2S(CH_2)_{2-6}-$, $R^2R^3NSO_2-(CH_2)_{2-6}-$, $HO-(CH_2)_{2-6}-$, $R^{1a}S(O)C-CH_2-$, $R^{1a}O(S)C-CH_2-$, $R^2R^3N(O)C-CH_2-$, $R^2R^3N-O-CO-CH_2-$, $R^2N(OH)-CO-CH_2-$, where $R^2$ and $R^3$ are, independently of one another, H, $C_1-C_6$-alkyl, or $C_3-C_8$-cycloalkyl or $R^2$ and $R^3$ form together a $C_{4-6}$-alkyl chain, in which $R^1$: is H—, $C_3-C_{16}$-alkyl-, $H_3C-[O-CH_2-CH_2]_q$ (q=1-4), $C_7-C_{12}$-bicycloalkyl-, $C_{10}$-tricycloalkyl-, $C_3-C_8$-cycloalkyl-, $C_3-C_8$-cycloalkyl-$C_1-C_3$-alkyl-, pyranyl-, piperidinyl-, aryl-, or phenyl-$C_1-C_3$-alkyl, it being possible for all the radicals mentioned apart from H to carry optionally up to four identical or different radicals selected from $C_1-C_4$-alkyl, $CF_3$, F, Cl, $NO_2$, HO or $C_1-C_4$-alkoxy radicals, or $R^1$ is 2-oxo-1,3-dioxol-4-ylmethyl which may be substituted in position 5 by $C_1-C_{16}$-alkyl or aryl, $R^{1a}$: is H—, $C_2-C_{16}$-alkyl, $H_3C-[O-CH_2-CH_2]_q$ (q=1-4), $C_{7-12}$-bicycloalkyl, $C_{10}$-tricycloalkyl, $C_3-C_8$-cycloalkyl, $C_3-C_8$-cycloalkyl-$C_1-C_3$-alkyl, aryl or phenyl-$C_1-C_3$-alkyl, it being possible for all the radicals mentioned apart from H to carry optionally up to three identical or different radicals selected from $C_1-C_4$-alkyl, $CF_3$, F, Cl, $NO_2$, HO or $C_1-C_4$-alkoxy radicals, or R$^1$: is R$^{1b}$—C(O)O—C(R$^{1c}$)$_2$—, R$^{1b}$—C(O)NR$^2$—C(R$^{1c}$)$_2$—, where R$^{1b}$ can be C$_1$–C$_4$-alkyl, C$_3$–C$_8$-cycloalkyl-C$_1$–C$_3$-alkyl, C$_3$–C$_8$-cycloalkyl, C$_1$–C$_4$-alkyloxy, C$_3$–C$_8$-cycloalkyl-C$_1$–C$_3$-alkyloxy, C$_3$–C$_8$-cycloalkoxy, aryl or phenyl-C$_1$–C$_6$-alkyl, the two R$^{1c}$ radicals are, independently of one another, H, CH$_3$ or C$_2$H$_5$, and R$^2$ has the same meaning as above, or R$^2$OOC—C$_1$–C$_6$-alkyl, R$^2$R$^3$N(O)C—C$_1$–C$_6$-alkyl, R$^2$R$^3$N—C$_2$–C$_6$-alkyl, and in which R$^2$ and R$^3$ have the same meanings as above or, if R$^1$ is R$^2$R$^3$N(O)C—C$_1$–C$_6$-alkyl, R$^2$ and R$^3$ together form a C$_4$–C$_6$-alkyl chain,

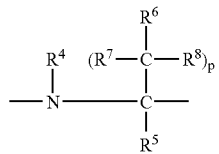

in which p is 0, 1,

R$^4$: is H—, R$^9$OOC— with R$^9$=C$_{1-3}$-alkyl, C$_{3-8}$-cycloalkyl-, phenyl-, phenyl-C$_{1-4}$-alkyl-, R$^{10}$C(O)—O—CH$_2$—, R$^{10}$C(O)—O—CH(CH$_3$)—, where R$^{10}$ can be C$_1$–C$_4$-alkyl, phenyl, benzyl, cyclohexyl or cyclohexyl-CH$_2$—, and R$^5$, R$^6$, R$^7$ and R$^8$ have the same meanings as above;

(iv)

when E is IV, V or VI, and G is H or OH and K is H, then A and B have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$—R$^1$OOC—CH(C$_2$H$_5$)—, R$^{1a}$S(O)C—CH$_2$—, R$^{1a}$O(S)C—CH$_2$—, R$^2$R$^3$N(O)C—CH$_2$—, R$^2$R$^3$N—O—CO—CH$_2$—, R$^2$N(OH)—CO—CH$_2$—, where R$^2$ and R$^3$ are, independently of one another, H, C$_1$–C$_6$-alkyl, C$_3$–C$_8$-cycloalkyl or R$^2$ and R$^3$ form together a C$_{4-6}$-alkyl chain, in which R$^1$: is C$_7$–C$_{16}$-alkyl, H$_3$C—[O—CH$_2$—CH$_2$]$_q$ (q=1–4), C$_7$–C$_{12}$-bicycloalkyl, C$_{10}$-tricycloalkyl, C$_3$–C$_8$-cycloalkyl, C$_3$–C$_8$-cycloalkyl-C$_1$–C$_3$-alkyl, it being possible for all the radicals mentioned apart from H to carry optionally up to three identical or different radicals selected from C$_1$–C$_4$-alkyl, CF$_3$, F, Cl, NO$_2$, HO or C$_1$–C$_4$-alkoxy radicals, or 2-oxo-1,3-dioxol-4-yl-methyl- which may be substituted in position 5 by C$_{1-6}$-alkyl or aryl, R$^{1a}$: is H—, C$_1$–C$_{16}$-alkyl, C$_7$–C$_{12}$-bicycloalkyl, C$_{10}$-tricycloalkyl, C$_3$–C$_8$-cycloalkyl, C$_3$–C$_8$-cycloalkyl-C$_1$–C$_3$-alkyl, aryl or phenyl-C$_1$–C$_3$-alkyl, it being possible for all the radicals mentioned apart from H to carry optionally up to three identical or different radicals selected from C$_1$–C$_4$-alkyl, CF$_3$, F, Cl, NO$_2$, HO or C$_1$–C$_4$-alkoxy radicals, or R$^1$: is R$^{1b}$—C(O)O—C(R$^{1c}$)$_2$—, R$^{1b}$—C(O)NR$^2$—C(R$^{1c}$)$_2$—, where R$^{1b}$ can be C$_1$–C$_4$-alkyl, C$_3$–C$_8$-cycloalkyl-C$_1$–C$_3$-alkyl, C$_3$–C$_8$-cycloalkyl, C$_1$–C$_4$-alkyloxy, C$_3$–C$_8$-cycloalkyl-C$_1$–C$_3$-alkyloxy, C$_3$–C$_8$-cycloalkoxy, aryl or phenyl-C$_1$–C$_6$-alkyl, the two R$^{1c}$ radicals are, independently of one another, H, CH$_3$ or C$_2$H$_5$, and R$^2$ has the same meaning as above, or R$^2$OOC—C$_1$–C$_6$-alkyl, R$^2$R$^3$N(O)C—C$_1$–C$_6$-alkyl, R$^2$R$^3$N—C$_2$–C$_6$-alkyl, and in which R$^2$ and R$^3$ have the same meanings as above or, if R$^1$ is R$^2$R$^3$N(O)C—C$_1$–C$_6$-alkyl, R$^2$ and R$^3$ together form a C$_4$–C$_6$-alkyl chain,

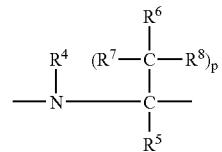

in which p is 0, 1,

R$^4$ is H—, R$^9$OOC— with R$^9$=C$_{1-16}$-alkyl, phenyl-C$_1$–C$_4$-alkyl, R$^{10}$C(O)—O—CH$_2$—, R$^{10}$C(O)—O—CH(CH$_3$)—, where R$^{10}$ can be C$_1$–C$_4$-alkyl, phenyl, benzyl, C$_3$–C$_8$-cycloalkyl or cyclohexyl-CH$_2$—, and R$^5$, R$^6$, R$^7$ and R$^8$ have the same meanings as above;

(v)

when E is IV, V or VI, and G is H or OH and K is H, then A and B have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$—R$^1$OOC—CH(C$_2$H$_5$)—, HO—(CH$_2$)$_{2-6}$—, in which R$^1$: is H—, C$_1$–C$_9$-alkyl, aryl or phenyl-C$_1$–C$_3$-alkyl, it being possible for all the radicals mentioned apart from H to carry optionally up to three C$_1$–C$_4$-alkyl, CF$_3$, F, Cl, NO$_2$, HO or C$_1$–C$_4$-alkoxy radicals,

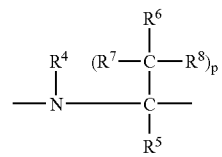

in which p is 0, 1,

R$^4$ is R$^9$OOC— with R$^9$=C$_{7-16}$-alkyl, R$^{10}$C(O)—O—CH$_2$—, R$^{10}$C(O)—O—CH(CH$_3$)—, where R$^{10}$ can be C$_1$–C$_4$-alkyl, phenyl, benzyl, C$_3$–C$_8$-cycloalkyl or cyclohexyl-CH$_2$—, and R$^5$, R$^6$, R$^7$ and R$^8$ have the same meanings as above;

(vi)

when E is IV, V or VI, and G is —OR$^{18}$, —OC(O)R$^{19}$, C(O)OR$^{20}$, —SR$^{18}$, —C(S)SR$^{20}$, where R$^{18}$, R$^{19}$ and R$^{20}$ have the same meanings as above, and K is H, or G and K together form a —C(O)O—, —C(O)S—, C(S)S— or —C(S)O— group, then A and B have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$—R$^1$OOC—CH(C$_2$H$_5$)—, HO—CH$_2$—CH$_2$—, R$^{1a}$S(O)C—CH$_2$—, R$^{1a}$O(S)C—CH$_2$—, R$^2$R$^3$N(O)C—CH$_2$—, R$^2$R$^3$N—O—

CO—CH$_2$—, R$^2$N(OH)—CO—CH$_2$—, where R$^2$ and R$^3$ are, independently of one another, H, C$_1$–C$_6$-alkyl, C$_3$–C$_8$-cycloalkyl or R$^2$ and R$^3$ form together a C$_{4-6}$-alkyl chain, in which R$^1$: is H—, C$_1$–C$_{16}$-alkyl-, H$_3$C—[O—CH$_2$—CH$_2$]$_q$ (q=1–4), C$_7$–C$_{12}$-bicycloalkyl-, C$_{10}$-tricycloalkyl-, C$_3$–C$_8$-cycloalkyl-, C$_3$–C$_8$-cycloalkyl-C$_1$–C$_3$-alkyl-, pyranyl-, piperidinyl-, aryl-, or phenyl-C$_1$–C$_3$-alkyl, it being possible for all the radicals mentioned apart from H to carry optionally up to three identical or different radicals selected from C$_1$–C$_4$-alkyl, CF$_3$, F, Cl, NO$_2$, HO or C$_1$–C$_4$-alkoxy radicals, or R$^1$ is 2-oxo-1,3-dioxol-4-ylmethyl which may be substituted in position 5 by C$_1$–C$_{16}$-alkyl or aryl, R$^{1a}$: is H—, C$_1$–C$_{16}$-alkyl, H$_3$C—[O—CH$_2$—CH$_2$]$_q$ (q=1–4), C$_7$–C$_{12}$-bicycloalkyl, C$_{10}$-tricycloalkyl, C$_3$–C$_8$-cycloalkyl, C$_3$–C$_8$-cycloalkyl-C$_1$–C$_3$-alkyl, aryl or phenyl-C$_1$–C$_3$-alkyl, it being possible for all the radicals mentioned apart from H to carry optionally up to three identical or different radicals selected from C$_1$–C$_4$-alkyl, CF$_3$, F, Cl, NO$_2$, HO or C$_1$–C$_4$-alkoxy radicals, or R$^1$: is R$^{1b}$—C(O)O—C(R$^{1c}$)$_2$—, R$^{1b}$—C(O)NR$^2$—C(R$^{1c}$)$_2$—, where R$^{1b}$ can be C$_1$–C$_4$-alkyl, C$_3$–C$_8$-cycloalkyl-C$_1$–C$_3$-alkyl, C$_3$–C$_8$-cycloalkyl, C$_1$–C$_4$-alkyloxy, C$_3$–C$_8$-cycloalkyl-C$_1$–C$_3$-alkyloxy, C$_3$–C$_8$-cycloalkoxy, aryl or phenyl-C$_1$–C$_6$-alkyl, the two R$^{1c}$ radicals are, independently of one another, H, CH$_3$ or C$_2$H$_5$, or R$^2$OOC—C$_1$–C$_6$-alkyl, R$^2$R$^3$N(O)C—C$_1$–C$_6$-alkyl, R$^2$R$^3$N—C$_2$–C$_6$-alkyl, and in which R$^2$ and R$^3$ have the same meanings as above or, if R$^1$ is R$^2$R$^3$N(O)C—C$_1$–C$_6$-alkyl, R$^2$ and R$^3$ together form a C$_4$–C$_6$-alkyl chain,

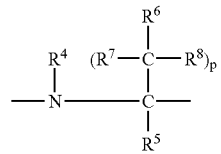

in which p is 0, 1,

R$^4$: is H—, R$^9$OOC— with R$^9$=C$_{1-16}$-alkyl, C$_{3-8}$-cycloalkyl-, phenyl-, phenyl-C$_{1-4}$-alkyl-, R$^{10}$C(O)—O—CH$_2$—, R$^{10}$C(O)—O—CH(CH$_3$)—, where R$^{10}$ can be C$_1$–C$_4$-alkyl, phenyl, benzyl, C$_3$–C$_8$-cycloalkyl or cyclohexyl-CH$_2$—, and R$^5$, R$^6$, R$^7$ and R$^8$ have the same meanings as above;

and the physiologically tolerated salts thereof.

The amino acid derivatives represented by B are preferably in the D-configuration, the amino acid derivatives represented by E in the L-configuration.

The aforementioned compounds belong to three groups of substances:

The first group comprises prodrugs of thrombin inhibitors (e.g. G equals —OH, —OR$^{18}$, —COOR$^{20}$ etc.) which is a substance to only a negligible antithromotic effect, which, however, are converted in the organism into the active substance (G equals H). These are compounds of groups (iii) and (vi), partially also of groups (iv) and (v). The advantage of the prodrugs lies in their improved pharmacokinetic and pharmacodynamic behaviour in the organism.

The second group comprises prodrugs of thrombin inhibitors which show already as a prodrug a thrombin-inhibiting effect (e.g. A equals R$^1$OOC—CH$_2$—, R$^1$OOC—CH$_2$—CH$_2$—, R$^1$OOC—CH(CH$_3$)— etc. in combination with G equals —H). The effective substance formed in the organism (drug; A equals HOOC—CH$_2$—, HOOC—CH$_2$—CH$_2$—, HOOC—CH(CH$_3$)— etc., G equals —H) shows also a thrombin-inhibiting effect. These are in part compounds of groups (i), (ii), (iv) and (v). The advantage of these prodrugs lies also in their improved pharmacokinetic and pharmacodynamic behaviour in the organism. Compounds wherein G equals —OH, —OR$^{18}$, —COOR$^{20}$ etc., and simultaneously A equals R$^1$OOC—CH$_2$—, R$^1$OOC—CH$_2$—CH$_2$—, R$^1$OOC—CH(CH$_3$)— etc. are double prodrugs which are converted in the organism into the respective drug (G equals —H, A equals HOOC—CH$_2$— etc.) by converting both prodrug groups.

The third group comprises thromin inhibitors which per se show the antithrombotic effect (e.g. A equals C$_{1-4}$-alkyl-SO$_2$—(CH$_2$)$_{2-6}$—, HO$_3$—S—(CH$_2$)$_{2-6}$—, 5-tetrazolyl-(CH$_2$)$_{1-6}$—, C$_{1-4}$-alkyl-O—(CH$_2$)$_{2-6}$—, R$^2$R$^3$N—(CH$_2$)$_{2-6}$—, R$^2$S—(CH$_2$)$^{2-6}$—, R$^2$R$^3$NSO$_2$—(CH$_2$)$_{2-6}$—, in combination with G equals —H). Such compounds are included in group (i).

Preferred compound of the formula I are those in which A, B, D, E, G and K have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$—R$^{1a}$S(O)C—CH$_2$—, R$^{1a}$O(S)C—CH$_2$—, R$^2$R$^3$N(O)C—CH$_2$—, R$^2$R$^3$N—O—CO—CH$_2$—, R$^2$N(OH)—CO—CH$_2$—, C$_{1-4}$-alkyl-SO$_2$—(CH$_2$)$_{2-6}$—, HO$_3$S—(CH$_2$)$_{2-6}$—, 5-te-trazyolyl-(CH$_2$)$_{1-6}$—, C$_{1-4}$-alkyl-O—(CH$_2$)$_{2-6}$—, R$^2$R$^3$N—(CH$_2$)$_{2-6}$—, R$^2$S(CH$_2$)$_{2-6}$—, R$^2$R$^3$NSO$_2$—(CH$_2$)$_{2-6}$—, where R$^2$ and R$^3$ are, independently of one another, H, C$_1$–C$_6$-alkyl, C$_3$–C$_8$-cycloalkyl or R$^2$ and R$^3$ form together a butylene or pentylen chain, in which R$^1$: is H—, C$_1$–C$_{16}$-alkyl-, H$_3$C—[O—CH$_2$—CH$_2$]$_q$ (q=1–4), C$_7$–C$_{12}$-bicycloalkyl-, C$_{10}$-tricycloalkyl-, C$_3$–C$_8$-cycloalkyl-, C$_5$–C$_8$-cycloalkyl-C$_1$–C$_3$-alkyl-, pyranyl-, piperidinyl-, aryl-, or phenyl-C$_1$–C$_3$-alkyl, it being possible for all the radicals mentioned apart from H to carry optionally up to four identical or different radicals selected from CH$_3$, CF$_3$, F, Cl, HO or methoxy radicals, or R$^1$ is 2-oxo-1,3-dioxol-4-ylmethyl which may be substituted in position 5 by C$_1$–C$_6$-alkyl or aryl, R$^{1a}$: is H—, C$_1$–C$_{16}$-alkyl, C$_7$–C$_{12}$-bicycloalkyl, C$_{10}$-tricycloalkyl, C$_5$–C$_8$-cycloalkyl, C$_5$–C$_8$-cycloalkyl-C$_1$–C$_3$-alkyl, aryl or phenyl-C$_1$–C$_3$-alkyl, it being possible for all the radicals mentioned apart from H to carry optionally up to four identical of different radicals selected from CH$_3$, CF$_3$, F, Cl, HO or methoxy radicals, or R$^1$: is R$^{1b}$—C(O)O—C(R$^{1c}$)$_2$—, R$^{1b}$—C(O)NR$^2$—C(R$^{1c}$)$_2$—, where R$^{1b}$ can be C$_1$–C$_4$-alkyl, C$_5$–C$_8$-Cycloalkyl-C$_1$–C$_3$-alkyl, C$_5$–C$_8$-cycloalkyl, C$_1$–C$_4$-alkyloxy, C$_5$–C$_8$-cycloalkyl-C$_1$–C$_3$-alkyloxy, C$_5$–C$_8$-cycloalkoxy, aryl or phenyl-C$_1$–C$_3$-alkyl, the two R$^{1c}$ radicals are, independently of one another, H, CH$_3$ or C$_2$H$_5$, or R$^2$OOC—C$_1$–C$_6$-alkyl, R$^2$R$^3$N(O)C—C$_1$–C$_6$-alkyl, R$^2$R$^3$N—C$_2$–C$_6$-alkyl, and in which R$^2$ and R³ have the same meanings as above or, if R¹ is R²R³N(O)C—C₁–C₆-alkyl, R² and R³ together form a butylene or pentylene chain, $$-\underset{|}{N}-\underset{|}{\overset{R^4}{C}}-(R^7-\overset{R^6}{\underset{R^8}{C}}-)_p$$
(with R⁵ on central C)

in which p is 0, 1,

R⁴: is H—, R⁹OOC— with R⁹=C₁₋₁₆-alkyl, C₃₋₈-cycloalkyl-, R¹⁰C(O)—O—CH₂—, R¹⁰C(O)—O—CH(CH₃)—, where R¹⁰ can be C₁–C₄-alkyl, phenyl, benzyl, C₅–C₈-cycloalkyl or cyclohexyl-CH₂—, R⁵ is H—, R⁶ is C₁₋₈-alkyl, C₅₋₈-cycloalkyl, which may carry up to four methyl radicals, bicyclo[2.2.2]octyl, bicyclo[2.2.1]heptyl, norbornyl, adamantyl, indanyl, decalinyl, R⁷ is H, R⁸ is H,

E

II (3-pyrroline-2-carbonyl-N-methyl)

IV (pyrrolidine-2-carbonyl-N-methyl)

VI (azetidine-2-carbonyl-N-methyl)

D (various thiophene and furan substituents with R¹⁴, R¹⁵, CH₃)

-continued (furan, thiazole, oxazole, isoxazole substituents with R¹⁷)

in which

R¹⁴: is H, CH₃, Cl

R¹⁵: is H, CF₃,

R¹⁷: is H, CH₃, CF₃,

G: H, —OH, —OR¹⁸, —OC(O)R¹⁹, —C(O)OR²⁰, in which

R¹⁸: is —C₁₋₈-alkyl, —C₁–C₃-alkyl-C₃–C₈-cycloalkyl, —C₁–C₃-alkylphenyl which may carry optionally up to three CH₃, CF₃, F, Cl or methoxy radicals, R¹⁹: is —C₁₋₃-alkyl, R²⁰: is —C₁₋₈-alkyl, —CH₂CCl₃, —C₁–C₃-alkyl-C₅–C₈-cycloalkyl, —C₅–C₈-cycloalkyl, -phenyl or —C₁–C₃-alkylphenyl, each of which may carry optionally up to three CH₃, CF₃, F, Cl or methoxy radicals, —CH₂O—C(O)R¹⁰ᵃ, —CH(CH₃)O—C(O)R¹⁰ᵃ, where R¹⁰ᵃ can be —C₁–C₈-alkyl, -phenyl, -benzyl, —C₅–C₈-cycloalkyl or —CH₂-cyclohexyl, or —C(R¹⁰ᵇ)₂—CH₂—O—(O)CR¹⁰, where the R¹⁰ᵇ radicals can be, independently of one another, H or CH₃, and R¹⁰ᶜ is —C₁–C₃-alkyl-C₅–C₈-cycloalkyl, —C₅–C₈-cycloalkyl or —C₁–C₄-alkyl, or K is H or G and K together form a —C(O)O— or —C(O)S— group.

Particularly preferred compounds of the formula I are those in which A, B, D, E, G and K have the following meanings:

A: R¹OOC—CH₂—, R¹OOC—CH₂—CH₂—, R¹OOC—CH(CH₃)—, R¹OOC—C(CH₃)₂—R²R³N(O)C—CH₂—, C₁₋₄-alkyl-SO₂—(CH₂)₂₋₆—, 5-tetrazyolyl-(CH₂)₁₋₆—, C₁₋₄-alkyl (CH₂)₂₋₆—, R²R³N—(CH₂)₂₋₆—, R²S(CH₂)₂₋₆—, —R²R³NSO₂—(CH₂)₂₋₆—, where R² and R³ are independently of one another, H or C₁–C₄-alkyl in which R¹: is H—, C₁–C₁₆-alkyl, H₃C—[O—CH₂—CH₂]_q (q=1–4), C₁₀-tricycloalkyl, C₅–C₈-cycloalkyl, C₅–C₈-cycloalkyl-C₁–C₃-alkyl, phenyl-C₁–C₃-alkyl, it being possible for all the radicals mentioned apart from H to carry optionally up to three identical or different radicals selected from CH₃, CF₃, F, Cl, HO or methoxy radicals, or R¹ is 2-oxo-1,3-dioxol-4-ylmethyl which may be substituted in position 5 by C₁–C₃-alkyl or aryl, or R$^1$: is R$^{1b}$—C(O)O—C(R$^{1c}$)$_2$—, where R$^{1b}$ can be C$_1$–C$_4$-alkyl, C$_5$–C$_8$-cycloalkyl, C$_1$–C$_4$-alkyloxy, C$_5$–C$_8$-cycloalkyloxy or phenyl-C$_1$–C$_3$-alkyl, the two R$^{1c}$ radicals are, independently of one another, H or CH$_3$, or R$^2$OOC—C$_1$–C$_6$-alkyl, R$^2$R$^3$N(O)C—C$_1$–C$_6$-alkyl, R$^2$R$^3$N—C$_2$–C$_6$-alkyl, and in which R$^2$ and R$^3$ have the same meanings as above or, if R$^1$ is R$^2$R$^3$N(O)C—C$_1$–C$_6$-alkyl, R$^2$ and R$^3$ together form a butylene or pentylene chain,

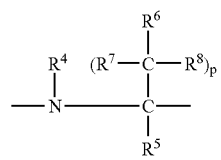

in which p is 0, 1,

R$^4$ is H—, R$^9$OOC— with R$^9$=C$_{1-16}$-alkyl, R$^{10}$C(O)—O—CH$_2$—, R$^{10}$C(O)—O—CH(CH$_3$)—, where R$^{10}$ can be C$_1$–C$_4$-alkyl, R$^5$ is H—, R$^6$ is C$_{1-8}$-alkyl, cyclopentyl, cyclohexyl, cycloheptyl, bicyclo[2.2.2]octyl, bicyclo[2.2.1]heptyl, norbornyl, adamantyl, indanyl, decalinyl, R$^7$ is H, R$^8$ is H,

E

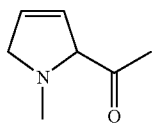 II

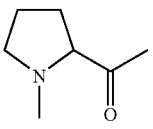 IV

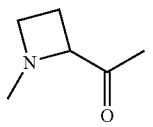 VI

D

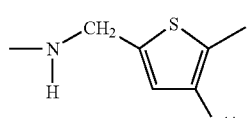

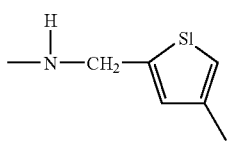, 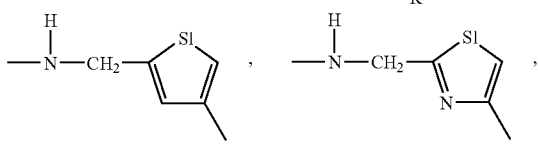

-continued

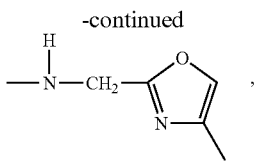

in which

R$^{14}$: is H, CH$_3$, Cl

G: H, —OH, —OR$^{18}$, —C(O)OR$^{20}$, in which

R$^{18}$: is —C$_{1-8}$-alkyl, —C$_1$–C$_3$-alkyl-C$_3$–C$_8$-cycloalkyl, —C$_1$–C$_3$-alkylphenyl which may carry optionally up to three CH$_3$, CF$_3$, F, Cl, or methoxy radicals, R$^{20}$: is —C$_{1-8}$-alkyl, —C$_1$–C$_3$-alkyl-C$_5$–C$_8$-cycloalkyl, —C$_5$–C$_8$-cycloalkyl or —C$_1$–C$_3$-alkylphenyl which may carry optionally up to three CH$_3$, CF$_3$, F, Cl or methoxy radicals, or —CH$_2$O—C(O)R$^{10a}$, —CH(CH$_3$)O—C(O)R$^{10a}$, where R$^{10a}$ can be —C$_1$–C$_4$-alkyl, -benzyl, —C$_5$–C$_8$-cycloalkyl or —CH$_2$-cyclohexyl, K is H, or G and K together form a —C(O)O— or —C(O)S— group.

Very particularly preferred are compounds of the formula I as claimed in claim 1, where A, B, D, E, G and K have the following meanings A: R$^1$OOC—CH$_2$—, R$^1$OOC—CH$_2$—CH$_2$—, R$^1$OOC—CH(CH$_3$)—, R$^1$OOC—C(CH$_3$)$_2$—C$_{1-4}$-alkyl-SO$_2$—(CH$_2$)$_{2-6}$—, 5-tetrazyolyl-(CH$_2$)$_{1-6}$—C$_{1-4}$-alkyl-O—(CH$_2$)$_{2-6}$—, H$_2$N—(CH$_2$)$_{2-3}$—, CH$_3$—NH—(CH$_2$)$_{2-3}$—, (CH$_3$)$_2$N—(CH$_2$)$_{2-3}$—, H$_2$NSO$_2$—(CH$_2$)$_{2-4}$—, CH$_3$—NHSO$_2$—(CH$_2$)$_{2-4}$—, in which R$^1$: is H—, C$_1$–C$_8$-alkyl-, C$_5$–C$_8$-cycloalkyl-, C$_5$–C$_8$-cycloalkyl-C$_1$–C$_3$-alkyl-, it being possible for all the radicals mentioned apart from H to carry optionally up to four identical or different radicals selected from CH$_3$, CF$_3$, F, Cl, or methoxy radicals, or R$^1$ is 2-oxo-1,3-dioxo-4-yl-methyl which may be substituted in the 5-position by C$_1$–C$_3$-alkyl or aryl, or R$^1$: is R$^{1b}$—C(O)O—CH$_2$—, R$^{1b}$—C(O)O—CH(CH$_3$)—, where R$^{1b}$ can be C$_1$–C$_4$-alkyl-, C$_5$–C$_8$-cycloalkyl-, C$_1$–C$_4$-alkyloxy- or C$_5$–C$_8$-cycloalkyloxy-,

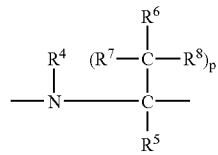

in which p is 0,1,

R$^4$ is H—,

R$^5$ is H—,

R$^6$ is cyclopentyl, cyclohexyl, cycloheptyl,

R$^7$ is H,

R$^8$ is H,

E

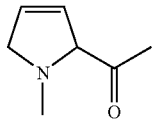

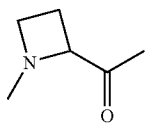

D

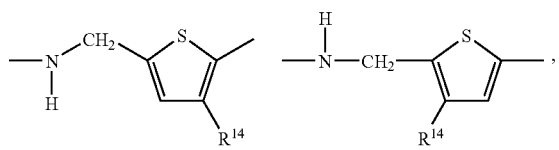

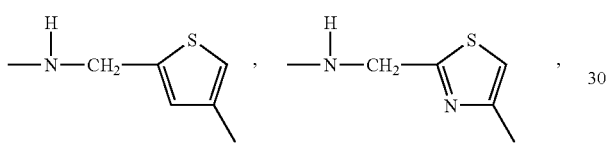

in which
R$^{14}$: is H, CH$_3$, Cl,
G: is —OH, —C(O)OR$^{20}$, in which
R$^{20}$: is —C$_{1-8}$-alkyl, —C$_1$-C$_3$-alkyl-C$_5$-C$_8$-cycloalkyl,
K is H.

Very preferred compounds of the formula I are those in which A, B, D, E, G, and K have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$— in which
R$^1$: is C$_1$-C$_8$-alkyl-, C$_5$-C$_8$-cycloalkyl-, C$_5$-C$_8$-cycloalkyl-CH$_2$-alkyl-, it being possible for all the radicals mentioned to carry optionally up to four identical or different radicals selected from CH$_3$ or methoxy radicals,

II

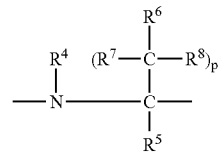

in which
p is 0,1,
R$^4$ is H—,
R$^5$ is H—,
R$^6$ is cyclohexyl,
R$^7$ is H,
R$^8$ is H,

E

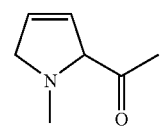   II

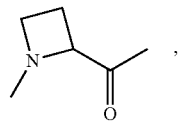   VI

D

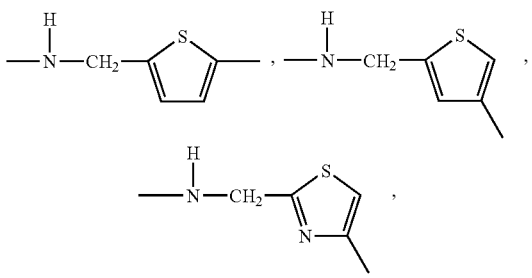

G: is —OH,
K is H.

The following substances are very particularly preferred:

1. CH$_3$OOC—CH$_2$—(D)-Chg-Pyr-NH—CH$_2$-5-[2-am-(OH)]-thioph
2. EtOOC—CH$_2$—(D)-Chg-Pyr-NH—CH$_2$-5-[2-am-(OH)]-thioph
3. nPrOOC—CH$_2$—(D)-Chg-Pyr-NH—CH$_2$-5-[2-am-(OH)]-thioph
4. iPrOOC—CH$_2$—(D)-Chg-Pyr-NH—CH$_2$-5-[2-am-(OH)]-thioph
5. nBuOOC—CH$_2$—(D)-Chg-Pyr-NH—CH$_2$-5-[2-am-(OH)]-thioph
6. tBuOOC—CH$_2$—(D)-Chg-Pyr-NH—CH$_2$-5-[2-am-(OH)]-thioph
7. iBuOOC—CH$_2$—(D)-Chg-Pyr-NH—CH$_2$-5-[2-am-(OH)]-thioph
8. nPentOOC—CH$_2$—(D)-Chg-Pyr-NH—CH$_2$-5-[2-am-(OH)]-thioph
9. iPentOOC—CH$_2$—(D)-Chg-Pyr-NH—CH$_2$-5-[2-am-(OH)]-thioph
10. neoPentOOC—CH$_2$—(D)-Chg-Pyr-NH—CH$_2$-5-[2-am-(OH)]-thioph
11. nHexOOC—CH$_2$—(D)-Chg-Pyr-NH—CH$_2$-5-[2-am-(OH)]-thioph
12. cHex-OC—CH$_2$—(D)-Chg-Pyr-NH—CH$_2$-5-[2-am-(OH)]-thioph
13. nHeptOOC—CH$_2$—(D)-Chg-Pyr-NH—CH$_2$-5-[2-am-(OH)]-thioph -continued

| | |
|---|---|
| 14. | nOctOOC—CH₂—(D)-Chg-Pyr-NH—CH₂-5-[2-am-(OH)]-thioph |
| 15. | cOctOOC—CH₂—(D)-Chg-Pyr-NH—CH₂-5-[2-am-(OH)]-thioph |
| 16. | BnOOC—CH₂—(D)-Chg-Pyr-NH—CH₂-5-[2-am-(OH)]-thioph |
| 17. | AdaOOC—CH₂—(D)-Chg-Pyr-NH—CH₂-5-[2-am-(OH)]-thioph |
| 18. | AdaOOC—CH₂—(D)-Chg-Dep-NH—CH₂-5-[2-am-(OH)]-thioph |
| 19. | cHex-CH₂OOC—CH₂—(D)-Chg-Pyr-NH—CH₂-5-[2-am-(OH)]-thioph |
| 20. | AdaOOC—CH₂—(D)-Chg-Pyr-NH—CH₂-5-[2-am-(H)]-thioph |
| 21. | cHex-CH₂OOC—CH₂—(D)-Chg-Pyr-NH—CH₂-5-[2-am-(H)]-thioph |
| 22. | CH₃—(CH₂)₁₀OOC—CH₂—(D)-Chg-Pyr-NH—CH₂-5-[2-am-(OH)]-thioph |
| 23. | CH₃—(CH₂)₁₅OOC—CH₂—(D)-Chg-Pyr-NH—CH₂-5-[2-am-(OH)]-thioph |
| 24. | CH₃—(CH₂)₁₀OOC—CH₂—(D)-Chg-Pyr-NH—CH₂-5-[2-am-(H)]-thioph |
| 25. | CH₃—(CH₂)₁₅OOC—CH₂—(D)-Chg-Pyr-NH—CH₂-5-[2-am-(H)]-thioph |
| 26. | CH₃OOC—CH₂—(D)-Cha-Pyr-NH—CH₂-5-[2-am-(OH)]-thioph |
| 27. | CH₃OOC—CH₂—(D)-Cha-Dep-NH—CH₂-5-[2-am-(OH)]-thioph |
| 28. | EtOOC—CH₂—(D)-Cha-Pyr-NH—CH₂-5-[2-am-(OH)]-thioph |
| 29. | nPrOOC—CH₂—(D)-Cha-Pyr-NH—CH₂-5-[2-am-(OH)]-thioph |
| 30. | nPrOOC—CH₂—(D)-Cha-Dep-NH—CH₂-5-[2-am-(OH)]-thioph |
| 31. | iPrOOC—CH₂—(D)-Cha-Pyr-NH—CH₂-5-[2-am-(OH)]-thioph |
| 32. | nBuOOC—CH₂—(D)-Cha-Pyr-NH—CH₂-5-[2-am-(OH)]-thioph |
| 33. | tBuOOC—CH₂—(D)-Cha-Pyr-NH—CH₂-5-[2-am-(OH)]-thioph |
| 34. | iBuOOC—CH₂—(D)-Cha-Pyr-NH—CH₂-5-[2-am-(OH)]-thioph |
| 35. | nPentOOC—CH₂—(D)-Cha-Pyr-NH—CH₂-5-[2-am-(OH)]-thioph |
| 36. | iPentOOC—CH₂—(D)-Cha-Pyr-NH—CH₂-5-[2-am-(OH)]-thioph |
| 37. | neoPentOOC—CH₂—(D)-Cha-Pyr-NH—CH₂-5-[2-am-(OH)]-thioph |
| 38. | nHexOOC—CH₂—(D)-Cha-Pyr-NH—CH₂-5-[2-am-(OH)]-thioph |
| 39. | cHex-OC—CH₂—(D)-Cha-Pyr-NH—CH₂-5-[2-am-(OH)]-thioph |
| 40. | nHeptOOC—CH₂—(D)-Cha-Pyr-NH—CH₂-5-[2-am-(OH)]-thioph |
| 41. | nOctOOC—CH₂—(D)-Cha-Pyr-NH—CH₂-5-[2-am-(OH)]-thioph |
| 42. | cOctOOC—CH₂—(D)-Cha-Pyr-NH—CH₂-5-[2-am-(OH)]-thioph |
| 43. | BnOOC—CH₂—(D)-Cha-Pyr-NH—CH₂-5-[2-am-(OH)]-thioph |
| 44. | AdaOOC—CH₂—(D)-Cha-Pyr-NH—CH₂-5-[2-am-(OH)]-thioph |
| 45. | cHex-CH₂OOC—CH₂—(D)-Cha-Pyr-NH—CH₂-5-[2-am-(OH)]-thioph |
| 46. | CH₃—(CH₂)₁₀OOC—CH₂—(D)-Cha-Pyr-NH—CH₂-5-[2-am-(OH)]-thioph |
| 47. | CH₃—(CH₂)₁₀OOC—CH₂—(D)-Cha-Pyr-NH—CH₂-5-[2-am-(OH)]-thioph |
| 48. | CH₃—(CH₂)₁₅OOC—CH₂—(D)-Cha-Pyr-NH—CH₂-5-[2-am-(OH)]-thioph |
| 49. | AdaOOC—CH₂—(D)-Cha-Pyr-NH—CH₂-5-[2-am-(H)]-thioph |
| 50. | cHex-CH₂OOC—CH₂—(D)-Cha-Pyr-NH—CH₂-5-[2-am-(H)]-thioph |
| 51. | CH₃—(CH₂)₁₀OOC—CH₂—(D)-Cha-Pyr-NH—CH₂-5-[2-am-(H)]-thioph |
| 52. | CH₃—(CH₂)₁₅OOC—CH₂—(D)-Cha-Pyr-NH—CH₂-5-[2-am-(H)]-thioph |
| 53. | CH₃OOC—CH₂—(D)-Cha-Pyr-NH—CH₂-5-[2-am-(OMe)]-thioph |
| 54. | CH₃OOC—CH₂—(D)-Cha-Dep-NH—CH₂-5-[2-am-(OMe)]-thioph |
| 55. | EtOOC—CH₂—(D)-Cha-Pyr-NH—CH₂-5-[2-am-(OMe)]-thioph |
| 56. | nPrOOC—CH₂—(D)-Cha-Pyr-NH—CH₂-5-[2-am-(OMe)]-thioph |
| 57. | CH₃OOC—CH₂—(D)-Cha-Pyr-NH—CH₂-5-[3-am-(OH)]-thioph |
| 58. | nPrOOC—CH₂—(D)-Chg-Pyr-NH—CH₂-5-[3-am-(OH)]-thioph |
| 59. | iPrOOC—CH₂—(D)-Chg-Pyr-NH—CH₂-5-[3-am-(OH)]-thioph |
| 60. | nBuOOC—CH₂—(D)-Chg-Pyr-NH—CH₂-5-[3-am-(OH)]-thioph |
| 61. | nBuOOC—CH₂—(D)-Chg-Dep-NH—CH₂-5-[3-am-(OH)]-thioph |
| 62. | iBuOOC—CH₂—(D)-Chg-Pyr-NH—CH₂-5-[3-am-(OH)]-thioph |
| 63. | nPentOOC—CH₂—(D)-Chg-Pyr-NH—CH₂-5-[3-am-(OH)]-thioph |
| 64. | iPentOOC—CH₂—(D)-Chg-Pyr-NH—CH₂-5-[3-am-(OH)]-thioph |
| 65. | neoPentOOC—CH₂—(D)-Chg-Pyr-NH—CH₂-5-[3-am-(OH)]-thioph |
| 66. | nHeptOOC—CH₂—(D)-Chg-Pyr-NH—CH₂-5-[3-am-(OH)]-thioph |
| 67. | nOctOOC—CH₂—(D)-Chg-Pyr-NH—CH₂-5-[3-am-(OH)]-thioph |
| 68. | nOctOOC—CH₂—(D)-Chg-Dep-NH—CH₂-5-[3-am-(OH)]-thioph |
| 69. | cOctOOC—CH₂—(D)-Chg-Pyr-NH—CH₂-5-[3-am-(OH)]-thioph |
| 70. | BnOOC—CH₂—(D)-Chg-Pyr-NH—CH₂-5-[3-am-(OH)]-thioph |
| 71. | AdaOOC—CH₂—(D)-Chg-Pyr-NH—CH₂-5-[3-am-(OH)]-thioph |
| 72. | cHex-CH₂OOC—CH₂—(D)-Chg-Pyr-NH—CH₂-5-[3-am-(OH)]-thioph |
| 73. | CH₃—(CH₂)₁₀OOC—CH₂—(D)-Chg-Pyr-NH—CH₂-5-[3-am-(OH)]-thioph |
| 74. | CH₃—(CH₂)₁₅OOC—CH₂—(D)-Chg-Pyr-NH—CH₂-5-[3-am-(OH)]-thioph |
| 75. | AdaOOC—CH₂—(D)-Chg-Pyr-NH—CH₂-5-[3-am-(H)]-thioph |
| 76. | cHex-CH₂OOC—CH₂—(D)-Chg-Pyr-NH—CH₂-5-[3-am-(H)]-thioph |
| 77. | CH₃—(CH₂)₁₀OOC—CH₂—(D)-Chg-Pyr-NH—CH₂-5-[3-am-(H)]-thioph |
| 78. | CH₃—(CH₂)₁₅OOC—CH₂—(D)-Chg-Pyr-NH—CH₂-5-[3-am-(H)]-thioph |
| 79. | EtOOC—CH₂—(D)-Chg-Pyr-NH—CH₂-5-[3-am-(OMe)]-thioph |
| 80. | tBuOOC—CH₂—(D)-Chg-Pyr-NH—CH₂-5-[3-am-(OMe)]-thioph |
| 81. | CH₃OOC—CH₂—(D)-Cha-Pyr-NH—CH₂-5-[3-am-(OH)]-thioph |
| 82. | CH₃OOC—CH₂—(D)-Cha-Dep-NH—CH₂-5-[3-am-(OH)]-thioph |
| 83. | EtOOC—CH₂—(D)-Cha-Pyr-NH—CH₂-5-[3-am-(OH)]-thioph |
| 84. | nPrOOC—CH₂—(D)-Cha-Pyr-NH—CH₂-5-[3-am-(OH)]-thioph |
| 85. | iPrOOC—CH₂—(D)-Cha-Pyr-NH—CH₂-5-[3-am-(OH)]-thioph |
| 86. | nBuOOC—CH₂—(D)-Cha-Pyr-NH—CH₂-5-[3-am-(OH)]-thioph |
| 87. | tBuOOC—CH₂—(D)-Cha-Pyr-NH—CH₂-5-[3-am-(OH)]-thioph |
| 88. | iBuOOC—CH₂—(D)-Cha-Pyr-NH—CH₂-5-[3-am-(OH)]-thioph |
| 89. | nPentOOC—CH₂—(D)-Cha-Pyr-NH—CH₂-5-[3-am-(OH)]-thioph |
| 90. | nPentOOC—CH₂—(D)-Cha-Dep-NH—CH₂-5-[3-am-(OH)]-thioph |
| 91. | iPentOOC—CH₂—(D)-Cha-Pyr-NH—CH₂-5-[3-am-(OH)]-thioph |
| 92. | neoPentOOC—CH₂—(D)-Cha-Pyr-NH—CH₂-5-[3-am-(OH)]-thioph |

-continued

| | |
|---|---|
| 93. | nHexOOC—CH₂—(D)-Cha-Pyr-NH—CH₂-5-[3-am-(OH)]-thioph |
| 94. | cHex-OC—CH₂—(D)-Cha-Pyr-NH—CH₂-5-[3-am-(OH)]-thioph |
| 95. | nHeptOOC—CH₂—(D)-Cha-Pyr-NH—CH₂-5-[3-am-(OH)]-thioph |
| 96. | nOctOOC—CH₂—(D)-Cha-Pyr-NH—CH₂-5-[3-am-(OH)]-thioph |
| 97. | cOctOOC—CH₂—(D)-Cha-Pyr-NH—CH₂-5-[3-am-(OH)]-thioph |
| 98. | BnOOC—CH₂—(D)-Cha-Pyr-NH—CH₂-5-[3-am-(OH)]-thioph |
| 99. | BnOOC—CH₂—(D)-Cha-Dep-NH—CH₂-5-[3-am-(OH)]-thioph |
| 100. | AdaOOC—CH₂—(D)-Cha-Pyr-NH—CH₂-5-[3-am-(OH)]-thioph |
| 101. | cHex-CH₂OOC—CH₂—(D)-Cha-Pyr-NH—CH₂-5-[3-am-(OH)]-thioph |
| 102. | CH₃—(CH₂)₁₀OOC—CH₂—(D)-Cha-Pyr-NH—CH₂-5-[3-am-(OH)]-thioph |
| 103. | CH₃—(CH₂)₁₅OOC—CH₂—(D)-Cha-Pyr-NH—CH₂-5-[3-am-(OH)]-thioph |
| 104. | AdaOOC—CH₂—(D)-Cha-Pyr-NH—CH₂-5-[3-am-(H)]-thioph |
| 105. | cHex-CH₂OOC—CH₂—(D)-Cha-Pyr-NH—CH₂-5-[3-am-(H)]-thioph |
| 106. | CH₃—(CH₂)₁₀OOC—CH₂—(D)-Cha-Pyr-NH—CH₂-5-[3-am-(H)]-thioph |
| 107. | CH₃—(CH₂)₁₅OOC—CH₂—(D)-Cha-Pyr-NH—CH₂-5-[3-am-(H)]-thioph |
| 108. | CH₃OOC—CH₂—(D)-Chg-Pyr-NH—CH₂-2-[4-am-(OH)]-thiaz |
| 109. | EtOOC—CH₂—(D)-Chg-Pyr-NH—CH₂-2-[4-am-(OH)]-thiaz |
| 110. | EtOOC—CH₂—(D)-Chg-Dep-NH—CH₂-2-[4-am-(OH)]-thiaz |
| 111. | nPrOOC—CH₂—(D)-Chg-Pyr-NH—CH₂-2-[4-am-(OH)]-thiaz |
| 112. | iPrOOC—CH₂—(D)-Chg-Pyr-NH—CH₂-2-[4-am-(OH)]-thiaz |
| 113. | nBuOOC—CH₂—(D)-Chg-Pyr-NH—CH₂-2-[4-am-(OH)]-thiaz |
| 114. | tBuOOC—CH₂—(D)-Chg-Pyr-NH—CH₂-2-[4-am-(OH)]-thiaz |
| 115. | tBuOOC—CH₂—(D)-Chg-Dep-NH—CH₂-2-[4-am-(OH)]-thiaz |
| 116. | iBuOOC—CH₂—(D)-Chg-Pyr-NH—CH₂-2-[4-am-(OH)]-thiaz |
| 117. | nPentOOC—CH₂—(D)-Chg-Pyr-NH—CH₂-2-[4-am-(OH)]-thiaz |
| 118. | iPentOOC—CH₂—(D)-Chg-Pyr-NH—CH₂-2-[4-am-(OH)]-thiaz |
| 119. | nHexOOC—CH₂—(D)-Chg-Dep-NH—CH₂-2-[4-am-(OH)]-thiaz |
| 120. | neoPentOOC—CH₂—(D)-Chg-Pyr-NH—CH₂-2-[4-am-(OH)]-thiaz |
| 121. | nHexOOC—CH₂—(D)-Chg-Pyr-NH—CH₂-2-[4-am-(OH)]-thiaz |
| 122. | cHex-OC—CH₂—(D)-Chg-Pyr-NH—CH₂-2-[4-am-(OH)]-thiaz |
| 123. | nHeptOOC—CH₂—(D)-Chg-Pyr-NH—CH₂-2-[4-am-(OH)]-thiaz |
| 124. | nOctOOC—CH₂—(D)-Chg-Pyr-NH—CH₂-2-[4-am-(OH)]-thiaz |
| 125. | cOctOOC—CH₂—(D)-Chg-Pyr-NH—CH₂-2-[4-am-(OH)]-thiaz |
| 126. | BnOOC—CH₂—(D)-Chg-Pyr-NH—CH₂-2-[4-am-(OH)]-thiaz |
| 127. | AdaOOC—CH₂—(D)-Chg-Pyr-NH—CH₂-2-[4-am-(OH)]-thiaz |
| 128. | cHex-CH₂OOC—CH₂—(D)-Chg-Pyr-NH—CH₂-2-[4-am-(OH)]-thiaz |
| 129. | CH₃—(CH₂)₁₀OOC—CH₂—(D)-Chg-Pyr-NH—CH₂-2-[4-am-(OH)]-thiaz |
| 130. | CH₃—(CH₂)₁₅OOC—CH₂—(D)-Chg-Pyr-NH—CH₂-2-[4-am-(OH)]-thiaz |
| 131. | AdaOOC—CH₂—(D)-Chg-Pyr-NH—CH₂-2-[4-am-(H)]-thiaz |
| 132. | cHex-CH₂OOC—CH₂—(D)-Chg-Pyr-NH—CH₂-2-[4-am-(H)]-thiaz |
| 133. | CH₃—(CH₂)₁₀OOC—CH₂—(D)-Chg-Pyr-NH—CH₂-2-[4-am-(H)]-thiaz |
| 134. | CH₃—(CH₂)₁₅OOC—CH₂—(D)-Chg-Pyr-NH—CH₂-2-[4-am-(H)]-thiaz |
| 135. | CH₃OOC—CH₂—(D)-Cha-Pyr-NH—CH₂-2-[4-am-(OH)]-thiaz |
| 136. | nPrOOC—CH₂—(D)-Cha-Pyr-NH—CH₂-2-[4-am-(OH)]-thiaz |
| 137. | nPrOOC—CH₂—(D)-Cha-Dep-NH—CH₂-2-[4-am-(OH)]-thiaz |
| 138. | nBuOOC—CH₂—(D)-Cha-Pyr-NH—CH₂-2-[4-am-(OH)]-thiaz |
| 139. | iBuOOC—CH₂—(D)-Cha-Pyr-NH—CH₂-2-[4-am-(OH)]-thiaz |
| 140. | nPentOOC—CH₂—(D)-Cha-Pyr-NH—CH₂-2-[4-am-(OH)]-thiaz |
| 141. | nPentOOC—CH₂—(D)-Cha-Dep-NH—CH₂-2-[4-am-(OH)]-thiaz |
| 142. | iPentOOC—CH₂—(D)-Cha-Pyr-NH—CH₂-2-[4-am-(OH)]-thiaz |
| 143. | nHeptOOC—CH₂—(D)-Cha-Pyr-NH—CH₂-2-[4-am-(OH)]-thiaz |
| 144. | nOctOOC—CH₂—(D)-Cha-Pyr-NH—CH₂-2-[4-am-(OH)]-thiaz |
| 145. | cOctOOC—CH₂—(D)-Cha-Pyr-NH—CH₂-2-[4-am-(OH)]-thiaz |
| 146. | BnOOC—CH₂—(D)-Cha-Pyr-NH—CH₂-2-[4-am-(OH)]-thiaz |
| 147. | BnOOC—CH₂—(D)-Cha-Dep-NH—CH₂-2-[4-am-(OH)]-thiaz |
| 148. | cHex-CH₂OOC—CH₂—(D)-Cha-Dep-NH—CH₂-2-[4-am-(H)]-thiaz |
| 149. | CH₃—(CH₂)₁₀OOC—CH₂—(D)-Cha-Dep-NH—CH₂-2-[4-am-(H)]-thiaz |
| 150. | CH₃—(CH₂)₁₅OOC—CH₂—(D)-Cha-Dep-NH—CH₂-2-[4-am-(H)]-thiaz |
| 151. | CH₃OOC—CH₂—(D)-Cha-Pyr-NH—CH₂-2-[4-am-(OMe)]-thiaz |
| 152. | nPrOOC—CH₂—(D)-Cha-Pyr-NH—CH₂-2-[4-am-(OMe)]-thiaz |
| 153. | EtOOC—CH₂—(D)-Cha-Pyr-NH—CH₂-2-[4-am-(OMe)]-thiaz |
| 154. | nBuOOC—CH₂—(D)-Cha-Pyr-NH—CH₂-2-[4-am-(OMe)]-thiaz |
| 155. | HOOC—CH₂—N—(CO₂CH₂ᶜHex)—(D)-Cha-Pyr-NH—CH₂-2-[4-am-(H)]-thiaz |
| 156. | HOOC—CH₂—N—(CO₂ᶜOct)-(D)-Cha-Pyr-NH—CH₂-2-[4-am-(H)]-thiaz |
| 157. | HOOC—CH₂—N—(CO₂ᶜHex)-(D)-Cha-Pyr-NH—CH₂-5-[2-am-(H)]-thioph |
| 158. | HOOC—CH₂—N—(CO₂CH₂ᶜHex)-(D)-Cha-Pyr-NH—CH₂-5-[2-am-(H)]-thioph |
| 159. | HOOC—CH₂—N—(CO₂ᶜOct)-(D)-Cha-Pyr-NH—CH₂-5-[2-am-(H)]-thioph |
| 160. | HOOC—CH₂—N—(CO₂ᶜHex)-(D)-Chg-Pyr-NH—CH₂-5-[3-am-(H)]-thioph |
| 161. | HOOC—CH₂—N—(CO₂CH₂ᶜHex)-(D)-Chg-Pyr-NH—CH₂-5-[3-am-(H)]-thioph |
| 162. | HOOC—CH₂—N—(CO₂ᶜOct)-(D)-Chg-Pyr-NH—CH₂-5-[3-am-(H)]-thioph |
| 163. | CH₃OOC—CH₂—(D)-Cha-Pyr-NH—CH₂-2-[5-am-(OH)]-thiaz |
| 164. | EtOOC—CH₂—(D)-Cha-Pyr-NH—CH₂-2-[5-am-(OH)]-thiaz |
| 165. | nPrOOC—CH₂—(D)-Cha-Pyr-NH—CH₂-2-[5-am-(OH)]-thiaz |
| 166. | nPrOOC—CH₂—(D)-Cha-Dep-NH—CH₂-2-[5-am-(OH)]-thiaz |
| 167. | CH₃OOC—CH₂—(D)-Chg-Pyr-NH—CH₂-5-3-Me-[2-am-(OH)]-thioph |
| 168. | EtOOC—CH₂—(D)-Chg-Pyr-NH—CH₂-5-3-Me-[2-am-(OH)]-thioph |
| 169. | nPrOOC—CH₂—(D)-Chg-Pyr-NH—CH₂-5-3-Me-[2-am-(OH)]-thioph |
| 170. | CH₃OOC—CH₂—(D)-Chg-Pyr-NH—CH₂-5-4-Me-[3-am-(OH)]-thioph |
| 171. | EtOOC—CH₂—(D)-Chg-Pyr-NH—CH₂-5-4-Me-[3-am-(OH)]-thioph |

-continued

| | |
|---|---|
| 172. | nPrOOC—CH₂—(D)-Chg-Pyr-NH—CH₂-5-4-Me-[3-am-(OH)]-thioph |
| 173. | cHex-CH₂OOC—CH₂—(D)-Chg-Pro-NH—CH₂-5-[2-am-(OH)]-thioph |
| 174. | AdaOOC—CH₂—(D)-Chg-Pro-NH—CH₂-5-[2-am-(H)]-thioph |
| 175. | cHex-CH₂OOC—CH₂—(D)-Chg-Pro-NH—CH₂-5-[2-am-(H)]-thioph |
| 176. | CH₃—(CH₂)₁₀OOC—CH₂—(D)-Chg-Pro-NH—CH₂-5-[2-am-(OH)]-thioph |
| 177. | CH₃—(CH₂)₁₅OOC—CH₂—(D)-Chg-Pro-NH—CH₂-5-[2-am-(OH)]-thioph |
| 178. | CH₃—(CH₂)₁₀OOC—CH₂—(D)-Chg-Pro-NH—CH₂-5-[2-am-(H)]-thioph |
| 179. | CH₃—(CH₂)₁₅OOC—CH₂—(D)-Chg-Pro-NH—CH₂-5-[2-am-(H)]-thioph |
| 180. | cHex-CH₂OOC—CH₂—(D)-Chg-Pro-NH—CH₂-5-[3-am-(OH)]-thioph |
| 181. | AdaOOC—CH₂—(D)-Chg-Pro-NH—CH₂-5-[3-am-(H)]-thioph |
| 182. | cHex-CH₂OOC—CH₂—(D)-Chg-Pro-NH—CH₂-5-[3-am-(H)]-thioph |
| 183. | CH₃—(CH₂)₁₀OOC—CH₂—(D)-Chg-Pro-NH—CH₂-5-[3-am-(OH)]-thioph |
| 184. | CH₃—(CH₂)₁₅OOC—CH₂—(D)-Chg-Pro-NH—CH₂-5-[3-am-(OH)]-thioph |
| 185. | CH₃—(CH₂)₁₀OOC—CH₂—(D)-Chg-Pro-NH—CH₂-5-[3-am-(H)]-thioph |
| 186. | CH₃—(CH₂)₁₅OOC—CH₂—(D)-Chg-Pro-NH—CH₂-5-[3-am-(H)]-thioph |
| 187. | cHex-CH₂OOC—CH₂—(D)-Cha-Pro-NH—CH₂-2-[4-am-(OH)]-thiaz |
| 188. | AdaOOC—CH₂—(D)-Cha-Pro-NH—CH₂-2-[4-am-(H)]-thiaz |
| 189. | cHex-CH₂OOC—CH₂—(D)-Cha-Pro-NH—CH₂-2-[4-am-(H)]-thiaz |
| 190. | CH₃—(CH₂)₁₀OOC—CH₂—(D)-Cha-Pro-NH—CH₂-2-[4-am-(OH)]-thiaz |
| 191. | CH₃—(CH₂)₁₅OOC—CH₂—(D)-Cha-Pro-NH—CH₂-2-[4-am-(OH)]-thiaz |
| 192. | CH₃—(CH₂)₁₀OOC—CH₂—(D)-Cha-Pro-NH—CH₂-2-[4-am-(H)]-thiaz |
| 193. | CH₃—(CH₂)₁₅OOC—CH₂—(D)-Cha-Pro-NH—CH₂-2-[4-am-(H)]-thiaz |
| 194. | cPent-OOC—CH₂—(D)-Chg-Pro-NH—CH₂-5-[2-am-(OH)]-thioph |
| 195. | cPent-CH₂—OOC—CH₂—(D)-Chg-Pro-NH—CH₂-5-[2-am-(OH)]-thioph |
| 196. | cHex-OOC—CH₂—(D)-Chg-Pro-NH—CH₂-5-[2-am-(OH)]-thioph |
| 197. | cPent-OOC—CH₂—(D)-Chg-Pro-NH—CH₂-5-[2-am-(OH)]-thioph |
| 198. | cPent-CH₂—OOC—CH₂—(D)-Cha-Pro-NH—CH₂-5-[2-am-(OH)]-thioph |
| 199. | cHex-OOC—CH₂—(D)-Cha-Pro-NH—CH₂-5-[2-am-(OH)]-thioph |
| 200. | cHex-CH₂—OOC—CH₂—(D)-Cha-Pro-NH—CH₂-5-[2-am-(OH)]-thioph |
| 201. | cPent-OOC—CH₂—(D)-Chg-Pro-NH—CH₂-5-[3-am-(OH)]-thioph |
| 202. | cPent-CH₂—OOC—CH₂—(D)-Chg-Pro-NH—CH₂-5-[3-am-(OH)]-thioph |
| 203. | cHex-OOC—CH₂—(D)-Chg-Pro-NH—CH₂-5-[3-am-(OH)]-thioph |
| 204. | cPent-OOC—CH₂—(D)-Cha-Pro-NH—CH₂-5-[3-am-(OH)]-thioph |
| 205. | cPent-CH₂—OOC—CH₂—(D)-Cha-Pro-NH—CH₂-5-[3-am-(OH)]-thioph |
| 206. | cHex-OOC—CH₂—(D)-Cha-Pro-NH—CH₂-5-[3-am-(OH)]-thioph |
| 207. | cHex-CH₂—OOC—CH₂—(D)-Cha-Pro-NH—CH₂-5-[3-am-(OH)]-thioph |
| 208. | cPent-OOC—CH₂—(D)-Chg-Pro-NH—CH₂-2-[4-am-(OH)]-thiaz |
| 209. | cPent-CH₂—OOC—CH₂—(D)-Chg-Pro-NH—CH₂-2-[4-am-(OH)]-thiaz |
| 210. | cHex-OOC—CH₂—(D)-Chg-Pro-NH—CH₂-2-[4-am-(OH)]-thiaz |
| 211. | cPent-OOC—CH₂—(D)-Cha-Pro-NH—CH₂-2-[4-am-(OH)]-thiaz |
| 212. | cPent-CH₂—OOC—CH₂—(D)-Cha-Pro-NH—CH₂-2-[4-am-(OH)]-thiaz |
| 213. | cHex-OOC—CH₂—(D)-Cha-Pro-NH—CH₂-2-[4-am-(OH)]-thiaz |
| 214. | cHN₄C—CH₂—(D)-Cha-Pyr-NH—CH₂-2-[4-am-(OH)]-thiaz |
| 215. | cHN₄C—CH₂—(D)-Chg-Pyr-NH—CH₂-2-[4-am-(OH)]-thiaz |
| 216. | cHN₄C—CH₂—(D)-Cha-Pyr-NH—CH₂-5-[2-am-(OH)]-thioph |
| 217. | cHN₄C—CH₂—(D)-Chg-Pyr-NH—CH₂-5-[2-am-(OH)]-thioph |
| 218. | cHN₄C—CH₂—(D)-Cha-Pyr-NH—CH₂-5-[3-am-(OH)]-thioph |
| 219. | cHN₄C—CH₂—(D)-Chg-Pyr-NH—CH₂-5-[3-am-(OH)]-thioph |
| 220. | HONH—OC—CH₂—(D)-Chg-Pyr-NH—CH₂-2-[4-am-(OH)]-thiaz |
| 221. | HONH—OC—CH₂—(D)-Cha-Pyr-NH—CH₂-2-[4-am-(OH)]-thiaz |
| 222. | HONH—OC—CH₂—(D)-Chg-Pyr-NH—CH₂-5-[2-am-(OH)]-thioph |
| 223. | HONH—OC—CH₂—(D)-Cha-Pyr-NH—CH₂-5-[3-am-(OH)]-thioph |
| 224. | HONH—OC—CH₂—(D)-Chg-Pyr-NH—CH₂-5-[3-am-(OH)]-thioph |
| 225. | cHex-N(OH)—OC—CH₂—(D)-Cha-Pyr-NH—CH₂-2-[4-am-(OH)]-thiaz |
| 226. | cHex-N(OH)—OC—CH₂—(D)-Chg-Pyr-NH—CH₂-2-[4-am-(OH)]-thiaz |
| 227. | cHex-N(OH)—OC—CH₂—(D)-Cha-Pyr-NH—CH₂-5-[2-am-(OH)]-thioph |
| 228. | cHex-N(OH)—OC—CH₂—(D)-Chg-Pyr-NH—CH₂-5-[2-am-(OH)]-thioph |
| 229. | cHex-N(OH)—OC—CH₂—(D)-Cha-Pyr-NH—CH₂-5-[3-am-(OH)]-thioph |
| 230. | cHex-N(OH)—OC—CH₂—(D)-Chg-Pyr-NH—CH₂-5-[3-am-(OH)]-thioph |
| 231. | iPr-N(OH)—OC—CH₂—(D)-Cha-Pyr-NH—CH₂-2-[4-am-(OH)]-thiaz |
| 232. | iPr-N(OH)—OC—CH₂—(D)-Chg-Pyr-NH—CH₂-2-[4-am-(OH)]-thiaz |
| 233. | iPr-N(OH)—OC—CH₂—(D)-Cha-Pyr-NH—CH₂-5-[2-am-(OH)]-thioph |
| 234. | iPr-N(OH)—OC—CH₂—(D)-Chg-Pyr-NH—CH₂-5-[2-am-(OH)]-thioph |
| 235. | iPr-N(OH)—OC—CH₂—(D)-Cha-Pyr-NH—CH₂-5-[3-am-(OH)]-thioph |
| 236. | iPr-N(OH)—OC—CH₂—(D)-Chg-Pyr-NH—CH₂-5-[3-am-(OH)]-thioph |
| 237. | CH₃—N(OH)—OC—CH₂—(D)-Cha-Pyr-NH—CH₂-2-[4-am-(OH)]-thiaz |
| 238. | CH₃—N(OH)—OC—CH₂—(D)-Chg-Pyr-NH—CH₂-2-[4-am-(OH)]-thiaz |
| 239. | CH₃—N(OH)—OC—CH₂—(D)-Cha-Pyr-NH—CH₂-5-[2-am-(OH)]-thioph |
| 240. | CH₃—N(OH)—OC—CH₂—(D)-Chg-Pyr-NH—CH₂-5-[2-am-(OH)]-thioph |
| 241. | CH₃—N(OH)—OC—CH₂—(D)-Cha-Pyr-NH—CH₂-5-[3-am-(OH)]-thioph |
| 242. | CH₃—N(OH)—OC—CH₂—(D)-Chg-Pyr-NH—CH₂-5-[3-am-(OH)]-thioph |
| 243. | NH₂—O₂C—CH₂—(D)-Cha-Pyr-NH—CH₂-2-[4-am-(OH)]-thiaz |
| 244. | NH₂—O₂C—CH₂—(D)-Chg-Pyr-NH—CH₂-2-[4-am-(OH)]-thiaz |
| 245. | NH₂—O₂C—CH₂—(D)-Cha-Pyr-NH—CH₂-5-[2-am-(OH)]-thioph |
| 246. | NH₂—O₂C—CH₂—(D)-Chg-Pyr-NH—CH₂-5-[2-am-(OH)]-thioph |
| 247. | NH₂—O₂C—CH₂—(D)-Cha-Pyr-NH—CH₂-5-[3-am-(OH)]-thioph |
| 248. | NH₂—O₂C—CH₂—(D)-Chg-Pyr-NH—CH₂-5-[3-am-(OH)]-thioph |
| 249. | c(CH₂)₅N—O₂C—CH₂—(D)-Cha-Pyr-NH—CH₂-2-[4-am-(OH)]-thiaz |
| 250. | c(CH₂)₅N—O₂C—CH₂—(D)-Chg-Pyr-NH—CH₂-2-[4-am-(OH)]-thiaz |

-continued

| | |
|---|---|
| 251. | c(CH₂)₅N—O₂C—CH₂—(D)-Cha-Pyr-NH—CH₂-5-[2-am-(OH)]-thioph |
| 252. | c(CH₂)₅N—O₂C—CH₂—(D)-Chg-Pyr-NH—CH₂-5-[2-am-(OH)]-thioph |
| 253. | c(CH₂)₅N—O₂C—CH₂—(D)-Cha-Pyr-NH—CH₂-5-[3-am-(OH)]-thioph |
| 254. | c(CH₂)₅N—O₂C—CH₂—(D)-Chg-Pyr-NH—CH₂-5-[3-am-(OH)]-thioph |
| 255. | N—Me-4-Pip-O₂C—CH₂—(D)-Cha-Pyr-NH—CH₂-2-[4-am-(OH)]-thiaz |
| 256. | N—Me-4-Pip-O₂C—CH₂—(D)-Chg-Pyr-NH—CH₂-2-[4-am-(OH)]-thiaz |
| 257. | N—Me-4-Pip-O₂C—CH₂—(D)-Cha-Pyr-NH—CH₂-5-[2-am-(OH)]-thioph |
| 258. | N—Me-4-Pip-O₂C—CH₂—(D)-Chg-Pyr-NH—CH₂-5-[2-am-(OH)]-thioph |
| 259. | N—Me-4-Pip-O₂C—CH₂—(D)-Cha-Pyr-NH—CH₂-5-[3-am-(OH)]-thioph |
| 260. | N—Me-4-Pip-O₂C—CH₂—(D)-Chg-Pyr-NH—CH₂-5-[3-am-(OH)]-thioph |
| 261. | N—Me-4-Pip-O₂C—CH₂—(D)-Cha-Pyr-NH—CH₂-2-[4-am-(OH)]-thiaz |
| 262. | N—Me-4-Pip-O₂C—CH₂—(D)-Chg-Pyr-NH—CH₂-2-[4-am-(OH)]-thiaz |
| 263. | N—Me-4-Pip-O₂C—CH₂—(D)-Cha-Pyr-NH—CH₂-5-[2-am-(OH)]-thioph |
| 264. | N—Me-4-Pip-O₂C—CH₂—(D)-Chg-Pyr-NH—CH₂-5-[2-am-(OH)]-thioph |
| 265. | N—Me-4-Pip-O₂C—CH₂—(D)-Cha-Pyr-NH—CH₂-5-[3-am-(OH)]-thioph |
| 266. | N—Me-4-Pip-O₂C—CH₂—(D)-Chg-Pyr-NH—CH₂-5-[3-am-(OH)]-thioph |
| 267. | NH₂—CH₂—CH₂—(D)-Cha-Pyr-NH—CH₂-2-[4-am-(OH)]-thiaz |
| 268. | NH₂—CH₂—CH₂—(D)-Chg-Pyr-NH—CH₂-2-[4-am-(OH)]-thiaz |
| 269. | NH₂—CH₂—CH₂—(D)-Cha-Pyr-NH—CH₂-5-[2-am-(OH)]-thioph |
| 270. | NH₂—CH₂—CH₂—(D)-Chg-Pyr-NH—CH₂-5-[2-am-(OH)]-thioph |
| 271. | NH₂—CH₂—CH₂—(D)-Cha-Pyr-NH—CH₂-5-[3-am-(OH)]-thioph |
| 272. | NH₂—CH₂—CH₂—(D)-Chg-Pyr-NH—CH₂-5-[3-am-(OH)]-thioph |
| 273. | (CH₃)₂N—CH₂—CH₂—(D)-Cha-Pyr-NH—CH₂-2-[4-am-(OH)]-thiaz |
| 274. | (CH₃)₂N—CH₂—CH₂—(D)-Chg-Pyr-NH—CH₂-2-[4-am-(OH)]-thiaz |
| 275. | (CH₃)₂N—CH₂—CH₂—(D)-Cha-Pyr-NH—CH₂-5-[2-am-(OH)]-thioph |
| 276. | (CH₃)₂N—CH₂—CH₂—(D)-Chg-Pyr-NH—CH₂-5-[2-am-(OH)]-thioph |
| 277. | (CH₃)₂N—CH₂—CH₂—(D)-Cha-Pyr-NH—CH₂-5-[3-am-(OH)]-thioph |
| 278. | (CH₃)₂N—CH₂—CH₂—(D)-Chg-Pyr-NH—CH₂-5-[3-am-(OH)]-thioph |
| 279. | CH₃—NH—CH₂—CH₂—(D)-Cha-Pyr-NH—CH₂-2-[4-am-(OH)]-thiaz |
| 280. | CH₃—NH—CH₂—CH₂—(D)-Chg-Pyr-NH—CH₂-2-[4-am-(OH)]-thiaz |
| 281. | CH₃—NH—CH₂—CH₂—(D)-Cha-Pyr-NH—CH₂-5-[2-am-(OH)]-thioph |
| 282. | CH₃—NH—CH₂—CH₂—(D)-Chg-Pyr-NH—CH₂-5-[2-am-(OH)]-thioph |
| 283. | CH₃—NH—CH₂—CH₂—(D)-Cha-Pyr-NH—CH₂-5-[3-am-(OH)]-thioph |
| 284. | CH₃—NH—CH₂—CH₂—(D)-Chg-Pyr-NH—CH₂-5-[3-am-(OH)]-thioph |
| 285. | CH₃—SO₂—CH₂—CH₂—(D)-Cha-Pyr-NH—CH₂-2-[4-am-(OH)]-thiaz |
| 286. | CH₃—SO₂—CH₂—CH₂—(D)-Chg-Pyr-NH—CH₂-2-[4-am-(OH)]-thiaz |
| 287. | CH₃—SO₂—CH₂—CH₂—(D)-Cha-Pyr-NH—CH₂-5-[2-am-(OH)]-thioph |
| 288. | CH₃—SO₂—CH₂—CH₂—(D)-Chg-Pyr-NH—CH₂-5-[2-am-(OH)]-thioph |
| 289. | CH₃—SO₂—CH₂—CH₂—(D)-Cha-Pyr-NH—CH₂-5-[3-am-(OH)]-thioph |
| 290. | CH₃—SO₂—CH₂—CH₂—(D)-Chg-Pyr-NH—CH₂-5-[3-am-(OH)]-thioph |
| 291. | CH₃—O—CH₂—CH₂—(D)-Cha-Pyr-NH—CH₂-2-[4-am-(OH)]-thiaz |
| 292. | CH₃—O—CH₂—CH₂—(D)-Chg-Pyr-NH—CH₂-2-[4-am-(OH)]-thiaz |
| 293. | CH₃—O—CH₂—CH₂—(D)-Cha-Pyr-NH—CH₂-5-[2-am-(OH)]-thioph |
| 294. | CH₃—O—CH₂—CH₂—(D)-Chg-Pyr-NH—CH₂-5-[2-am-(OH)]-thioph |
| 295. | CH₃—O—CH₂—CH₂—(D)-Cha-Pyr-NH—CH₂-5-[3-am-(OH)]-thioph |
| 296. | CH₃—O—CH₂—CH₂—(D)-Chg-Pyr-NH—CH₂-5-[3-am-(OH)]-thioph |
| 297. | CH₃—NH—SO₂—CH₂—CH₂—(D)-Cha-Pyr-NH—CH₂-2-[4-am-(OH)]-thiaz |
| 298. | CH₃—NH—SO₂—CH₂—CH₂—(D)-Chg-Pyr-NH—CH₂-2-[4-am-(OH)]-thiaz |
| 299. | CH₃—NH—SO₂—CH₂—CH₂—(D)-Cha-Pyr-NH—CH₂-5-[2-am-(OH)]-thioph |
| 300. | CH₃—NH—SO₂—CH₂—CH₂—(D)-Chg-Pyr-NH—CH₂-5-[2-am-(OH)]-thioph |
| 301. | CH₃—NH—SO₂—CH₂—CH₂—(D)-Cha-Pyr-NH—CH₂-5-[3-am-(OH)]-thioph |
| 302. | CH₃—NH—SO₂—CH₂—CH₂—(D)-Chg-Pyr-NH—CH₂-5-[3-am-(OH)]-thioph |
| 303. | H₂N—SO₂—CH₂—CH₂—(D)-Cha-Pyr-NH—CH₂-2-[4-am-(OH)]-thiaz |
| 304. | H₂N—SO₂—CH₂—CH₂—(D)-Chg-Pyr-NH—CH₂-2-[4-am-(OH)]-thiaz |
| 305. | H₂N—SO₂—CH₂—CH₂—(D)-Cha-Pyr-NH—CH₂-5-[2-am-(OH)]-thioph |
| 306. | H₂N—SO₂—CH₂—CH₂—(D)-Chg-Pyr-NH—CH₂-5-[2-am-(OH)]-thioph |
| 307. | H₂N—SO₂—CH₂—CH₂—(D)-Cha-Pyr-NH—CH₂-5-[3-am-(OH)]-thioph |
| 308. | H₂N—SO₂—CH₂—CH₂—(D)-Chg-Pyr-NH—CH₂-5-[3-am-(OH)]-thioph |
| 309. | (CH₃)₃C—CO₂—CH₂—O₂C—CH₂—(D)-Cha-Pyr-NH—CH₂-2-[4-am-(OH)]-thiaz |
| 310. | (CH₃)₃C—CO₂—CH₂—O₂C—CH₂—(D)-Chg-Pyr-NH—CH₂-2-[4-am-(OH)]-thiaz |
| 311. | (CH₃)₃C—CO₂—CH₂—O₂C—CH₂—(D)-Cha-Pyr-NH—CH₂-5-[2-am-(OH)]-thioph |
| 312. | (CH₃)₃C—CO₂—CH₂—O₂C—CH₂—(D)-Chg-Pyr-NH—CH₂-5-[2-am-(OH)]-thioph |
| 313. | (CH₃)₃C—CO₂—CH₂—O₂C—CH₂—(D)-Cha-Pyr-NH—CH₂-5-[3-am-(OH)]-thioph |
| 314. | (CH₃)₃C—CO₂—CH₂—O₂C—CH₂—(D)-Chg-Pyr-NH—CH₂-5-[3-am-(OH)]-thioph |
| 315. | (CH₃)₃C—CO₂—CH(CH₃)—O₂C—CH₂—(D)-Cha-Pyr-NH—CH₂-2-[4-am-(OH)]-thiaz |
| 316. | (CH₃)₃C—CO₂—CH(CH₃)—O₂C—CH₂—(D)-Chg-Pyr-NH—CH₂-2-[4-am-(OH)]-thiaz |
| 317. | (CH₃)₃C—CO₂—CH(CH₃)—O₂C—CH₂—(D)-Cha-Pyr-NH—CH₂-5-[2-am-(OH)]-thioph |
| 318. | (CH₃)₃C—CO₂—CH(CH₃)—O₂C—CH₂—(D)-Chg-Pyr-NH—CH₂-5-[2-am-(OH)]-thioph |
| 319. | (CH₃)₃C—CO₂—CH(CH₃)—O₂C—CH₂—(D)-Cha-Pyr-NH—CH₂-5-[3-am-(OH)]-thioph |
| 320. | (CH₃)₃C—CO₂—CH(CH₃)—O₂C—CH₂—(D)-Chg-Pyr-NH—CH₂-5-[3-am-(OH)]-thioph |
| 321. | cHex-O—CO₂—CH₂—O₂C—CH₂—(D)-Cha-Pyr-NH—CH₂-2-[4-am-(OH)]-thiaz |
| 322. | cHex-O—CO₂—CH₂—O₂C—CH₂—(D)-Chg-Pyr-NH—CH₂-2-[4-am-(OH)]-thiaz |
| 323. | cHex-O—CO₂—CH₂—O₂C—CH₂—(D)-Cha-Pyr-NH—CH₂-5-[2-am-(OH)]-thioph |
| 324. | cHex-O—CO₂—CH₂—O₂C—CH₂—(D)-Chg-Pyr-NH—CH₂-5-[2-am-(OH)]-thioph |
| 325. | cHex-O—CO₂—CH₂—O₂C—CH₂—(D)-Cha-Pyr-NH—CH₂-5-[3-am-(OH)]-thioph |
| 326. | cHex-O—CO₂—CH₂—O₂C—CH₂—(D)-Chg-Pyr-NH—CH₂-5-[3-am-(OH)]-thioph |
| 327. | cHex-O—CO₂—CH(CH₃)—O₂C—CH₂—(D)-Cha-Pyr-NH—CH₂-2-[4-am-(OH)]-thiaz |
| 328. | cHex-O—CO₂—CH(CH₃)—O₂C—CH₂—(D)-Chg-Pyr-NH—CH₂-2-[4-am-(OH)]-thiaz |
| 329. | cHex-O—CO₂—CH(CH₃)—O₂C—CH₂—(D)-Cha-Pyr-NH—CH₂-5-[2-am-(OH)]-thioph |

-continued

| | |
|---|---|
| 330. | cHex-O—CO₂—CH(CH₃)—O₂C—CH₂—(D)-Chg-Pyr-NH—CH₂-5-[2-am-(OH)]-thioph |
| 331. | cHex-O—CO₂—CH(CH₃)—O₂C—CH₂—(D)-Cha-Pyr-NH—CH₂-5-[3-am-(OH)]-thioph |
| 332. | cHex-O—CO₂—CH(CH₃)—O₂C—CH₂—(D)-Chg-Pyr-NH—CH₂-5-[3-am-(OH)]-thioph |
| 333. | cHex-OCO—C(CH₃)₂—(D)-Cha-Pyr-NH—CH₂-2-[4-am-(OH)]-thiaz |
| 334. | cHex-OCO—C(CH₃)₂—(D)-Chg-Pyr-NH—CH₂-2-[4-am-(OH)]-thiaz |
| 335. | cHex-OCO—C(CH₃)₂—(D)-Cha-Pyr-NH—CH₂-5-[2-am-(OH)]-thioph |
| 336. | cHex-OCO—C(CH₃)₂—(D)-Chg-Pyr-NH—CH₂-5-[2-am-(OH)]-thioph |
| 337. | cHex-OCO—C(CH₃)₂—(D)-Cha-Pyr-NH—CH₂-5-[3-am-(OH)]-thioph |
| 338. | cHex-OCO—C(CH₃)₂—(D)-Chg-Pyr-NH—CH₂-5-[3-am-(OH)]-thioph |
| 339. | C₂H₅—O—CO—C(CH₃)₂—(D)-Cha-Pyr-NH—CH₂-2-[4-am-(OH)]-thiaz |
| 340. | C₂H₅—O—CO—C(CH₃)₂—(D)-Chg-Pyr-NH—CH₂-2-[4-am-(OH)]-thiaz |
| 341. | C₂H₅—O—CO—C(CH₃)₂—(D)-Cha-Pyr-NH—CH₂-5-[2-am-(OH)]-thioph |
| 342. | C₂H₅—O—CO—C(CH₃)₂—(D)-Chg-Pyr-NH—CH₂-5-[2-am-(OH)]-thioph |
| 343. | C₂H₅—O—CO—C(CH₃)₂—(D)-Cha-Pyr-NH—CH₂-5-[3-am-(OH)]-thioph |
| 344. | C₂H₅—O—CO—C(CH₃)₂—(D)-Chg-Pyr-NH—CH₂-5-[3-am-(OH)]-thioph |

LIST OF ABBREVIATIONS

| | |
|---|---|
| Adaala: | adamantylalanine |
| Adagly: | adamantylglycine |
| AIBN: | azobisisobutyronitrile |
| Ac: | acetyl |
| Ala: | alanine |
| am: | amidino |
| Asp: | aspartic acid |
| Aze: | azetidinecarboxylic acid |
| Bn: | benzyl |
| Boc: | tert-butyloxycarbonyl |
| Bu: | butyl |
| c-pent: | cyclopentyl |
| Cbz: | benzyloxycarbonyl |
| C(CH₂)₅N—: | N-piperidinyl |
| Cha: | cyclohexylalanine |
| Chea: | cycloheptylalanine |
| Cheg: | cycloheptylglycine |
| CHN₄C—: | tetrazolyl-(3-tetrazolyl- or 5-tetrazolyl) |
| Chg: | cyclohexylglycine |
| Cog: | cyclooctylglycine |
| Cpa: | cyclopentylalanine |
| Cpg: | cyclopentylglycine |
| TLC: | thin layer chromatography |
| DCC: | dicyclohexylcarbodiimide |
| Dch: | dicyclohexylalanine |
| Dcha: | dicyclohexylamine |
| DCM: | dichloromethane |
| Dep: | 4,5-dehydropipecolic acid |
| DMF: | dimethylformamide |
| DIPEA: | diisopropylethylamine |
| Dpa: | diphenylalanine |
| Et: | ethyl |
| Eq: | equivalents |
| Gly: | glycine |
| fur: | furan |
| ham: | hydroxyamidino |
| HOSucc: | hydroxysuccinimide |
| HPLC: | high performance liquid chromatograpy |
| iPr: | isopropyl |
| Me: | methyl |
| MPLC: | medium pressure liquid chromatography |
| MTBE: | methyl tert-butyl ether |
| NBS: | N-bromosuccinimide |
| N—Me-4-Pip-OH: | N-methyl-4-piperidinyl alcohol |
| Nog: | norbornylglycine |
| Oxaz: | oxazole |
| Ph: | phenyl |
| Phe: | phenylalanine |
| Pic: | pipecolic acid |
| PPA: | propylphosphonic anhydride |
| Pro: | proline |
| Py: | pyridine |
| Pyr: | 3,4-dehydroproline |
| pyraz: | pyrazole |
| pyrr: | rrole |

-continued

| | |
|---|---|
| RT: | room temperature |
| RP-18 | reversed phase C-18 |
| t: | tertiary |
| tBu: | tertiary butyl |
| tert: | tertiary |
| TBAB: | tetrabutylammonium bromide |
| TEA: | triethylamine |
| TFA: | trifluoroacetic acid |
| TFAA: | trifluoroacetic anhydride |
| thiaz: | thiazole |
| thioph: | thiophene |
| TOTU: | O-[cyano(ethoxycarbonyl)methyleneamino]-N,N,N',N'-tetramethyluronium tetrafluoroborate |
| Z: | benzyloxycarbonyl |
| ⁿPent: | n-pentyl |
| neoPent: | neopentyl (2,2-dimethyl-1-propyl) |
| nHex: | n-hexyl |
| cHex: | cyclohexyl |
| nOct: | n-octyl |
| O-p-Me-Bn: | p-methylbenzyloxy |
| MeO-tetraethoxy: | radical from tetraethylene glycol monomethyl ether |

The definitions for the individual substituents in the description and the claims are as follows:

The term "cycloalkyl" as such or as part of another substituent comprises saturated, cyclic hydrocarbon groups which contain the stated number of carbon atoms and in which up to two $CH_2$ groups may be replaced by oxygen, sulfur or nitrogen atoms. $C_{3-8}$-Cycloalkyl refers to saturated alicyclic rings having 3 to 8 C atoms such as, for example, cyclopropyl, cyclobutyl, cyclopentyl, cyclohexyl, 4-methyl-cyclohexyl, cyclohexylmethyl, cycloheptyl or cyclooctyl, pyrrolidinyl, piperidinyl, morpholinyl. Substituted cyclic hydrocarbons without heteroatoms are preferred.

The term "alkyl" as such or as part of another substituent means a linear or branched alkyl chain radical of the length stated in each case, which may be saturated or unsaturated and in which up to five $CH_2$ groups may be replaced by oxygen, sulfur or nitrogen atoms. In the latter case, the heteroatoms are separated from one another by at least two carbon atoms. Thus, $C_{1-4}$-alkyl means, for example, methyl, ethyl, 1-propyl, 2-propyl, 2-methyl-2-propyl, 2-methyl-1-propyl, 1-butyl, 1-but-2-enyl, 2-butyl, $C_{1-6}$-alkyl for example $C_{1-4}$-alkyl, 1-pentyl, 2-pentyl, 3-pentyl, 1-hexyl, 2-hexyl, 3-hexyl, 4-methyl-1-pentyl or 3,3-dimethylbutyl. $C_{1-8}$-Alkyl means in addition to the radicals stated for $C_{1-4}$-alkyl for example $C_{1-6}$-alkyl, heptyl, 2-(2-methoxy-ethoxy)ethyl or octyl.

Preferred are linear or branched saturated alkyl radicals without heteroatoms.

The term "alkoxy" as such or as part of another substituent means a linear or branched alkyl chain radical of the length stated in each case, which may be saturated or unsaturated and is linked via an oxygen atom to the parent compound in each case. Thus, $C_{1-4}$-alkoxy means, for example, methoxy, ethoxy, 1-propoxy, 2-propoxy, 2-methyl-2-propoxy, 2-methyl-1-propoxy, 1-butoxy, 2-butoxy.

The term "aryl" as such or as part of another substituent includes mono-, bi- or tricyclic aromatic hydrocarbons such as phenyl, naphthyl, tetralinyl, indenyl, fluorenyl, indanyl, an thracenyl, phenanthrenyl.

The compounds of the formula I may exist as such or in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid and acetylglycine.

The novel compounds of the formula I can be employed for the following indications:
disorders whose pathomechanism is based directly or indirectly on the proteolytic effect of thrombin,
disorders whose pathomechanism is based on the thrombin-dependent activation of receptors and signal transductions,
disorders associated with stimulation [e.g. by PAI-1, PDGF (platelet derived growth factor), P-selectin, ICAM-1, tissue factor] or inhibition (e.g. NO synthesis in smooth muscle cells) of the expression of genes in body cells,
disorders based on the mitogenic effect of thrombin,
disorders based on a thrombin-dependent change in the contractility and permeability of epithelial cells (e.g. vascular endothelial cells),
thrombin-dependent thromboembolic events such as deep vein thrombosis, pulmonary embolism, myocardial or cerebral infarct, atrial fibrillation, bypass occlusion,
disseminated intravascular coagulation (DIC),
reocclusion and for reducing the reperfusion time on comedication with thrombolytics such as streptokinase, urokinase, prourokinase, t-PA, APSAC, plasminogen activators from the salivary glands of animals, and the recombinant and mutated forms of all these substances,
the occurrence of early reocclusion and late restenosis after PTCA,
thrombin-dependent proliferation of smooth muscle cells,
accumulation of active thrombin in the CNS (e.g. in Alzheimer's disease),
tumor growth, and to counter the adhesion and metastasis of tumor cells.

The novel compounds can be employed in particular for the therapy and prophylaxis of thrombin-dependent thromboembolic events such as deep vein thromboses, pulmonary embolisms, myocardial or cerebral infarcts and unstable angina, also for the therapy of disseminated intravascular coagulation (DIC). They are further suitable for combination therapy with thrombolytics such as streptokinase, urokinase, prourokinase, t-PA, APSAC and other plasminogen activators for reducing the reperfusion time and increasing the reocclusion time.

Further preferred areas of use are to prevent thrombin-dependent early reocclusion and late restenosis after percutaneous transluminal coronary angioplasty, to prevent thrombin-induced proliferation of smooth muscle cells, to prevent the accumulation of active thrombin in the CNS (e.g. in Alzheimer's diseases), to control tumors and to prevent mechanisms which lead to adhesion and metastasis of tumor cells.

The novel compounds can be administered orally in a conventional way. Administration can also take place with vapors or sprays through the nasopharyngeal space.

The dosage depends on the age, condition and weight of the patient and on the mode of administration. As a rule, the daily dose of active substance per person is between about 10 and 2000 mg on oral administration. This dose can be given in 2 to 4 single doses or once a day as slow-release form.

The novel compounds can be used in conventional solid or liquid pharmaceutical forms, for example as uncoated or (film-)coated tablets, capsules, powders, granules, solutions or sprays. These are produced in a conventional way. The active substances can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain from 0.1 to 99% by weight of the active substance.

EXPERIMENTAL PART

Pharmacological Tests

The rate of absorption of medicines administered orally from the gastrointestinal tract (GIT) is an essential factor in relation to the bioavailability of the medicine. A good rate of absorption is a precondition for high bioavailability.

Several in vitro models are available for studying intestinal absorption. Thus, the human colon adenocarcinoma cell lines HT-29, Caco-2 and T84 are routinely employed to investigate various intestinal transport processes (Madara et al., *Am. J. Physiol.* 1988, 254: G416–G423; K. L. Audus et al., *Pharm. Res.* 1990, 7, 435–451). The IEC-18 cell line has also shown itself to be a suitable model for investigating the permeability of hydrophilic substances through the intestinal membrane (Ma et al., *J. Lab. Clin. Med.* 1992 120, 329–41; Duizer et al., *J. Contr. Rel.* 1997 49, 39–49).

For the transport experiments (for materials and methods, see R. T. Borchardt, P. L. Smith, G. Wilson, *Models for Assessing Drug Absorption and Metabolism*, $1^{st}$ edition, Plenum Press New York and London, 1996, chapter 2), the cells are cultivated on Transwell polycarbonate membranes for 17–24 days. The test chamber is arranged so that the membrane divides the apical from the basolateral compartment. Transport of the test substances from the apical side through the cell layer onto the basolateral side can be measured as a function of the pH gradient, for example apical (pH 6.0)→basolateral (pH 8.0).

After incubation of the cells with the test substance, samples are taken from the apical and basolateral sides after a defined time interval (e.g. 24 h). The content of test substance employed and any metabolites in each of the two compartments is determined by HPLC (comparison of retention times) and HPLC-MS (elucidation of metabolites) analyses. The transport rate is calculated.

It is possible on the basis of the results of these tests to divide test substances into the following categories:

+++: very good transport

++: good transport

+: moderate transport

The division of selected samples into said categories has been undertaken in the following table:

| Ex. No. | Transport |
|---|---|
| 2 | + |
| 10 | + |
| 11 | +++ |
| 21 | ++ |
| 25 | ++ |
| 29 | ++ |
| 33 | +++ |

Pharmacokinetics and Clotting Parameters in Rats

The test substances are dissolved in an isotonic salt solution immediately before administration to alert Sprague Dawley rats. The application volumes are 1 ml/kg for the intravenous bolus injection into the vein of the tail and 10 ml/kg for the oral administration which is conducted via a probang. If not indicated otherwise, blood samples are taken 1 hour after oral application of 21.5 ml·kg$^{-1}$ or intravenous application of 1.0 mg·kg$^{-1}$ of the test substance or the respective vehicle (control). Five minutes before the blood sample is taken, the animals are narcotized by i.p. application of a 25% urethane solution (dose 1 g·kg$^{-1}$ i.p.) in a physiological sodium chloride solution. The A. carotis is prepared and catheterized and blood samples (2 ml) in citrate vials (1.5 parts citrate plus 8.5 parts blood) are taken. Immediately after the samples are taken the ecarin clotting time (ECT) in the whole bood is determined. After the preparation of the plasma by centrifugation the plasma-thrombin time and the activated partial thromboplastin time (APTT) are determined by means of a coagulometer.

Clotting Parameters:

Ecarin clotting time (ECT): 100 µl citrate blood are incubated for 2 mins at 37° C. in a coagulometer (CL 8, Kugel-Typ, Bender & Hobein, München, BRD). After addition of 100 µl of preheated (37° C.) ecarin reagent (Pentapharm) the time taken for the formation of a fibrin clot is measured.

Activated thromboplastin time (APTT): 50 µl citrate plasma and 50 µl of the PTT reagent (Pathrombin, Behring) are mixed and incubated for 2 mins at 37° C. in a coagulometer (CL 8, Kugel-Typ, Bender & Hobein, München, BRD). After addition of 50 µl of preheated (37° C.) calcium chloride the time taken for the formation of a fibrin clot is measured.

Thrombin time (TT): 100 µl of plasma treated with citrate is incubated for 2 mins at 37° C. in a coagulometer (CL 8, Kugel-Typ, Bender & Hobein, München, BRD). After addition of 100 µl of preheated (37° C.) thrombin reagent (Boehringer Mannheim) the time taken for the formation of a fibrin clot is measured.

Pharamacokinetics and Clotting Parameters in Dogs

The test substances are dissolved in an isotonic salt solution immediately before administration to alert mongrels. The application volumes are 0.1 ml/kg for the intravenous bolus injection and 1 ml/kg for the oral application which is conducted via a probang. Before as well as 5, 10, 20, 30, 45, 60, 90, 120, 180, 240, 300, 360, (if necessary after 420, 480 min and 24 hours) after intravenous application of 1.0 ml/kg or before as well as 10, 20, 30, 60, 120, 180, 240, 300, 360, 480 mins and 24 hours after oral administration of 4.64 ml/kg, respectively, samples of venous blood (2 ml) are taken in citrate vials. Immediately after taking these samples, the ecarin clotting time (ECT) is determined in the whole blood. After separation of the plasma by centrifugation the plasma thrombin time and the activated partial thromboplastin time (APTT) are determined by means of a coagulometer.

In addition, the anti-F IIa-activity (ATU/ml) and the concentration of the substance by its anti-F IIa-activity in plasma is determined by means of a chromogenic (S-2238) thrombin assay whereby calibration curves with r-hirudin and the test substance were used.

The plasma concentration of the test substance is the basis for the calculation of the pharmacokinetic parameters: time of the maximum plasma concentration (T max), maximum plasma concentration; plasma half-life, $t_{0.5}$; area under the curve (AUC); absorbed part of the test substance (F).

Clotting Parameters:

Ecarin clotting time (ECT): 100 µl citrate blood are incubated for 2 mins at 37° C. in a coagulometer (CL 8, Kugel-Typ, Bender & Hobein, München, BRD). After addition of 100 µl of preheated (37° C.) ecarin reagent (Pentapharm) the time taken for the formation of a fibrin clot is measured.

Activated thromboplastin time (APTT) 50 µl citrate plasma and 50 µl of the PTT reagent (Pathrombin, Behring) are mixed and incubated for 2 mins at 37° C. in a coagulometer (CL 8, Kugel-Typ, Bender & Hobein, München, BRD). After addition of 50 µl of preheated (37° C.) calcium chloride the time taken for the formation of a fibrin clot is measured.

Thrombin time (TT): 100 µl of plasma treated with citrate is incubated for 2 mins at 37° C. in a coagulometer (CL 8, Kugel-Typ, Bender & Hobein, München, BRD). After addition of 100 µl of preheated (37° C.) thrombin reagent (Boehringer Mannheim) the time taken for the formation of a fibrin clot is measured.

The compounds of the formula I can be prepared as shown in schemes I–III.

The building blocks A, B, E and D are preferably assembled separately and employed in suitably protected form (see schemes I–III) using protective groups which are orthogonal in each case and are compatible with the synthetic method used (P or P*).

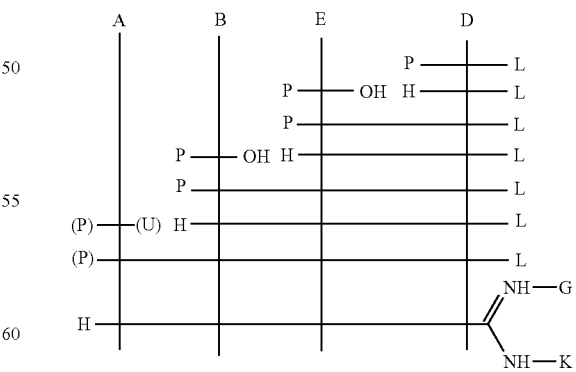

(P = protective group, (P) = protective group or H)

Scheme I describes the linear assembly of molecule I by elimination of protective groups from P-D-L (L equal to $CONH_2$, $CSNH_2$, CN), coupling of the amine H-D-L to the N-protected amino acid P-E-OH to give P-E-D-L, elimination of the N-terminal protective group to give H-E-D-L, coupling to the N-protected amino acid P-B-OH to give P-B-E-D-L, elimination of the protective group P to give H-B-E-D-L, subsequent coupling or alkylation with the optionally protected (P)-A-U building block (U=leaving group) or reductive alkylation with (P)-A'-U (U=aldehyde, ketone) or Michael addition with a suitable (P)-A"-C═C derivative to give (P)-A-B-E-D-L. If L is an amide function, this can be converted, at the protected stages in each case, by dehydration with trifluoroacetic anhydride into the corresponding nitrile function. Amidine syntheses for thienylamidine, furylamidine and thiazolylamidine compounds of structural type I starting from the corresponding carboxamides, nitrites, thiocarboxamides and hydroxyamidines are described in a number of patent applications (see, for example, WO 95/35309, WO 96/178860, WO 96/24609, WO 96/25426, WO 98/06741, WO 98/09950). Any protective groups still present are then eliminated.

Scheme II

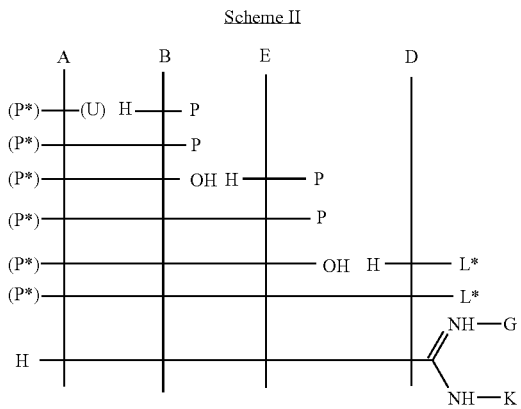

Scheme II describes the linear assembly of molecule I by coupling, alkylation, reductive amination or Michael addition of H-B-P onto appropriately suitable, optionally protected (P*)-A building blocks [(P*)-A-U (U=leaving group) or (P*)-A'-U (U=aldehyde, ketone) or (P*)-A"-C═C derivative] to give (P*)-A-B-P. Elimination of the C-terminal protective group to give (P*)-A-B-OH is followed by coupling to H-E-P to give (P*)-A-B-E-P, renewed elimination of the C-terminal protective group to give (P*)-A-B-E-OH and coupling to H-D-L* (L* equal to $CONH_2$, $CSNH_2$, CN, C(═NH)NH—R*; R* equal to hydrogen atom or protective group) to give (P*)-A-B-E-D-L. Reaction of this intermediate to give the final product takes place in analogy to scheme I. Synthesis of the alkoxy- or aryloxyamidines (G═OR) takes place by reacting the appropriate imino thioester salts with O-substituted hydroxylamine derivatives. P is then introduced by transesterification or starting from the free acid. To synthesize the oxadiazolones (G and K together form a COO group), in particular the 3-substituted 1,2,4-oxadiazol-5-ones, the appropriate amide oximes are reacted with carbonic acid derivatives such as, for example, phosgene, di- and triphosgene, carbonyldiimidazole or chloroformic esters with addition of bases (e.g. NaOH, pyridine, tertiary amines) (R. E. Bolton et al., Tetrahedron Lett. 1995, 36, 4471; K. Rehse, F. Brehme, Arch. Pharm. Med. Chem. 1998, 331, 375).

Scheme III

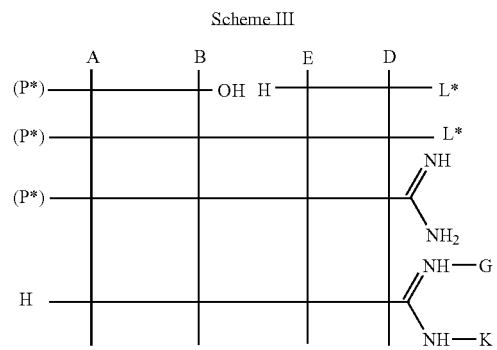

Scheme III describes a very efficient way for preparing the compounds I by a convergent synthesis. The appropriately protected building blocks (P*)-A-B-D-B-OH and H-E-D-L or H-E-D-L are coupled together and the resulting intermediates (P*)-A-B-D-B-E-D-L and (P*)-A-B-D-B-E-D-L scheme I are reacted to give the final product.

The N-terminal protective groups employed are Boc, Cbz or Fmoc, and C-terminal protective groups are methyl, tert-butyl and benzyl esters. Amidine protective groups are preferably Boc and Cbz. If the intermediates contain olefinic double bonds, protective groups eliminated by hydrogenolysis are unsuitable.

The required coupling reactions and the conventional reactions for introducing and eliminating protective groups are carried out under the standard conditions of peptide chemistry (see M. Bodanszky, A. Bodanszky "The Practice of Peptide Synthesis", $2^{nd}$ edition, Springer Verlag Heidelberg, 1994).

Boc protective groups are eliminated using dioxane/HCl, diethyl ether/HCl, dichloromethane/HCl or TFA/DCM, Cbz protective groups are eliminated by hydrogenolysis or with HF, Fmoc protective groups are eliminated with piperidine. Ester functions are hydrolyzed with LiOH in an alcoholic solvent or in dioxane/water. TFA or dioxane/HCl is used to cleave t-butyl esters.

The reactions were monitored by TLC, normally using the following mobile phases:

| | | |
|---|---|---|
| A. | DCM/MeOH | 95:5 |
| B. | DCM/MeOH | 9:1 |
| C. | DCM/MeOH | 8:2 |
| D. | DCM/MeOH/50% HOAc | 40:10:5 |
| E. | DCM/MeOH/50% HOAc | 35:15:5 |
| F. | cyclohexane/EA | 1:1 |

Where separations by column chromatography are mentioned, these were separations on silica gel using the above-mentioned mobile phases.

Reversed phase HPLC separations were carried out with acetonitrile/water and HOAc buffer.

The starting compounds can be prepared by the following methods:

The building blocks A employed for the alkylation are, for example, tert-butyl α-bromoacetate, adamantyl α-bromoacetate, tert-butyl β-bromopropionate, tert-butyl α-bromopropionate, tert-butyl α-bromobutyrate, 2,3-dimethyl-2-butyl α-bromoacetate, THP-protected bromoethanol, N-tert-butyl-α-bromoacetamide and N,N-diethyl-α-bromoacetamide. The tert-butyl esters mentioned are prepared in analogy to G.

Uray, W. Lindner, Tetrahedron 1988, 44, 4357–4362, unless they can be purchased. The bromoacetic esters not commercially available were prepared by reacting bromoacetyl bromide with the appropriate alcohols, adding pyridine as base.

B building Blocks:

A wide variety of possibilities for the general and specific synthesis of amino acids are available in the literature. A review thereof is to be found, inter alia, in volume E16d/part 1 of Houben-Weyl, pp. 406 et seq.

Precursors which are frequently employed were diphenylmethyleneglycine ethyl ester, diethyl acetamidomalonate and ethyl isocyanoacetate.

Various glycine and alanine derivatives were prepared, for example, starting from ethyl isocyanoacetate and an appropriate ketone or aldehyde (see H.-J. Prätorius, J. Flossdorf, M.-R. Kula Chem. Ber. 1975, 108, 3079).

The syntheses of cyclooctylglycine, 2-norbornylglycine, adamantylalanine, g-methylcyclohexylalanine, 4-isopropyl-cyclohex-1-ylalanine, 4-methylcyclohex-1-ylalanine and 4-methylcyclohex-1-ylglycine were carried out via the corresponding ethyl 2-formylaminoacrylates (U. Schöllkopf and R. Meyer, Liebigs Ann. Chem. 1977, 1174) starting from ethyl isocyanoacetate with the relevant carbonyl compounds cyclooctanone, 2-norbornanone, 1-formyladamantane, 1-formyl-1-methylcyclohexane, 1-formyl-4-isopropylcyclohexane, 1-formyl-4-methylcyclohexane and 4-methylcyclohexanone by the following general methods:

General Method for Synthesizing ethyl 2-formylaminoacrylates

A solution of 100 mmol of ethyl isocyanoacetate in 50 ml of THF was added dropwise to 100 mmol of potassium tert-butoxide in 150 ml of THF at 0 to −10° C. After 15 min, 100 mmol of the appropriate carbonyl compound in 50 ml of THF were added at the same temperature, the reaction mixture was allowed slowly to rise to RT, and the solvent was stripped off in a rotary evaporator. The residue was mixed with 50 ml of water, 100 ml of acetic acid and 100 ml of DCM, and the product was extracted with DCM. The DCM phase was dried over $Na_2SO_4$, and the solvent was stripped off in a rotary evaporator. The resulting products were almost pure but could, if necessary, be purified further by column chromatography on silica gel (mobile phases: ether/petroleum ether mixtures).

General method for amino acid hydrochlorides starting from the ethyl 2-formylaminoacrylates 100 mmol of the ethyl 2-formylaminoacrylates were hydrogenated with Pd/C (10%) and hydrogen in 200 ml of glacial acetic acid until the reaction was complete. The catalyst was then filtered off, the acetic acid was stripped off as far as possible in a rotary evaporator, and the residue was refluxed in 200 ml of 50% concentrated hydrochloric acid for 5 h. The hydrochloric acid was stripped off in a rotary evaporator, and the product was dried at 50° C. in vacuo and then washed several times with ether. The hydrochlorides resulted as pale-colored crystals.

25.0 g of cyclooctylglycine hydrochloride were obtained starting from 18.9 g (150 mmol) of cyclooctanone. 26.6 g of 2-norbornylglycine hydrochloride were obtained starting from 16.5 g (150 mmol) of 2-norbornanone. 26.0 g of adamantylalanine hydrochloride were obtained starting from 19.7 g (120 mmol) of 1-formyladamantane. 16.6 g of g-methylcyclohexylalanine hydrochloride were obtained starting from 12.6 g (100 mmol) of 1-formyl-1-methylcyclohexane. 25.9 g of 4-methylcyclohexylglycine hydrochloride were obtained starting from 16.8 g (150 mmol) of 4-methylcyclohexanone. 18 g of trans-4-methylcyclohex-1-ylalanine hydrochloride were-obtained starting from 15 g of trans-1-formyl-4-methylcyclohexane. 10 g of 3,3-dimethyl-cyclohex-1-ylalanine hydrochloride were obtained starting from 9 g of 3,3-dimethyl-1-formylcyclohexane.

The aldehyde 1-formyl-3,3-dimethylcyclohexane required for the synthesis was prepared by a method based on that of Moskal and Lensen (Rec. Trav. Chim. Pays-Bas 1987, 106, 137–141):

A solution of n-butyllithium in n-hexane (72 ml, 115 mmol) was added dropwise over the course of 10 min to a stirred solution of diethyl isocyanomethylphosphonate (17 ml, 105 mmol) in 280 ml of anhydrous diethyl ether at −60° C. The resulting suspension was then stirred at −60° C. for 15 min and, over the course of 10 min, a solution of 3,3-dimethylcyclohexanone (13 g, 105 mmol) in 100 ml of anhydrous diethyl ether was added, keeping the temperature below −45° C. The reaction mixture was allowed to reach 0° C. and, after stirring at this temperature for 90 min, 150–200 ml of 38% strength aqueous hydrochloric acid were cautiously added. The mixture was vigorously stirred at room temperature for 15 h to complete the hydrolysis. The organic phase was separated off and washed with 200 ml each of water, saturated sodium bicarbonate solution and saturated sodium chloride solution. It was dried over magnesium sulfate, filtered and concentrated in a rotary evaporator in order to remove the solvent. The resulting residue was employed without further purification as starting material for synthesizing the amino acid.

Boc-(D)-α-Methylcyclohexylalanine 3.4 g (12.2 mmol) of Boc-(D)-α-methyl-Phe-OH were hydrogenated in 100 ml of MeOH in the presence of 250 mg of 5% Rh on $Al_2O_3$ under 10 bar of hydrogen at 50° C. for 24 h. Filtration and stripping off the solvent resulted in 2.8 g of Boc-(D)-α-methyl-Cha-OH.

$^1$H-NMR (DMSO-$d_6$, δ in ppm): 12 (very broad signal, COOH); 1.7–0.8 (25 H: 1.35 (s, Boc), 1.30 (s, Me))

Boc-(3-Ph)-Pro-OH was synthesized in analogy to a method of J. Y. L. Chung et al. (J. Y. L. Chung et al. J. Org. Chem. 1990, 55, 270).

Preparation of Boc-(D,L)Dch-OH

Boc-(D,L)-Dpa-OH (1 mmol) was hydrogenated in 12 ml of MeOH together with catalytic amounts of 5% Rh/$Al_2O_3$ under 5 bar. Filtration and removal of the solvent in vacuo resulted in the product in quantitative yield.

Preparation of cycloheptylglycine, cyclopentylglycine, 4-isopropylcyclohexylglycine and 3,3-dimethylcyclohexylglycine These amino acids were prepared by reacting cycloheptanone, cyclopentanone, 4-isopropylcyclohexanone and 3,3-dimethylcyclohexanone, respectively, with ethyl isocyanoacetate by a method of H.-J. Prätorius (H.-J. Prätorius, J. Flossdorf, M. Kula, Chem. Ber. 1985, 108, 3079)

Preparation of H-D,L-Chea-OH 4.0 g of cycloheptylmethyl methanesulfonate (19.39 mmol), prepared from cycloheptylmethanol and methanesulfonyl chloride, were refluxed together with 4.9 g of diphenylmethyleneglycine ethyl ester (18.47 mmol), 8.9 g of dry, finely powdered potassium carbonate (64.65 mmol) and 1 g of tetrabutylammonium bromide (3 mmol) in 50 ml of dry acetonitrile under an inert gas atmosphere for 10 h. The potassium carbonate was then filtered off, the filtrate was evaporated to dryness, and the crude product was hydrolyzed directly with 20 ml of 2N hydrochloric acid in 40 ml of ethanol, stirring at RT for 1.5 h. The reaction solution was diluted and then benzophenone was extracted with ethyl acetate in the acidic range, and subsequently H-D,L-Chea-OEt was extracted with DCM in the alkaline range (pH=9), and the solution was dried over magnesium sulfate and concentrated in a rotary evaporator. Yield 3.7 g $\hat{=}$ 95% of theory.

Said amino acids were converted with di-tert-butyl dicarbonate in water/dioxane by conventional methods into the Boc-protected form in each case and subsequently recrystallized from ethyl acetate/hexane mixtures or purified by column chromatography on silica gel (mobile phases: ethyl acetate/petroleum ether mixtures).

The Boc-protected amino acids were employed as B building blocks as shown in scheme I.

Said amino acids as B building blocks were also in some cases converted into the corresponding benzyl esters and linked to the appropriately protected A building blocks. In the case of compounds with an N—H function which was still free, this was subsequently protected with a Boc group, the benzyl ester group was removed by hydrogenation and the building block A-B-OH was purified by crystallization, salt precipitation or column chromatography. This route is described by way of example for tBuOOC—CH$_2$-(Boc)(D)Cha-OH below.

Synthesis of D-cyclohexylalanine benzyl ester

A suspension of 100 g (481 mmol) of D-cyclohexylalanine hydrochloride, 104 g (962 mmol) of benzyl alcohol and 109.7 g (577 mmol) of p-toluenesulfonic acid monohydrate in 2200 ml of toluene was slowly heated to reflux with a water trap. Evolution of hydrogen chloride and dissolving of the suspension to give a clear solution were observed in the temperature range 80–90° C. When no further water separated out (about 4 h), 500 ml of toluene were distilled out, the reaction mixture was allowed to cool overnight, and the resulting residue was filtered off and washed twice with 1000 ml of hexane each time. The resulting residue (195 g) was then suspended in 2000 ml of dichloromethane and, after addition of 1000 ml of water, adjusted to pH 9–9.5 by gradual addition of 50% strength sodium hydroxide solution while stirring. The organic phase was separated off, washed twice with 500 ml of water each time, dried over sodium sulfate and filtered to remove desiccant, and the filtrate was concentrated, resulting in 115 g (94%) of the title product as a pale oil.

N-(tert-Butyloxycarbonylmethyl)-D-cyclohexylalanine benzyl ester 115 g (440 mmol) of D-cyclohexylalanine benzyl ester were dissolved in 2000 ml of acetonitrile and, at room temperature, 607.5 g (4.40 mol) of potassium carbonate and 94.3 g (484 mmol) of tert-butyl bromoacetate were added, and the mixture was stirred at this temperature for 3 days. Carbonate was filtered off, washing with acetonitrile, the mother liquor was concentrated (30° C., 20 mbar), the residue was taken up in 1000 ml of methyl tert-butyl ether, and the organic phase was extracted with 5% strength citric acid and saturated sodium bicarbonate solution. The organic phase was dried over sodium sulfate, filtered to remove desiccant and concentrated, and the resulting oil (168 g) was employed directly in the following reaction.

N-Boc-N-(tert-Butyloxycarbonylmethyl)-D-cyclohexylalanine benzyl ester

The oil (168 g, 447 mmol) obtained in the previous synthesis was dissolved in 1400 ml of acetonitrile and, after addition of 618 g (4.47 mol) of potassium carbonate powder and 107.3 g (492 mmol) of di-tert-butyl dicarbonate, stirred at room temperature for 6 days. The potassium carbonate was filtered off with suction, washing with about 1000 ml of acetonitrile, and the filtrate was concentrated. 230 g of the required product were obtained.

N-Boc-N-(tert-Butyloxycarbonylmethyl)-D-cyclohexylalanine cyclohexylammonium salt 115 g of N-Boc-N-(tert-butyloxycarbonylmethyl)-D-cyclohexylalanine benzyl ester were dissolved in 1000 ml of pure ethanol and hydrogenated in the presence of 9 g of 10% Pd on active carbon with hydrogen under atmospheric pressure at 25–30° C. for 2 h. Filtration and removal of the solvent in a rotary evaporator resulted in 100 g (260 mmol) of a yellow oil which was taken up in 1600 ml of acetone and heated to reflux. The heating bath was removed, and a solution of 27 g (273 mmol) of cyclohexylamine in acetone was quickly added through a dropping funnel. The required salt crystallized out on cooling the reaction mixture to room temperature. The solid was filtered off, washed with 200 ml of acetone and, for final purification, recrystallized once more from acetone. Drying of the residue in a vacuum oven at 30° C. resulted in 70.2 g of the required salt as a white powder.

N-Boc-N-(tert-Butyloxycarbonylmethyl)-D-cyclohexylglycine cyclohexylammonium salt was prepared in an analogous way from cyclohexylglycine as precursor.

N-Boc-N-(tert-Butyloxycarbonylethyl)-D-cyclohexylalanine cyclohexylammonium salt a) tert-Butyl 3-bromopropionate 16.64 g (109 mmol) of bromopropionic acid, 150 ml of condensed 2-methylpropene and 2 ml of concentrated sulfuric acid were placed at −30° C. under a countercurrent of nitrogen in a glass vessel suitable for an autoclave, tightly closed and stirred at room temperture for 72 h. For workup, the reaction vessel was again cooled to −30° C., and the reaction solution was cautiously poured into 200 ml of ice-cold saturated sodium bicarbonate solution. Excess 2-methylpropene was allowed to evaporate off with stirring, the residue was extracted three times with 50 ml of dichloromethane each time, the combined organic phases were dried over sodium sulfate, the desiccant was filtered off, and the solution was concentrated under waterpump vacuum. The oily residue was purified by column chromatography (mobile phase n-hexane, later n-hexane/diethyl ether 9:1). 18.86 g of the title compound were obtained.)

b) N-(tert-Butyloxycarbonylethyl)-D-cyclohexylalanine benzyl ester 49.4 g (189 mmol) of D-cyclohexylalanine benzyl ester were dissolved in 250 ml of acetonitrile and, after addition of 31.6 g (151 mmol) of tert-butyl bromopropionate at room temperature, refluxed for 5 days. The resulting precipitate was filtered off and washed several times with acetonitrile, the filtrate was concentrated under waterpump vacuum, the residue was taken up in 350 ml of dichloromethane, and the organic phase was extracted with 5% strength citric acid and saturated sodium bicarbonate solution. The organic phase was dried over sodium sulfate, filtered to remove desiccant and concentrated. The oily residue was purified by column chromatography (mobile phase dichloromethane, later dichloromethane/methanol 95:5). A slightly impure oil was obtained and was employed directly in the next reaction.)

c) N-Boc-N-(tert-Butyloxycarbonylethyl)-D-cyclohexylalanine benzyl ester

The oil obtained in the previous synthesis (30 g, max. 70 mmol) was dissolved in 150 ml of acetonitrile and, after addition of 28 ml (160 mmol) of diisopropylethylamine and 19.2 g (88 mmol) of di-tert-butyl dicarbonate, stirred at room temperature for 3 days. The reaction mixture was concentrated in a rotary evaporator under waterpump vacuum, the residue was taken up in n-hexane and washed five times with 3 ml of a 5% strength citric acid solution each time, the combined organic phases were dried over sodium sulfate, the desiccant was filtered off, and the residue after concentration was subjected to separation by column chromatography (mobile phase hexane/ethyl acetate 95:5). 32.66 g (64 mmol) of the required product were obtained.

d) N-Boc-N-(tert-Butyloxycarbonylethyl)-D-cyclohexylalanine cyclohexylammonium salt 32.66 g (64 mmol) of N-Boc-N-(tert-butyloxycarbonylethyl)-D-cyclohexylalanine benzyl ester were dissovled in 325 ml of pure ethanol and hydrogenated with hydrogen under atmospheric pressure at 25–30° C. in the presence of 3 g of 10% Pd on active carbon for 14 h. Filtration of the solution through Celite®, washing with ethanol and removal of the solvent in a rotary evaporator resulted in 26.7 g of a yellow oil, which was taken up in acetone and heated to reflux. The heating bath was removed, and a solution of 7 g (70 mmol) of cyclohexylamine in acetone was quickly added through a dropping funnel. The required salt crystallized out on cooling the reaction mixture to room temperature. The solid was filtered off, washed with 25 ml of acetone and, for final purification, recrystallized once more from acetone. Drying of the residue in a vacuum oven at 30° C. resulted in 26.6 g (54 mmol) of the required salt as a white powder.

N-Boc-N-(tert-Butyloxycarbonylmethyl)-(D)-cyclohexylalanyl-3,4-dehydroproline a) N-Boc-Pyr-OH (5 g, 23.45 mmol) was dissolved in MeOH (50 ml), and HCl in dioxane (4N, 30 ml) was added. After refluxing for 12 h, the solvent was removed in a rotary evaporator and H-Pyr-OMe hydrochloride was obtained as product. Yield: 3.84 g (100%).

b) N-(t-BuO$_2$C—CH$_2$)—N-Boc-(D)-Cha-OH (8 g, 20.75 mmol) was dissolved in dichloromethane (75 ml) and, at −10° C., ethyldiisopropylamine (15.5 ml, 89.24 mmol) was added. After stirring at this temperature for 5 min, a solution of H-Pyr-OMe hydrochloride (3.4 g, 20.75 mmol) in dichloromethane (25 ml) was added dropwise. A solution of propanephosphonic anhydride in ethyl acetate (50% strength, 20 ml, 26.96 mmol) was then added dropwise, and the mixture was stirred at −10 to 0° C. for 2 h. The mixture was diluted with dichloromethane and washed with saturated sodium bicarbonate solution (2×80 ml), 5% strength citric acid solution (2×15 ml) and saturated sodium chloride solution (1×20 ml). The organic phase was dried over sodium sulfate, and the solvent was removed in a rotary evaporator. The crude product was purified by flash chromatography (silica gel, dichloromethane/methanol=95/5). Yield: 6.2 g (60%).

c) N-(t-BuO$_2$C—CH$_2$)—N-Boc-(D)-Cha-Pyr-OMe (5.5 g, 11.12 mmol) was dissolved in dioxane (40 ml) and, after addition of sodium hydroxide solution (1N, 22.2 ml, 22.24 mmol), stirred at room temperature for 2 h. The dioxane was removed in a rotary evaporator, and the aqueous phase was washed with ethyl acetate and acidified to pH 1–2 with potassium bisulfate solution (20% strength). The aqueous phase was extrcted with dichloromethane, and the combined organic phases were dried over sodium sulfate. Yield: 5 g (94%), colorless foam. Recrystallization from n-hexane saturated with water afforded colorless crystals (m.p.=158–160° C.).

N-Boc-N-(tert-Butyloxycarbonylmethyl)-(D)-cyclohexylglycyl-3,4-dehydroproline This compound was prepared in an analogous manner from N-Boc-N-(tert-butyloxycarbonylmethyl)-(D)-cyclohexylglycine and 3,4-dehydroproline methyl ester.

(L)3,4-Dehydroproline employed as E building block can be purchased, and (D,L)-4,5-dehydropipecolic acid can be prepared by the method of A. Burgstahler, C. E. Aiman J. Org. Chem. 25 (1960), 489 or C. Herdeis, W. Engel Arch. Pharm 326 (1993), 297 and subsequently converted with (Boc)$_2$O into Boc-(D,L)-Dep-OH.

The D building blocks were synthesized as follows:

5-Aminomethyl-2-cyanothiophene

This building block was prepared as described in WO 95/23609

4-Aminomethyl-2-cyanothiophene a) 2-Bromo-4-formylthiophene 36 g (320 mmol) of 3-formylthiophene were dissolved in 600 ml of methylene chloride and cooled to 5° C., 100 g (750 mmol) of aluminum trichloride were added in portions, and the reaction mixture was then refluxed. A solution of 59 g (19 ml, 360 mmol) of bromine in 40 ml of methylene chloride was added dropwise over the course of 45 min, and the reaction was allowed to continue under reflux for 4 h. After cooling, the reaction solution was poured into 600 g of ice-water and extracted with methylene chloride, and the organic phase was washed with saturated sodium bicarbonate solution, dried over magnesium sulfate and concentrated in a rotary evaporator. 64.5 g of crude product were obtained and were purified by column chromatography (silica gel, methylene chloride/petroleum ether) to result in a total of 56.5 g of slightly impure product.

b) 2-Cyano-4-formylthiophene 7.6 g (85 mmol) of copper(I) cyanide were added to a solution of 13.53 g (70.82 mmol) of 2-bromo-4-formylthiophene in 25 ml of DMF, and the reaction mixture was refluxed for 3.5 h, during which the originally pale green suspension changed into a black solution. After addition of water, the reaction mixture was extrated several times with ethyl acetate, and the organic phases were combined, washed with saturated brine, dried over sodium sulfate and concentrated in a rotary evaporator under gentle vacuum. Addition of ether to the residue (7 g) resulted in 1.6 g of pure product. The mother liquor was purified together with the crude products from other batches by chromatography (silica gel, methylene chloride/petroleum ether 1:1). A total of 56.5 g of 2-bromo-4-formylthiophene was reacted to give 12.6 g of pure 2-cyano-4-formylthiophene (31% yield).

c) 2-Cyano-3-hydroxymethylthiophene 3.47 g (91.8 mmol) of sodium borohydride were added in portions to a suspension of 12.6 g (91.8 mmol) of 2-cyano-4-formylthiophene in 200 ml of ethanol, and the reaction mixture was stirred at room temperature for 2 h, during which it slowly formed a clear solution. The residue after concentration in vacuo was taken up in ethyl acetate and washed successively with saturated brine, 5% strength citric acid and saturated brine, and the organic phase was dried with sodium sulfate and concentrated in vacuo to result in 11.7 g of almost pure product (yield 91.5%).

d) 3-Bromomethyl-2-cyanothiophene 11.7 g (84.07 mmol) of 2-cyano-3-hydroxymethylthiophene were dissolved together with 24.1 g (91.87 mmol) of triphenylphosphine in 100 ml of THF at room temperature and, while cooling (ice bath), 30.47 g (91.87 mmol) of tetrabromomethane were added in portions. Stirring at room temperature for 3 hours was followed by concentration in vacuo and purification by chromatography over silica gel (methylene chloride/ petroleum ether) to result in 18.8 g of pale yellow crystalline product still containing petroleum ether.

e) 4-[N,N-Bis(tert-butoxycarbonyl)aminomethyl]-2-cyanothiophene 18.81 g of 3-bromomethyl-2-cyanothiophene (crude product, maximum 84.07 mmol) were dissolved in 160 ml of THF and cooled to 5° C., and 3.07 g (102.4 mmol) of 80% sodium hydride suspension were added in portions. Subsequently, 22.25 g (102.4 mmol) of di-tert-butyl iminodicarboxylate dissolved in 160 ml of THF were added dropwise at 5° C., and the mixture was then stirred at room temperature overnight. Since conversion was incomplete according to TLC, the mixture was heated at 30–35° C. for 4.5 h. After cooling to 0–5° C., 33 ml of saturated ammonium chloride solution were slowly added dropwise, THF was distilled off in vacuo, the residue was extracted several times with ethyl acetate, and the ethyl acetate phases were washed with saturated brine, dried over sodium sulfate and concentrated in a rotary evaporator. The viscous red residue (34.61 g) was employed as crude product in the next reaction.

f) 4-Aminomethyl-2-cyanothiophene hydrochloride 34.61 g of 4-[N,N-bis(tert-butoxycarbonyl)aminomethyl]-2-cyanothiophene (crude product, maximum 84.07 mmol) were dissolved in 600 ml of ethyl acetate, cooled to 0–5° C., saturated with HCl gas and warmed to room temperature. After 3 h, the resulting suspension was concentrated in a rotary evaporator and codistilled several times with methylene chloride, and the residue was extracted by stirring with ether and dried in vacuo. 13.85 g of product were obtained as a pale powder. Yield over two stages 94.3%.

2-Aminomethyl-4-cyanothiophene a) 4-Cyanothiophene-2-carbaldehyde 49.3 g (258.05 mmol) of 4-bromothiophene-2-carbaldehyde and 27.8 g (310.41 mmol) of copper(I) cyanide were suspended in 130 ml of absolute DMF and refluxed for 8 h. The solvent was removed in a rotary evaporator at 40° C., and the residue was suspended in ethyl acetate and transferred into a Soxhlet apparatus. The residue was extracted overnight, the yellow solution was dried over sodium sulfate and concentrated in a rotary evaporator, and the resulting yellow solid was recrystallized from ether to result in 25.3 g of product (80% of theory).

b) 4-Cyanothiophene-2-carbaldehyde oxime 11.6 g (84.6 mmol) of 4-cyanothiophene-2-carbaldehyde were dissolved in 140 ml of methanol, and 12.3 g (116.1 mmol) of sodium carbonate were added. Then 6.5 g (93.5 mmol) of hydroxylamine hydrochloride were added in portions while cooling at 15° C., and the mixture was stirred at 10° C. for 2 h. After addition of 80 ml of water, the reaction mixture was extracted five times with 50 ml of diethyl ether each time, the organic phase was dried over sodium sulfate, and the solvent was removed in vacuo to result in 12.5 g of the required product as a yellow crystalline powder (96% of theory).

c) 2-Aminomethyl-4-cyanothiophene hydrochloride 11.22 g (171.64 mmol) of fine zinc dust were added cautiously in several small portions to a solution of 4.65 g (30.60 mmol) of 4-cyanothiophene-2-carbaldehyde oxime in 50 ml of trifluoroacetic acid cooled to 0–5° C. in such a way that the temperature did not exceed 15° C. After stirring at room temperature for 3 h and decantation from excess zinc, the trifluoroacetic acid was substantially removed in vacuo (oil pump), the remaining oil was cooled to 0° C., and a mixture of 150 ml of 3N sodium hydroxide solution and 2 l of methylene chloride which had been cooled to 0° C. was added in portions. Insolubles were removed by filtration and then the organic phase was separated off, the aqueous phase was extracted eight times with 20 ml of methylene chloride, the collected organic phases were dried over sodium sulfate and then, while cooling in ice, 20 ml of 6M methanolic hydrochloric acid were added. The product precipitated in the form of the hydrochloride as a white solid, crystallization was completed by cooling the suspension at 4° C. overnight. 2.2 g of product were obtained as colorless needles (50% of theory).

5-Aminomethyl-3,4-dimethylthiophene-2-carboxamide hydrochloride 19 g (105.42 mmol) of 5-cyano-3,4-dimethylthiophene-2-carboxamide were suspended in 760 ml of methanol and 110 ml of 2N hydrochloric acid solution and, after addition of 9.5 g of Pd on carbon (10%), hydrogenated at room temperature. After uptake of 4.7 l of hydrogen (4 h), methanol was distilled out in vacuo, and the aqueous phase was extracted three times with ethyl acetate and then freeze dried. 16.3 g of the required product were obtained as a white solid (70.4% of theory).

5-Aminomethylisoxazole-3-carboxamide a) Ethyl 5-chloromethylisoxazole-3-carboxylate 21.2 g (210 mmol) of triethylamine were added dropwise to a stirred mixture of 30 g (198 mmol) of ethyl 2-chloro-2-hydroxyiminoacetate and 150 ml of propargyl chloride cooled to 10–15° C. and, after stirring at room temperature for 1 h, water was added, the mixture was extracted with ether, and the organic phase was dried over magnesium sulfate and concentrated in a rotary evaporator. The residue was distilled under 0.5 Torr, the product distilling over at 116–122° C.

b) 5-Chloromethylisoxazole-3-carboxylic acid 47.3 g (250 mmol) of 5-chloromethylisoxazole-3-carboxylate in 150 ml of ethanol were mixed with 14 g (250 mmol) of potassium hydroxide, and the reaction mixture was stirred at 60–70° C. for 6 h. After cooling and concentration in vacuo, the residue was taken up in water and extracted with ether, the aqueous phase was acidified with hydrochloric acid and then extracted several times with ether, and the ether phase was dried over sodium sulfate and concentrated in vacuo (oil pump, 50° C.). 31 g of the required product were obtained (77% of theory).

c) 5-Chloromethylisoxazole-3-carbonyl chloride 120 g (743 mmol) of 5-chloromethylisoxazole-3-carboxylic acid were refluxed together with 500 ml of thionyl chloride and 2 drops of pyridine for 10 h, then concentrated in vacuo and subsequently distilled under 20 Torr. The product distilled at 125–133° C. 78 g (58% of theory) were obtained.

d) 5-Chloromethylisoxazole-3-carboxamide

Ammonia was passed into a solution of 10 g (55.56 mmol) of 5-chloromethylisoxazole-3-carbonyl chloride in 100 ml of methylene chloride at 10–15° C. for 1 h, and the mixture was then stirred at room temperature for 1 h. After the solution had been cooled to 0° C., the precipitate was filtered off with suction and wahsed with a little cold methylene chloride, and the residue was extracted by stirring with water twice to remove ammonium salts. Drying in vacuo resulted in 6.58 g of pure product as a pale powder (74% of theory).

e) 5-Aminomethylisoxazole-3-carboxamide hydrochloride 2.44 g (15.2 mmol) of 5-chloromethylisoxazole-3-carboxamide were added to a mixture of 100 ml of concentrated ammonia solution and 72 ml of methanol, the reaction solution was warmed to 40° C. and, during this, continuously saturated with ammonia gas. The precursor had reacted after 6 h. The methanol was removed in vacuo, the aqueous phase was extracted twice with methylene chloride, and then the aqueous phase was carefully evaporated to dryness in vacuo. The solid white residue was employed as crude product in the couplings.

2-Aminomethyloxazole-4-thiocarboxamide and 2-aminomethylthiazole-4-thiocarboxamide were prepared as described by G. Videnov, D. Kaier, C. Kempter and G. Jung Angew. Chemie (1996) 108, 1604, deprotecting the N-Boc-protected compounds described therein with ethereal hydrochloric acid in ethylene chloride.

4-Aminomethylthiazole-2-thiocarboxamide a) Monothiooxamide

Monothiooxamide was prepared starting from ethyl thiooxamate by the method of W. Walter, K.-D. Bode Liebigs Ann. Chem. 660 (1962), 74–84.

b) 2-Carbamoyl-4-chloromethylthiazole 10 g (96 mmol) of ethyl thiooxamate were introduced into 170 ml of n-butanol and, after addition of 26 g (204 mmol) of 1,3-dichloroacetone, heated at 112° C. under nitrogen for 90 min. The reaction mixture was then concentrated in vacuo, and the residue was extracted by stirring with n-hexane (120 ml). This resulted in 10 g of pure product.

c) 4-Boc-Aminomethyl-2-carbamoylthiazole 10 g (56.6 mmol) of 2-carbamoyl-4-chloromethylthiazole were introduced into an ammonia-saturated solution of 350 ml of methanol and 80 ml of 25% strength aqueous ammonia solution. The reaction mixture was heated at 40–42° C., while continuing to saturate with ammonia, for 6 h, and was then concentrated in vacuo and codistilled with methanol, and the residue was then extracted by stirring firstly with ether and then with acetone. 7.6 g of crude product which still contained a little ammonium chloride were thus isolated. To remove this byproduct, the crude product was reacted with (Boc)$_2$O in aqueous dioxane solution and the protected compound was purified by column chromatography. This resulted in 4.95 g of pure product.)

d) 4-Boc-Aminomethyl-2-cyanothiazole 4.95 g (19.24 mmol) of 4-Boc-aminomethyl-2-carbamoylthiazole were introduced into 90 ml of methylene chloride and 16.7 ml (97.44 mmol) of diisopropylethylamine and, after cooling to 0° C., a solution of 6.35 ml of trifluoroacetic anhydride in 10 ml of methylene chloride was added dropwise at 0 to 5° C., and the mixture was then warmed to room temperature (TLC check). Then 25 ml of water were added and, after stirring at room temperature for 30 min and adjustment to pH 2.5 with 10% strength citric acid solution, the organic phase was washed several times, dried with magnesium sulfate and concentrated in vacuo. 5.4 g of pale brownish viscous crude product were obtained and were employed without further purification in the next stage.)

e) 4-Boc-Aminomethyl-2-thiocarbamoylthiazole

The crude product (max 19.24 mmol) obtained from d) was dissolved in 65 ml of pyridine and 5 ml of triethylamine, saturated with hydrogen sulfide and left to stand at room temperature over the weekend. The reaction mixture was then concentrated in vacuo, taken up in a mixture of ether and ethyl acetate, washed with 10% strength citric acid solution and water, dried over magnesium sulfate and concentrated in vacuo. This resulted in 6.0 g as a pale yellow solid foam.

f) 4-Aminomethyl-2-thiocarbamoylthiazole hydrochloride

The product obtained from the preceding experiment was taken up in 100 ml of methylene chloride and, after addition of 30 ml of approx. 5 molar ethereal hydrochloric acid solution, stirred at room temperature overnight. The reaction mixture was then evaporated to dryness in vacuo, codistilled with ether several times and then extracted by stirring with methylene chloride. 4.15 g of the required product were obtained as a pale yellow amorphous substance.

4-Amidino-2-(N-Boc-aminomethyl)-5-methylthiazole×HOAc a) α-Acetylglycine methyl ester hydrochloride

Potassium tertiary butoxide (17.8 g, 157.9 mmol) was introduced into THF (120 ml) and, at −70° C., a solution of N-(diphenylmethylidene)glycine methyl ester (40 g, 157.9 mmol) in THF (60 ml) was added. After stirring at this temperature for 30 min, the yellowish solution was added dropwise to a solution of acetyl chloride (12.4 g, 157.9 mmol) in THF (70 ml) at −70° C. After stirring at this temperature for 1.75 h, 3N HCl (160 ml) was added and the yellowish suspension was then stirred at room temperature for 10 min. The THF was removed in a rotary evaporator at room temperature, and the remaining aqueous phase was washed 3× with diethyl ether. The aqueous phase was freeze dried and the residue was extracted by stirring with methanol. The methanolic solution of the product was evaporated in a rotary evaporator at 35° C. Yield: 26.4 g (157.9 mmol, quant., yellowish solid).

b) Boc-Gly-(α-Acetyl-Gly)-OMe

Boc-Gly-OH (24.05 g, 137.27 mmol) was introduced into THF (400 ml) and triethylamine (13.87 g, 137.19 mmol) was added. The colorless solution was cooled to −20° C. and, at this temperature, a solution of isobutyl chloroformate (18.75 g, 137.28 mmol) in THF (20 ml) was added dropwise. The colorless suspension was stirred at −20° C. for 30 min and then α-acetylglycine methyl ester hydrochloride (23.0 g, 137.3 mmol) was added in portions. After stirring at −20° C. for 30 min, a solution of triethylamine (13.87 g, 137.19 mmol) in THF (20 ml) was added dropwise over the course of 45 min. Stirring at −20° C. for 4 h was followed by stirring at RT for 12 h. The residue was filtered off with suction and washed with THF, and the combined THF phases were concentrated in a rotary evaporator. Yield: 44.1 g (pale brownish oil).

$^1$H-NMR (270 MHz, CDCl$_3$) δ=1.45 (s, 9H), 2.40 (s, 3H), 3.85 (s, 3H), 3.90 (d, J=6.5 Hz, 2H), 5.25 (d, J=6.5 Hz, 1H), 7.30 (sbr, 1H).

c) Methyl 2-(N-Boc-aminomethyl)-5-methylthiazole-4-carboxylate

Boc-Gly-(α-Acetyl-Gly)-OMe (39.8 g, 138.2 mmol) was introduced into THF (400 ml) and, at room temperature, Lawesson's reagent (96.6 g, 238.8 mmol) was added in portions. The yellowish solution was then refluxed for 1.5 h. The THF was removed in a rotary evaporator. The residue (reddish brown oil) was extracted by stirring with diethyl ether (600 ml). The ether phase was decanted off the undissolved brownish oil and washed successively with 5% strength citric acid (2×), saturated NaHCO$_3$ solution (9×) and water (2×). After drying (MgSO$_4$), the solvent was removed in a rotary evaporator. Yield: 22.0 g (77 mmol, 56%, pale brownish solid).

$^1$H-NMR (270 MHz, CDCl$_3$) δ=1.50 (s, 9H), 2.75 (s, 3H), 3.95 (s, 3H), 4.55 (d, J=6.5 Hz, 2H), 5.45 (t, J=6.5 Hz, 1H). (Main rotamer in relation to Boc group)

d) 2-(N-Boc-Aminomethyl)-5-methylthiazole-4-carboxylic acid

Methyl 2-(N-Boc-aminomethyl)-5-methylthiazole-4-carboxylate (22.0 μg, 77 mmol) was dissolved in ethanol (100 ml), and a solution of LiOH (2.2 g, 92 mmol) in water (50 ml) was added. After stirring at room temperature for 30 min, the ethanol was removed in a rotary evaporator, and the remaining solution was diluted with water (70 ml). The aqueous phase was washed with ethyl acetate (3×) and adjusted to pH 2 with 20% strength NaHSO$_4$ solution, whereupon a pale brownish oil separated out. The aqueous phase was extracted with dichloromethane, and the combined organic extracts were dried (MgSO$_4$) and concentrated in vacuo. The pale brownish residue was extracted by stirring in diisopropyl ether. The remaining colorless precipitate was filtered off with suction and washed with diisopropyl ether. Yield: 6.9 g (25.4 mmol, 33%, colorless solid).

$^1$H-NMR (270 MHz, DMSO-d$_6$) δ=1.40 (s, 9H), 2.65 (s, 3H), 4.30 (d, J=6.5 Hz, 2H), 7.80 (t, J=6.5 Hz, 1H).

e) 2-(N-Boc-Aminomethyl)-5-methylthiazole-4-carboxamide 2-(N-Boc-Aminomethyl)-5-methylthiazole-4-carboxylic acid (6.8 g, 25 mmol) was dissolved in THF (100 ml), and triethylamine (2.53 g, 25 mmol) was added. After cooling to −20° C., a solution of isobutyl chloroformate (3.41 g, 25 mmol) in THF (10 ml) was added dropwise. After stirring at −20° C. for 30 min, gaseous ammonia was passed into the pale brownish suspension for 45 min. It was then warmed to room temperature. The residue was filtered off with suction and extracted with THF, and the filtrates were concentrated.

Yield: 6.9 g (25 mmol, quant.).

$^1$H-NMR (270 MHz, DMSO-d$_6$) δ=1.40 (s, 9H), 2.65 (s, 3H), 4.30 (m, 2H), 7.40 (sbr, 1H), 7.50 (sbr, 1H), 7.80 (t, J=6.5 Hz, 1H).

f) 4-Cyano-2-(N-Boc-aminomethyl)-5-methylthiazole 2-(N-Boc-Aminomethyl)-5-methylthiazole-4-carboxamide (6.8 g, 25 mmol) was introduced into dichloromethane (120 ml). After cooling to 0° C., diisopropylethylamine (15.84 g, 122.8 mmol) was added dropwise. Then, at −5° C., a solution of trifluoroacetic anhydride (8.25 g, 39.3 mmol) in dichloromethane (20 ml) was added dropwise over the course of min. After stirring at 0° C. for 30 min, the reaction mixture was warmed to room temperature and then stirred for 12 h. It was diluted with dichloromethane (100 ml) and washed with 20% strength citric acid, saturated NaHCO$_3$ solution and saturated NaCl solution. The organic phase was dried (MgSO$_4$) and concentrated in vacuo. Yield: 6.3 g (25 mmol, quant.).

g) 4-Amidino-2-(N-Boc-aminomethyl)-5-methylthiazole×CH$_3$COOH

4-Cyano-2-(N-Boc-aminomethyl)-5-methylthiazole (5.5 g, 21.74 mmol) was dissolved in methanol (15 ml) and N-acetylcysteine (4.1 g, 25.12 mmol) was added. The mixture was then heated to 60° C., and ammonia was passed in for 22 h. The mixture was diluted with methanol and passed over an acetate ion exchanger. The methanol was removed in a rotary evaporator, and the residue was extracted by stirring with acetone. The colorless residue was filtered off with suction and dried in vacuo. Yield: 4.75 g (14.4 mmol, 66%, colorless solid).

$^1$H-NMR (400 MHz, DMSO-d$_6$) δ=1.40 (s, 9H), 1.80 (s, 3H), 2.60 (s, 3H), 4.35 (d, J=6.5 Hz, 2H), 7.90 (t, J=6.5 Hz, 1H).

2-Aminomethyl-5-amidino-4-methylthiazole×2 HCl a) N-Boc-Glycinethioamide

N-Boc-Glycinonitrile (12.0 g, 76.8 mmol) and diethylamine (0.16 ml, 2.1 mmol) were dissolved in toluene (100 ml). The solution was cooled to −10° C., saturated with hydrogen sulfide and then stirred at room temperature overnight. The precipitate which formed was filtered off with suction and washed with toluene. The product was dried in vacuo at 45° C.

Yield: 13.2 g (69.4 mmol, 90.3%, yellowish solid).

$^1$H-NMR (270 MHz, DMSO-d$_6$) δ=1.40 (s, 9H), 3.80 (d, J=7 Hz, 2H), 7.05 (t, J=7 Hz, 1H), 9.0 (sbr, 1H), 9.65 (sbr, 1H).

b) Methyl 2-(N-Boc-aminomethyl)-4-methylthiazole-5-carboxylate

N-Boc-Glycinethioamide (10.0 g, 52.6 mmol) was introduced into methanol (70 ml) and methyl 2-chloracetate (7.9 g, 52.6 mmol) was added. The mixture was heated at 60° C. for 2 h and then stirred at room temperature for 48 h. The methanol was removed in a rotary evaporator, and the residue was extracted by stirring with acetone/diethyl ether. The remaining precipitate was filtered off with suction and the filtrate was concentrated. The solid obtained from the filtrate was the product (pure according to TLC and HPLC).

Yield: 8.7 g (30.4 mmol, 57.8%).

ESI-MS: 287 (M+H$^+$).

c) 2-(N-Boc-Aminomethyl)-4-methylthiazole-5-carboxylic acid

Methyl 2-(N-Boc-aminomethyl)-4-methylthiazole-5-carboxylate (2.8 g, 9.74 mmol) was dissolved in 1,4-dioxane (30 ml), and 1N sodium hydroxide solution (19 ml) was added. After stirring at room temperature for 4 h, the 1,4-dioxane was removed in a rotary evaporator. The residue was diluted with water and washed with ethyl acetate. The aqueous phase was acidified with 20% strength potassium bisulfate solution, and the resulting precipitate was filtered off with suction and washed with water. The product obtained in this way was dried in a vacuum oven at 40° C. Yield: 2.5 g.

d) 2-(N-Boc-Aminomethyl)-4-methylthiazole-5-carboxamide 2-(N-Boc-Aminomethyl)-4-methylthiazole-5-carboxylic acid (12.6 g, 46.27 mmol) was dissolved in dichloromethane (460 ml) and dimethylformamide (0.4 ml). After cooling to 0° C., a solution of oxalyl chloride (6.46 g, 50.90 mmol) in dichloromethane (40 ml) was added dropwise over the course of 30 min. After stirring at 0° C. for 2 h, the mixture was cooled to −20° C. and, at this temperature, ammonia was passed in until the reaction was complete. It was then warmed to room temperature and washed with water. The resulting precipitate was filtered off with suction. The organic phase was washed with 5% strength citric acid solution, dried (MgSO$_4$) and concentrated in a rotary evaporator. The resulting solid was combined with the previously filtered precipitate and dried in a vacuum oven at 50° C. Yield: 9.8 g (36.12 mmol, 78%).

e) 2-(N-Boc-Aminomethyl)-5-cyano-4-methylthiazole 2-(N-Boc-Aminomethyl)-4-methylthiazole-5-carboxamide (11.13 g, 41.02 mmol) was suspended in dichloromethane (75 ml) and cooled to 0° C. At this temperature, firstly ethyldiisopropylamine (17.86 ml, 102.55 mmol) and then slowly a solution of trifluoroacetic anhydride (6.56 ml, 47.17 mmol) in dichloromethane (20 ml) were added. After stirring for 1 h, the mixture was diluted with dichloromethane and washed with 5% strength citric acid solution. After drying (MgSO$_4$) and removal of the solvent in a rotary evaporator, the crude product was purified by flash chromatography. Yield: 6.5 g (25.66 mmol, 63%).

f) 2-(N-Boc-Aminomethyl)-4-methylthiazole-5-thiocarboxamide 2-(N-Boc-Aminomethyl)-5-cyano-4-methylthiazole (7.5 g, 29.61 mmol) was dissolved in pyridine (30 ml), and triethylamine (27 ml) was added. The solution was saturated with hydrogen sulfide at 0° C. and then left to stand at room temperature for 48 h. The solvent was then removed in a rotary evaporator, and the residue was taken up in ethyl acetate, washed with 20% strength potassium bisulfate solution and dried over magnesium sulfate. The solvent was removed in a rotary evaporator, and the crude product was dissolved in dichloromethane and precipitated with petroleum ether. The precipitated product was filtered off with suction and dried in a vacuum oven at 40° C. Yield: 7.1 g (24.7 mmol, 83%).

g) 5-Amidino-2-(N-Boc-aminomethyl)-4-methylthiazole×HOAc 2-(N-Boc-Aminomethyl)-4-methylthiazole-5-thiocarboxamide (7.1 g, 24.70 mmol) was dissolved in dichloromethane (40 ml), and iodomethane (17.5 g, 123.52 mmol) was added. After stirring at room temperature for 56 h, the solvent was removed in a rotary evaporator. The residue was dissolved in 10% strength methanolic ammonium acetate solution (29 ml) and stirred at 40° C. until the reaction was complete. The solvent was removed in a rotary evaporator, the residue was extracted by stirring with dichloromethane, and the resulting solid was filtered off with suction and washed with dichloromethane. The residue was dissolved in methanol and converted into the corresponding acetate using an acetate-loaded ion exchanger. The solvent was removed in a rotary evaporator and the resulting reddish brown oil was extracted by stirring with dichloromethane. This resulted in the product as a colorless solid which was dried in vacuo at 40° C. Yield: 5.3 g (16.04 mmol, 65%).

h) 5-Amidino-2-aminomethyl-4-methylthiazole×2 HCl

5-Amidino-2-(N-Boc-aminomethyl)-4-methylthiazole× HOAc (1.6 g, 4.84 mmol) was suspended in dichloromethane (20 ml) and, at room temperature, 4M hydrochloric acid in 1,4-dioxane (4.84 ml, 19.37 mmol) was added and the mixture was stirred at this temperature for 3 h. The product was filtered off and washed with dichloromethane, and dried in vacuo at 40° C.
Yield: 0.73 g (3.00 mmol, 62%).

2-Aminomethyl-5-amidino-4i-trifluoromethylthiazole×2 HCl a) Ethyl 2-(N-Boc-aminomethyl)-4-trifluoromethylthiazole-5-carboxylate N-Boc-Glycinethioamide (5.0 g, 26.28 mmol) was dissolved in acetonitrile. (60 ml) and, at 5 to 10° C., a solution of ethyl 2-chloro-4,4,4-trifluoroacetoacetate (6.38 g, 26.28 mmol) was added dropwise. The mixture was then stirred at 5° C. for 30 min and at room temperature for 12 h. It was then cooled to 0° C. and triethylamine (12 ml, 86.77 mmol) was added dropwise. After stirring at 0° C. for 20 min, the yellowish suspension had changed to a clear reddish brown solution. Then thionyl chloride (2.1 ml, 28.89 mmol) was slowly added dropwise at 0° C. Stirring at 0° C. for 20 min was followed by warming to room temperature in 1 h. The solvent was removed in a rotary evaporator, and the residue was taken up in water (100 ml) and extracted several times with ethyl acetate. The combined organic phases were dried (Na$_2$SO$_4$) and concentrated. The crude product was purified by chromatography (silica gel, MeOH:DCM=2:98). Yield: 2.2 g (6.4 mmol, 24.5%).
$^1$H-NMR (270 MHz, DMSO-d$_6$) δ=1.30 (t, J=6.5 Hz, 3H), 1.45 (s, 9H), 4.35 (q, J=6.5 Hz, 2H), 4.45 (d, J=6.5 Hz, 2H), 7.95 (t, J=6.5 Hz, 1H).

b) 2-(N-Boc-Aminomethyl)-4-trifluoromethylthiazole-5-carboxamide

Ethyl 2-(N-Boc-aminomethyl)-4-trifluoromethylthiazole-5-carboxylate (15 g, 42.33 mmol) was dissolved in methanol. Ammonia was passed through the solution at room temperature until the ester was completely converted into the carboxamide. The solvent was removed in a rotary evaporator, and the crude product was purified by flash chromatography. Yield: 4.6 g (14.14 mmol, 33%).

c) 2-(N-Boc-Aminomethyl)-5-cyano-4-trifluoromethylthiazole 2-(N-Boc-Aminomethyl)-4-trifluoromethylthiazole-5-carboxamide (4.6 g, 14.14 mmol) was dissolved in dichloromethane (30 ml) and cooled to −5° C. At this temperature, ethyldiisopropylamine (4.6 g, 35.35 mmol) and a solution of trifluoroacetic anhydride (3.4 g, 16.26 mmol) in dichloromethane (10 ml) were added. The mixture was then stirred at 0° C. for 2 h. It was washed successively with saturated sodium bicarbonate solution and 5% strength citric acid solution. After drying (MgSO$_4$) the solvent was removed in a rotary evaporator. The crude product was extracted by stirring with diethyl ether/petroleum ether. The supernatant was separated from the oil and concentrated in a rotary evaporator. Yield: 1.9 g (6.18 mmol, 44%).

d) 2-(N-Boc-Aminomethyl)-4-trifluoromethylthiazole-5-thiocarboxamide 2-(N-Boc-Aminomethyl)-5-cyano-4-trifluoromethylthiazole (4.6 g, 14.97 mmol) was dissolved in pyridine (20 ml) and, after addition of triethylamine (24 ml), the solution was saturated with hydrogen sulfide. After two days at room temperature, the solvent was removed in a rotary evaporator. The crude product was taken up in ethyl acetate and washed successively with 20% strength sodium bisulfate solution and water. After drying (MgSO$_4$), the solvent was removed in a rotary evaporator. The crude product was purified by flash chromatography. Yield: 2.5 g (7.32 mmol, 49%).

e) 5-Amidino-2-(N-Boc-aminomethyl)-4-trifluoromethylthiazole 2-(N-Boc-Aminomethyl)-4-trifluoromethylthiazole-5-thiocarboxamide (2.5 g, 7.32 mmol) was dissolved in dichloromethane (10 ml), and iodomethane (10.4 g, 73.24 mmol) was added. The mixture was then stirred at room temperature for 48 h. The solvent was removed in a rotary evaporator and the residue was taken up in methanol (5 ml), and 10% strength methanolic ammonium acetate solution (8.5 ml, 10.98 mmol) was added. After stirring at room temperature for 4 days, the solution of the crude product was passed over an acetate-loaded ion exchanger, and the solvent was removed in a rotary evaporator. The crude product was purified by flash chromatography. Yield: 0.8 g (2.08 mmol, 28%).

f) 5-Amidino-2-aminomethyl-4-trifluoromethylthiazole×2 HCl

5-Amidino-2-(N-Boc-aminomethyl)-4-trifluoromethylthiazole (0.8 g, 2.08 mmol) was dissolved in dichloromethane, and a 4M solution of hydrochloric acid in 1,4-dioxane (2.1 ml, 4.2 mmol) was added. After stirring at room temperature for 1 h, the solvent was removed in a rotary evaporator. The crude product obtained in this way was employed without further purification in the following reactions. Yield: 0.6 g (2.0 mmol, 97%).
ESI-MS: 225 (M+H$^+$).

5-Aminomethyl-3-methylthiophene-2-carbonitrile a) 5-Formyl-3-methylthiophene-2-carbonitrile 112 ml (179 mmol) of a 1.6 molar solution of n-butyllithium in n-hexane were added over the course of 20 min to a solution, cooled to −78° C., of 25.1 ml (179 mmol) of diisopropylamine in 400 ml of tetrahydrofuran. The solution was allowed to reach −35° C. and was cooled again to −78° C., and a solution of 20.0 g (162 mmol) of 2-cyano-3-methylthiophene in 80 ml of tetrahydrofuran was slowly added dropwise at this temperature. The solution became dark red in color. After stirring for 45 min, 63 ml (811 mmol) of dimethylformamide were slowly added dropwise, and stirring was continued for 30 min. For workup, a solution of 27 g of citric acid in 160 ml of water was added at −70° C. Concentration in a rotary evaporator and addition of 540 ml of saturated sodium chloride solution were followed by extraction three times with 250 ml of diethyl ether each time. The combined organic extracts were dried over magnesium sulfate. After filtering off the desiccant, the solvent was distilled off under waterpump vacuum and the residue was purified by column chromatography (mobile phase hexane/ethyl acetate 4/1). 23 g (94%) of the title compound were obtained.
$^1$H-NMR (270 MHz, DMSO-d$_6$): δ=2.4 (s, 3H), 8.0 (s, 1H), 9.8 (s, 1H).

b) 5-Hydroxymethyl-3-methylthiophene-2-carbonitrile 5.75 g (152 mmol) of sodium borohydride were added in portions to a solution of 23 g (152 mmol) of 5-formyl-3-methylthiophene-2-carbonitrile in 300 ml of absolute ethanol at room temperature. The reaction mixture was stirred for 5 minutes, concentrated under waterpump vacuum, taken up in ethyl acetate and extracted with 5% strength citric acid solution and with saturated sodium chloride solution, the organic phase was dried over magnesium sulfate, the desiccant was filtered off and the solvent was distilled off under waterpump vacuum at room temperature. This resulted in 24 g of the title compound as a dark red oil which still contained solvent and was employed without further purification in the following reactions.

$^1$H-NMR (270 MHz, DMSO-d$_6$): δ=2.4 (s, 3H), 4.7 (m, 2H), 5.9 (m, 1H), 7.0 (s, 1H).

c) 5-Bromomethyl-3-methylthiophene-2-carbonitrile 44 g (167 mmol) of triphenylphosphine were added to a solution of 24 g (152 mmol) of 5-hydroxymethyl-3-methylthiophene-2-carbonitrile in 180 ml of tetrahydrofuran. A solution of 55 g (167 mmol) of tetrabromomethane in 100 ml of tetrahydrofuran was then added. The reaction mixture was stirred at room temperature for 90 min. It was then concentrated in a rotary evaporator under waterpump vacuum, and the residue was purified by column chromatography (mobile phase hexane:ethyl acetate 8:2). 34 g of the title compound which still contained a little solvent were obtained.
$^1$H-NMR (270 MHz, DMSO-d$_6$): δ=2.4 (s, 3H), 5.0 (s, 2H), 7.3 (s, 1H).

d) 5-[N,N-Bis(tert-butoxycarbonyl)aminomethyl]-3-methylthiophene-2-carbonitrile 5.0 g (167 mmol) of sodium hydride (80% suspension in mineral oil) were added in portions to a solution, cooled to 0° C., of 33.8 g (152 mmol) of 5-bromomethyl-3-methylthiophene-2-carbonitrile in 255 ml of tetrahydrofuran. Then a solution of 36.4 g (167 mmol) of di-tert-butyl iminodicarboxylate in 255 ml of tetrahydrofuran was added dropwise, during which the temperature did not exceed 5° C. The mixture was allowed to reach room temperature and was stirred overnight. It was then heated at 35° C. for 3 hours to complete the reaction and, after cooling to room temperature, 510 ml of a saturated ammonium chloride solution were slowly added. The solvent was distilled off under waterpump vacuum, the residue was extracted several times with ethyl acetate, and the combined organic phases were washed with saturated sodium chloride solution, dried over magnesium sulfate and concentrated in a rotary evaporator. 57.6 g of an oily residue which still contained di-tert-butyl iminodicarboxylate were obtained and were employed as crude product in the following reaction.
$^1$H-NMR (270 MHz, DMSO-d$_6$): δ=1.45 (s, 18H), 2.35 (s, 3H), 4.85 (s, 2H), 7.05 (s, 1H).

e) 5-Aminomethyl-3-methylthiophene-2-carbonitrile hydrochloride 52.6 g of 5-[N,N-bis(tert-butoxycarbonyl)aminomethyl]-3-methylthiophene-2-carbonitrile (crude product from d), maximum 139 mmol) were dissolved in 950 ml of ethyl acetate and cooled to 0° C. On saturation with gaseous hydrogen chloride a white precipitate separated out after 10 min. After stirring at room temperature for two hours and at 30° C. for one hour, the resulting suspension was concentrated in a rotary evaporator, the residue was extracted by stirring with diethyl ether, the solvent was removed by filtration, and the solid residue was dried in vacuo at room temperature. 24.7 g (94%) of the title compound were obtained as a white powder.
$^1$H-NMR (270 MHz, DMSO-d$_6$): δ=2.4 (s, 3H), 4.25 (s, 2H), 7.3 (s, 1H), 8.8–9.0 (bs, 3H). $^{13}$C-NMR (DMSO-d$_6$): 15.0 (CH$_3$), 36.4 (CH$_2$), 104.8 (C-2), 113.8 (CN), 131.5 (C-4), 142.8 (C-5), 149.6 (C-3).

5-Aminomethyl-3-chlorothiophene-2-carbonitrile hydrochloride

This compound was prepared in analogy to 5-aminomethyl-3-methylthiophene-2-carbonitrile, preparing the 3-chloro-2-cyanothiophene used by dehydration of 3-chlorothiophene-2-carboxamide with trifluoroacetic anhydride.

2-Aminomethyl-3-methylthiophene-4-thiocarboxamide a) Ethyl 2-amino-3-cyano-4-methylthiophene-5-carboxylate

Ethyl 2-amino-3-cyano-4-methylthiophene-5-carboxylate was synthesized in accordance with "Organikum", 19$^{th}$ edition, Dt. Verlag der Wissenschaften, Leipzig, Heidelberg, Berlin, 1993, chapter 6, pages 374–375, starting from 130 g (1.0 mol) of ethyl acetoacetate, 66 g (1.0 mol) of malononitrile, 32 g (1.0 mol) of sulfur and 80 g (0.92 mol) of morpholine.

$^1$H-NMR (270 MHz, DMSO-d$_6$): δ=1.25 (t, 3H), 2.3 (s, 3H), 4.2 (q, 2H), 7.9 (bs, 2H).

b) Ethyl 4-cyano-3-methylthiophene-2-carboxylate

A solution of 20.5 g (97.5 mmol) of ethyl 2-amino-3-cyano-4-methylthiophene-5-carboxylate in 600 ml of a 1:1 mixture of acetonitrile and dimethylformamide was cooled to 5° C., and 15.7 g (146 mmol) of tert-butyl nitrite were added dropwise, during which the reaction mixture became hot and vigorous evolution of gas started. After stirring at room temperature for seven hours and concentrating in a rotary evaporator and under high vacuum, the residue was purified by column chromatography (mobile phase dichloromethane) to result in 9.1 g (48%) of the required compound as a yellow oil.

$^1$H-NMR (270 MHz, DMSO-d$_6$): δ=1.3 (t, 3H), 2.55 (s, 3H), 4.3 (q, 2H), 8.8 (s, 1H).)

c) 2-Hydroxymethyl-3-methylthiophene-4-carbonitrile 2.44 g (64 mmol) of lithium aluminum hydride were added in portions to a solution of 25.1 g (129 mmol) of ethyl 4-cyano-3-methylthiophene-2-carboxylate in 400 ml of tetrahydrofuran at 0° C. The mixture was stirred at room temperature for five hours, excess reducing agent was destroyed by adding 0.5N hydrochloric acid, and the reaction mixture was concentrated under waterpump vacuum, diluted with water and extracted three times with ethyl acetate. The combined organic phases were then washed once each with 0.5N hydrochloric acid and saturated sodium chloride solution. The organic phase was dried over magnesium sulfate, the desiccant was filtered off, and the solvent was distilled off under waterpump vacuum at room temperature. The residue was purified by column chromatography (mobile phase dichloromethane/methanol 95:5) to result in 16.1 g (83%) of the required compound as a pale yellow oil.

$^1$H-NMR (270 MHz, DMSO-d$_6$): δ=2.2 (s, 3H), 4.6 (d, 2H), 5.7 (m, 1H), 8.35 (s, 1H).

d) 2-Bromomethyl-3-methylthiophene-4-carbonitrile 30 g (115 mmol) of triphenylphosphine were added to a solution of 16 g (104 mmol) of 2-hydroxymethyl-3-methylthiophene-4-carbonitrile in 300 ml of tetrahydrofuran at 5° C. A solution of 38 g (115 mmol) of tetrabromomethane in 100 ml of tetrahydrofuran was then added. The reaction mixture was stirred at room temperature overnight. It was then concentrated in a rotary evaporator under waterpump vacuum, and the residue was purified by column chromatography (mobile phase petroleum ether: dichloromethane 1:1). 17 g (76%) of the title compound were obtained as a yellow oil.

$^1$H-NMR (270 MHz, DMSO-d$_6$): δ=2.25 (s, 3H), 5.0 (s, 2H), 8.5 (s, 1H).

e) 2-[N,N-Bis(tert-butoxycarbonyl)aminomethyl]-3-methylthiophene-3-carbonitrile 3.5 g (103 mmol) of sodium hydride (oil-free) were added in portions to a solution, cooled to 0° C., of 17.2 g (79.5 mmol) of 2-bromomethyl-3-methylthiophene-4-carbonitrile in 250 ml of tetrahydrofuran. A solution of 22.5 g (103 mmol) of di-tert-butyl iminodicarboxylate in 100 ml of tetrahydrofuran was then added dropwise, during which the temperature did not exceed 5° C. The mixture was allowed to warm to room temperature and was stirred for two hours. 400 ml of a saturated ammonium chloride solution were slowly added. The solvent was distilled off under waterpump vacuum, and the residue was diluted with a little water and extracted three times with ethyl acetate. The combined organic phases were washed with saturated ammonium chloride solution and with saturated sodium chloride solution, dried over magnesium sulfate and concentrated in a rotary evaporator. 28 g of an oil which still contained di-tert-butyl iminodicarboxylate were obtained and were employed as crude product in the following reaction.

$^1$H-NMR (270 MHz, DMSO-d$_6$): δ=1.4 (s, 9H), 1.45 (s, 9H), 2.3 (s, 3H), 4.8 (s, 2H), 8.4 (s, 1H).

f) 2-[N,N-Bis(tert-butoxycarbonyl)aminomethyl]-3-methylthiophene-4-thiocarboxamide The crude product (max. 79 mmol) obtained from e) was dissolved in 280 ml of pyridine and 140 ml of triethylamine and saturated with hydrogen sulfide at room temperature. The previously yellow solution became green. It was stirred at room temperature overnight. To complete the reaction, hydrogen sulfide was passed in for a further 15 min, and the mixture was stirred at room temperature for two hours. A stream of nitrogen was used to drive out excess hydrogen sulfide through a scrubbing tower. The reaction mixture was then concentrated in a rotary evaporator, taken up in ethyl acetate, washed several times with 20% strength sodium bisulfate solution, dried over magnesium sulfate and concentrated in a rotary evaporator. This resulted in 27 g of a pale yellow solid foam which was employed without further purification in the following reaction.

$^1$H-NMR (270 MHz, DMSO-d$_6$): δ=1.4 (s, 18H), 2.15 (s, 3H), 4.8 (s, 2H), 7.5 (s, 1H), 9.3 (bs, 1H), 9.75 (bs, 1H).

g) 2-Aminomethyl-3-methylthiophene-4-thiocarboxamide hydrochloride 27 g of 2-[N,N-bis(tert-butoxycarbonyl)aminomethyl]-3-methylthiophene-4-thiocarboxamide (crude product from f), maximum 70 mmol) were dissolved in 400 ml of ethyl acetate and cooled to 0° C. On saturation with gaseous hydrogen chloride, a white precipitate separated out after 10 min. After stirring at room temperature for two hours, the precipitate was filtered off and washed with ethyl acetate, and the solid residue was dried at room temperature in vacuo. 13.6 g (87%) of the title compound were obtained as a white powder.
EI-MS: $M^+$=186.

2-Aminomethyl-3-chlorothiophene-4-thiocarboxamide a) 2-Formyl-3-chlorothiophene-4-carbonitrile 35 g (325 mmol) of tert-butyl nitrite were added dropwise to a solution of 53.0 g (250 mmol) of 2-amino-4-chloro-5-formylthiophene-3-carbonitrile (the preparation of this compound is described in the patent DB 3738910) in 600 ml of a 1:1 mixture of acetonitrile and dimethylformamide at room temperature, during which the reaction mixture warmed from 20° C. to 37° C. and vigorous evolution of gas started. After cooling to 25° C. and stirring at room temperature for seven hours, the black solution was concentrated in a rotary evaporator and under high vacuum, and the residue was purified by column chromatography (mobile phase dichloromethane) to result in 29 g (68%) of the required compound as a yellow oil.
$^1$H-NMR (270 MHz, DMSO-$d_6$): δ=9.1 (S, 1H), 10.0 (s, 1H).

b) 2-Hydroxymethyl-3-chlorothiophene-4-carbonitrile 6.3 g (166 mmol) of sodium borohydride were added in portions to a solution of 28.5 g (166 mmol) of 2-formyl-3-chlorothiophene-4-carbonitrile in 400 ml of absolute methanol at 5° C. The reaction mixture became slightly warm and dark red in color. Vigorous evolution of gas was observed. After ten minutes, the reaction mixture was concentrated under waterpump vacuum, taken up in 200 ml of ethyl acetate, extracted with 200 ml of 1M hydrochloric acid, and washed twice with 250 ml of water each time and with saturated sodium chloride solution, the organic phase was dried over magnesium sulfate, the desiccant was filtered off, and the solvent was distilled off under waterpump vacuum at room temperature. 22 g (76%) of the title compound were obtained as a dark red oil which was employed without further purification in the following reactions.
$^1$H-NMR (270 MHz, DMSO-$d_6$): δ=4.65 (bs, 1H), 5.95 (t, 2H), 8.6 (s, 1H).

c) 2-Bromomethyl-3-chlorothiophene-4-carbonitrile 36.1 g (137 mmol) of triphenylphosphine were added to a solution of 21.7 g (125 mmol) of 2-hydroxymethyl-3-chlorothiophene-4-carbonitrile in 250 ml of tetrahydrofuran at 5° C. A solution of 45.6 g (137 mmol) of tetrabromomethane in 100 ml of tetrahydrofuran was then added. The mixture was stirred at room temperature overnight. The precipitate was filtered off, the filtrate was concentrated in a rotary evaporator under waterpump vacuum, and the residue was purified by column chromatography (mobile phase petroleum ether: dichloromethane 1:1). 26.0 g (88%) of the title compound were obtained as an oil.
$^1$H-NMR (270 MHz, DMSO-$d_6$): δ=4.95 (s, 2H), 8.8 (s, 1H).

d) 2-[N,N-Bis(tert-butoxycarbonyl)aminomethyl]-3-chlorothiophene-4-carbonitrile 6.9 g (159 mmol) of sodium hydride (oil-free) were added in portions to a solution, cooled to 0° C., of 25.0 g (106 mmol) of 2-bromomethyl-3-chlorothiophene-4-carbonitrile in 300 ml of tetrahydrofuran. A solution of 34.4 g (159 mmol) of di-tert-butyl iminodicarboxylate in 100 ml of tetrahydrofuran was then added dropwise, during which the temperature did not exceed 5° C. The mixture was allowed to warm to room temperature and was stirred for two hours. 300 ml of a saturated ammonium chloride solution were slowly added. The solvent was distilled off under waterpump vacuum, and the residue was diluted with a little water and extracted three times with ethyl acetate. The combined organic phases were washed with saturated ammonium chloride solution and with saturated sodium chloride solution, dried over magnesium sulfate and concentrated in a rotary evaporator. 51.3 g of an oil which still contained di-tert-butyl iminodicarboxylate and solvent residue were obtained and were employed as crude product in the following reaction.
$^1$H-NMR (270 MHz, DMSO-$d_6$): δ=1.4 (s, 9H), 1.45 (s, 9H), 4.8 (s, 2H), 8.65 (s, 1H).

e) 2-[N,N-Bis(tert-butoxycarbonyl)aminomethyl]-3-methylthiophene-4-thiocarboxamide Part of the crude product obtained from d) (39.4 g, max. 106 mmol) was dissolved in 400 ml of pyridine and 40 ml of triethylamine and, at room temperature, saturated with hydrogen sulfide. The previously yellow solution became green. It was stirred at room temperature overnight. A stream of nitrogen was used to drive out excess hydrogen sulfide through a scrubbing tower. The reaction mixture was then poured into ice-cold, 20% strength sodium bisulfate solution and extracted three times with ethyl acetate. The organic phase was subsequently washed several times with 20% strength sodium bisulfate solution, dried over magnesium sulfate and concentrated in a rotary evaporator. This resulted in 49.0 g of a solvent-containing residue which was employed without further purification in the following reaction.
$^1$H-NMR (270 MHz, DMSO-$d_6$): δ=1.4, 1.45 (s, 18H), 4.8 (s, 2H), 7.75 (s, 1H), 9.4 (bs, 1H), 10.0 (bs, 1H).

f) 2-Aminomethyl-3-chlorothiophene-4-thiocarboxamide hydrochloride 38.0 g of the crude product from e), maximum 93 mmol, were dissolved in 400 ml of ethyl acetate and cooled to 0° C. On saturation with hydrogen chloride gas a white precipitate separated out after 10 min. Since conversion was still incomplete, 200 ml of ethyl acetate were added and the solution was saturated again with hydrogen chloride gas and stirred at room temperature overnight. The precipitate was filtered off, washed with petroleum ether and dried at room temperature in vacuo. 21.1 g of the title compound were obtained as a white powder which contained ammonium chloride as impurity.

EI-MS: M+=206.

5-Aminomethyl-2-cyanofuran a) 5-Cyanofuran-2-carbaldehyde 165 ml (264 mmol) of a 1.6 molar solution of n-butyllithium in n-hexane were added over the course of 20 min to a solution of 26.7 g (264 mmol) of diisopropylamine in 600 ml of tetrahydrofuran cooled to −78° C. The solution was allowed to reach −20° C., again cooled to −75° C. and, at this temperature a solution of 22.3 g (240 mmol) of 2-cyanofuran in 100 ml of tetrahydrofuran was slowly added dropwise. After stirring for 30 min, 93 ml of dimethylformamide were slowly added dropwise, and the mixture was stirred for a further 30 min. For workup, a soluiton of 40 g of citric acid in 200 ml of water was added at −70° C. After concentration in a rotary evaporator, 600 ml of saturated sodium chloride solution were added, and the mixture was extracted three times with 200 ml of diethyl ether each time. The combined organic extracts were dried over magnesium sulfate. The desiccant was filtered off and then the solvent was distilled off under waterpump vacuum, and the residue was purified by column chromatography (mobile phase dichloromethane). The eluate was concentrated and the residue was subjected to steam distillation (boiling range of the azeotrope with water: 60 to 65° C. at p=0.1 mm Hg). Extraction of the distillate with diethyl ether, drying of the organic phase and concentration of the solution resulted in 10.6 g (88 mmol, 36%) of the title compound.

$^1$H-NMR (270 MHz, d$_6$-DMSO): δ=7.7 (d, 1H), 7.8 (d, 1H), 9.75 (s, 1H).

b) 5-Hydroxymethyl-2-cyanofuran 2.34 g (62 mmol) of sodium borohydride were added in portions to a solution of 30 g (0.25 mol) of 5-cyanofuran-2-carbaldehyde in 500 ml of absolute ethanol at −30° C. The solution was stirred at −30° C. for two hours and, while cooling, was adjusted to pH 7 with a 5% strength citric acid solution in water. The reaction mixture was concentrated under waterpump vacuum, saturated sodium chloride solution was added to the residue, the mixture was extracted several times with 150 ml of diethyl ether each time, the combined organic phases were dried over magnesium sulfate, the desiccant was filtered off, and the solvent was distilled off under waterpump vacuum at room temperature. This resulted in 27 g (22 mmol, 88%) of the title compound as a dark red oil, which was employed without further purification in the following reactions.

$^1$H-NMR (250 MHz, d$_6$-DMSO): δ=4.4 (m, 2H), 5.6 (bs, 1H), 6.6 (d, 1H), 7.5 (d, 1H).

c) 5-Bromomethyl-2-cyanofuran 38 g (145 mmol) of triphenylphosphine were added to a solution of 15 g (121 mol) of 5-hydroxymethyl-2-cyanofuran in 250 ml of tetrahydrofuran. The mixture was cooled to −10° C., and a solution of 48 g (145 mmol) of tetrabromomethane in 100 ml of tetrahydrofuran was added. The mixture was allowed to warm to room temperature and was stirred at this temperature for three hours. The reaction mixture was concentrated in a rotary evaporator under waterpump vacuum, and the residue was purified by column chromatography (mobile phase petroleum ether: dichloromethane 1:1, R$_f$=0.5). 11.5 g of the title compound were obtained.

$^1$H-NMR (250 MHz, d$_6$-DMSO): δ=4.8 (m, 2H), 6.7 (d, 1H), 7.7 (d, 1H).

d) 5-[N,N-Bis(tert-butoxycarbonyl)aminomethyl]-2-cyanofuran 4.0 g (135 mmol) of sodium hydride (80% suspension in mineral oil) were added in portions to a solution of 22.9 g (123 mmol) of 5-bromomethyl-2-cyanofuran in 400 ml of tetrahydrofuran cooled to 0° C. Then a solution of 29.4 g (135 mmol) of di-tert-butyl iminodicarboxylate in 200 ml of tetrahydrofuran was added dropwise, during which the temperature did not exceed 5° C. The mixture was allowed to warm to room temperature and was stirred overnight. Since conversion was incomplete (TLC check), a total of 1.2 g of sodium hydride was added in three portions over a period of 9 hours. To complete the conversion, the mixture was then heated at 35° C. for three hours and, after allowing to cool to room temperature, 600 ml of a saturated ammonium chloride solution were slowly added. The solvent was distilled off under waterpump vacuum, the residue was extracted several times with ethyl acetate, and the combined organic phases were washed with saturated sodium chloride solution, dried over magnesium sulfate and concentrated in a rotary evaporator. 37.3 g of an oily residue which still contained di-tert-butyl iminodicarboxylate were obtained and were employed as crude product in the following reaction.

$^1$H-NMR (250 MHz, d$_6$-DMSO): δ=1.40, 1.45 (s, 18H), 4.75 (s, 2H), 6.55 (d, 1H), 7.55 (d, 1H).

e) 5-Aminomethyl-2-cyanofuran hydrochloride 37.3 g of 5-[N,N-bis(tert-butoxycarbonyl)aminomethyl]-2-cyanofuran (crude product from d), maximum 123 mmol) were dissolved in 600 ml of ethyl acetate and cooled to 0° C. The solution was saturated with hydrogen chloride gas, a white precipitate separating out after 30 min. The mixture was allowed to reach room temperature and was stirred overnight, and then the resulting suspension was concentrated in a rotary evaporator, the residue was extracted by stirring with diethyl ether, the solvent was removed by filtration, and the solid residue was dried at room temperture in vacuo. 15.1 g (77% yield over two stages) of the title compound were obtained as a pale ochre powder.

$^1$H-NMR (250 MHz, d$_6$-DMSO): δ=4.15 (bs, 2H), 6.85 (d, 1H), 7.65 (d, 1H), 8.8–9.0 (bs, 3H).

2-Aminomethyl-4-cyanofuran hydrochloride a) 2-[N,N-Bis(tert-butoxycarbonyl)aminomethyl]-4-cyanofuran A solution, cooled to 0° C., of 20.5 g (0.11 mol) of 5-bromomethyl-3-cyanofuran (L. M. Pevzner, V. M. Ignat'ev, B. I. Ionin, Russ. J. of Gen. Chem. 1994, 64, 2, 125–128) in 50 ml of tetrahydrofuran was added over the course of 30 min to a stirred suspension of 4.8 g (0.12 mol) of sodium hydride (60% dispersion in mineral oil) in 30 ml of tetrahydrofuran at 0° C. A solution of 26.2 g (121 mmol) of di-tert-butyl iminodicarboxylate in 50 ml of tetrahydrofuran was then added dropwise, during which the temperature did not exceed 5° C. The mixture was stirred at 5 to 10° C. for three hours, allowed to warm to room temperature and stirred overnight. 150 ml of a saturated ammonium chloride solution were slowly added. The solvent was distilled off under waterpump vacuum, the residue was extracted four times with 60 ml of ethyl acetate each time, and the combined organic phases were washed twice with saturated sodium chloride solution, dried over magnesium sulfate and concentrated in a rotary evaporator. Drying at room temperture in vacuo (1 mm Hg) for three hours resulted in 33.2 g of a dark syrup which still contained di-tert-butyl iminodicarboxylate and was employed as crude product in the following reaction.
$^1$H-NMR (250 MHz, $d_6$-DMSO): $\delta$=1.40, 1.45 (s, 18H), 4.70 (s, 2H), 6.70 (s, 1H), 8.6 (s, 1H).

b) 2-Aminomethyl-4-cyanofuran hydrochloride 12.89 g of 2-[N,N-bis(tert-butoxycarbonyl)aminomethyl]-4-cyanofuran (crude product from a) were dissolved in 80 ml of ethyl acetate and cooled to −10° C. On saturation with hydrogen chloride gas a white precipitate separated out after 15 min. The mixture was allowed to reach room temperature and was stirred for two hours, the resulting suspension was then concentrated in a rotary evaporator, the residue (7 g) was extracted by stirring with diethyl ether, the solvent was removed by filtration, and the solid residue was dried at room temperature in vacuo. 5 g (79%) of the title compound were obtained as a pale ochre powder.
$^1$H-NMR (250 MHz, $d_6$-DMSO): $\delta$=4.15 (bs, 2H), 7.0 (s, 1H), 8.6–8.9 (m, 4H).

5-Aminomethyl-3-cyano-1,2,4-oxadiazole hydrochloride a) N-Boc-5-Aminomethyl-3-cyano-1,2,4-oxadiazole Ethyl N-Boc-5-aminomethyl-1,2,4-oxadiazole-3-carboxylate (S. Borg et al. J. Org. Chem. 1995, 60, 3112–20) was dissolved in methanol (50 ml). Ammonia was passed into this solution at −10° C. to RT until reaction was complete. The solvent was removed in a rotary evaporator. The crude product obtained in this way was dissolved in dichloromethane (70 ml) and, at −5° C., diisopropylethylamine (2.9 ml, 16.55 mmol) was added. Then trifluoroacetic anhydride (1.06 ml, 7.61 mmol) dissolved in dichloromethane (10 ml), was added dropwise. The mixture was stirred at 0° C. for 1.5 h and then diluted with dichloromethane, washed 2× with saturated sodium bicarbonate solution, 2× with 5% strength citric acid solution and 1× with saturated sodium chloride solution and then dried over sodium sulfate. The solvent was removed in a rotary evaporator and the crude product was purified by chromatography (silica gel, dichloromethane: methanol=97.5:2.5). Yield: 1.2 g (80%).

b) 5-Aminomethyl-3-cyano-1,2,4-oxadiazole hydrochloride

The product obtained in a) (0.9 g, 4.0 mmol) was dissolved in dichloromethane (45 ml) and, at RT, 4 M hydrochloric acid in dioxane (3.9 ml, 15.61 mmol) was added. After stirring at RT for 16 h, the solvent was removed in a rotary evaporator. Yield: 645 mg (100%).
$^1$H-NMR (DMSO-$d_6$) $\delta$=4.6 (s, 2H), 9.2 (s, 3H).

Example 1

N-(Hydroxycarbonylmethyl)-(D)-cyclohexylglycyl-3,4-dehydroproline 2-(N-methoxycarbonyl)amidino-5-thienylmethylamide hydrochloride a) 3,4-Dehydroproline 2-cyano-5-thienylmethylamide Boc-3,4-Dehydroproline (5 g, 23.4 mmol) and 5-aminomethyl-2-cyanothiophene hydrochloride (4.5 g, 25.8 mmol; WO 95/23609) were dissolved in dichloromethane (25 ml) and, at 0° C., ethyldiisopropylamine (28 ml, 163.8 mmol) and a 50% strength solution of propanephosphonic anhydride in ethyl acetate (24.8 ml, 117 mmol) were added. The mixture was stirred at 0° C. for 1 h and then warmed to RT and stirred at RT for 12 h. The reaction mixture was diluted with dichloromethane and washed with sodium bisulfate solution (4×), sodium bicarbonate solution (3×) and saturated sodium chloride solution (1×). After drying over sodium sulfate and removal of the desiccant by filtration, the solvent was distilled off under waterpump vacuum. To eliminate the Boc group, the residue was mixed with HCl in dichloromethane (95 ml), stirred at RT, evaporated to dryness, codistilled twice with dichloromethane, again concentrated and purified by column chromatography. 6.6 g of the required product, which still contained a small amount of solvent, were obtained.

b) N-(tert-butoxycarbonylmethyl)-(Boc)-(D)-cyclohexylglycyl-3,4-dehydroproline 2-cyano-5-thienylmethylamide t-BuO$_2$C—CH$_2$-(Boc)-(D)-Chg-OH (6.5 g, 17.5 mmol; WO 9806741) and H-Pyr-NH—CH$_2$-5-(2-CN)-thioph hydrochloride (4.72 g, 17.5 mmol) were suspended in dichloromethane (90 ml), and ethyldiisopropylamine (11.3 g, 87.5 mmol) was added, resulting in a clear, pale reddish solution. The reaction mixture was cooled to about 5° C. and a 50% strength solution of propanephosphonic anhydride in ethyl acetate (18 ml) was added dropwise. Stirring at RT overnight was followed by dilution with dichloromethane (100 ml) and washing with dilute sodium bisulfate solution (3×), saturated sodium bicarbonate solution (2×) and water (1×). Drying over sodium sulfate and removal of the desiccant was followed by removal of the solvent by distillation under waterpump vacuum. 11.15 g of a pale reddish brown oil were obtained.

c) N-(tert-Butoxycarbonylmethyl)-(Boc)-(D)-cyclohexylglycyl-3,4-dehydroproline 2-aminothiocarbonyl-5-thienylmethylamide The product obtained in b), t-BuO$_2$C—CH$_2$-(Boc)-(D)-Chg-Pyr-NH—CH$_2$-5-(2-CN)-thioph, was dissolved in pyridine (68 ml) and triethylamine (11.5 ml). The reaction mixture was cooled to 0° C. and saturated with hydrogen sulfide (the solution became green). The reaction solution was left to stand at RT overnight. The excess hydrogen sulfide was displaced by nitrogen, and the solvent was distilled off under waterpump vacuum. The residue was dissolved in diethyl ether (500 ml) and washed with dilute sodium bisulfate solution (3×), saturated sodium bicarbonate solution (2×) and water (1×). After drying over sodium sulfate, the solvent was distilled off under waterpump vacuum. The viscous yellow crude product (10.92 g) was employed without further purification in the next stage.

d) N-(tert-Butoxycarbonylmethyl)-(Boc)-(D)-cyclohexylglycyl-3,4-dehydroproline 2-methylthio(imino)methyl-5-thienylmethylamide hydroiodide The crude product obtained in c), t-BuO$_2$C—CH$_2$-(Boc)-(D)-Chg-Pyr-NH—CH$_2$-5-(2-CSNH$_2$)-thioph, was dissolved in dichloromethane (115 ml), and methyl iodide (14.99 g, 105.6 mmol) was added. After stirring at RT over the weekend, the solvent was removed by distillation under waterpump vacuum. 12.6 g of a yellowish solid foam were obtained.

e) N-(tert-Butoxycarbonylmethyl)-(Boc)-(D)-cyclohexylglycyl-3,4-dehydroproline 2-amidino-5-thienylmethylamide acetate The crude product obtained in d), t-BuO$_2$C—CH$_2$-(Boc)-(D)-Chg-Pyr-NH—CH$_2$-5-(2-C═NH(SCH$_3$))-thioph× HI, was mixed with 25.5 ml of a 10% strength solution of ammonium acetate in methanol (2.55 g of ammonium acetate, 38.12 mmol). Since precursor was still present according to TLC after stirring at RT overnight, a further 3.0 ml of a 10% strength solution of ammonium acetate in methanol was added and the mixture was stirred at RT overnight. The solvent was then removed by distillation under waterpump vacuum, the residue was taken up in dichloromethane, the salts were filtered off with suction, and the filtrate was concentrated, resulting in 13.3 g of crude product in the form of a yellow solid foam. The product was dissolved in methanol and converted into the corresponding acetate salt on an ion exchanger (Fluka: acetate on polymeric support, 3.0 mmol of acetate per g).

f) N-(tert-Butoxycarbonylmethyl)-(Boc)-(D)-cyclohexylglycyl-3,4-dehydroproline 2-amidino-5-thienylmethylamide The crude product obtained in e), t-BuO$_2$C—CH$_2$-(Boc)-(D)-Chg-Pyr-NH—CH$_2$-5-(2-C═NH(NH$_2$))-thioph× CH$_3$COOH, was dissolved in methylene chloride, concentrated ammonia solution was added (pH 11), the aqueous phase was extracted several times with methylene chloride, and the combined organic phases were dried over magnesium sulfate and concentrated in vacuo. The product was obtained as a white solid.

g) N-(tert-Butoxycarbonylmethyl)-(Boc)-(D)-cyclohexylglycyl-3,4-dehydroproline 2-(N-methoxycarbonyl)amidino-5-thienylmethylamide The crude product obtained in f), t-BuO$_2$C—CH$_2$-(Boc)-(D)-Chg-Pyr-NH-CH$_2$-5-(2-C═NH(NH$_2$))-thioph (1.4 g, 2.32 mmol), were dissolved in 50 ml of methylene chloride and, after addition of diisopropylamine (3.0 g, 23.2 mmol) and then, while cooling with a waterbath, dropwise methyl chloroformate (0.24 g, 2.55 mmol) in 5 ml of methylene chloride, the mixture was stirred at room temperature for 1 h. The residue after concentration in vacuo was mixed with ether, water and 5% strength citric acid (pH 5) and extracted, and the ether phase once again washed with acid (pH 3), dried over magnesium sulfate and concentrated in vacuo. 1.7 g of the product were obtained as a colorless foam.)

h) N-(Hydroxycarbonylmethyl)-(D)-cyclohexylglycyl-3,4-dehydroproline 2-(N-methoxycarbonyl)amidino-5-thienylmethylamide hydrochloride The crude product obtained in g), t-BuO$_2$C—CH$_2$-(Boc)-(D)-Chg-Pyr-NH—CH -5-(2═NH(NH—COOCH$_3$))-thioph (1.7 g, max. 2.3 mmol), was dissolved in a mixture of 45 ml of methylene chloride, 20 ml of dioxane and 45 ml of 4N hydrochloric acid in dioxane and stirred overnight with exclusion of moisture. The reaction solution was concentrated in vacuo, and the residue was codistilled with ether several times and subsequently extracted by stirring with ether. After drying in vacuo, 1.3 g of the title compound were obtained as a white solid product. Neutral aqueous solutions of the product are distinctly more stable than acidic solutions because the acylated amidine function is hydrolyzed under these conditions.

FAB-MS (M+H$^+$): 506

Example 2

N-(Hydroxycarbonylmethyl)-(D)-cyclohexylglycyl-3,4-dehydroproline 2-(N-isobutyloxycarbonyl)amidino-5-thienylmethylamide hydrochloride: FAB-MS (M+H$^+$): 548

Preparation took place in analogy to Example 1 by reacting t-BuO$_2$C—H$_2$-(Boc)-(D)-Chg-Pyr-NH—CH$_2$-5-(2-C═NH(NH$_2$))-thioph with isobutyl chloroformate and subsequently eliminating protective groups.

Example 3

N-(Hydroxycarbonylmethyl)-(D)-cyclohexylglycyl-3,4-dehydroproline 2-(N-n-hexyloxycarbonyl)amidino-5-thienylmethylamide hydrochloride: FAB-MS (M+H$^+$): 576

Preparation took place in analogy to Example 1 by reacting t-BuO$_2$C—CH$_2$-(Boc)-(D)-Chg-Pyr-NH—CH$_2$-5-(2-C═NH(NH$_2$))-thioph with hexyl chloroformate and subsequently eliminating protective groups.

Example 4

N-(Hydroxycarbonylmethyl)-(D)-cyclohexylglycyl-3,4-dehydroproline 2-(N-allyloxycarbonyl)amidino-5-thienylmethylamide hydrochloride: FAB-MS (M+H⁺): 532

Preparation took place in analogy to Example 1 by reacting t-BuO₂C—CH₂-(Boc)-(D)-Chg-Pyr-NH-CH₂-5-(2-C=NH(NH₂))-thioph with allyl chloroformate and subsequently eliminating protective groups.

Example 5

N-(Hydroxycarbonylmethyl)-(D)-cyclohexylglycyl-3,4-dehydroproline 2-(N-benzyloxycarbonyl)amidino-5-thienylmethylamide hydrochloride: FAB-MS (M+H⁺): 582

Preparation took place in analogy to Example 1 by reacting t-BuO₂C—CH₂-(Boc)-(D)-Chg-Pyr-NH—CH₂-5-(2-C=NH(NH₂))-thioph with benzyl chloroformate and subsequently eliminating protective groups.

Example 6

N-(Hydroxycarbonylmethyl)-(D)-cyclohexylglycyl-3,4-dehydroproline 2-(N-methoxyethoxycarbonyl)amidino-5-thienylmethylamide hydrochloride: FAB-MS (M+H⁺): 550

Preparation took place in analogy to Example 1 by reacting t-BuO₂C—CH₂-(Boc)-(D)-Chg-Pyr-NH—CH₂-5-(2-C=NH(NH₂))-thioph with methoxyethyl chloroformate and subsequently eliminating protective groups.

Example 7

N-(Hydroxycarbonylmethyl)-(D)-cyclohexylglycyl-3,4-dehydroproline 2-(N-methoxyethoxyethoxycarbonyl)amidino-5-thienylmethylamide hydrochloride: FAB-MS (M+H⁺): 594

Preparation took place in analogy to Example 1 by reacting t-BuO₂C—CH₂-(Boc)-(D)-Chg-Pyr-NH—CH₂-5-(2-C=NH(NH₂))-thioph with methoxyethoxyethyl chloroformate and subsequently eliminating protective groups.

Example 8

N-(Hydroxycarbonylmethyl)-(D)-cyclohexylglycyl-3,4-dehydroproline 2-(N-methoxyamidino)-5-thienylmethylamide hydrochloride a) N-(tert-Butoxycarbonylmethyl)-(Boc)-(D)-cyclohexylglycyl-3,4-dehydroproline 2-(N-methoxyamidino)-5-thienylmethylamide Methoxylamine hydrochloride (0.7 g, 8.38 mmol) was dissolved in 50 ml of methanol and converted into the corresponding acetate salt on an ion exchanger (Fluka: acetate on polymeric support, 3.0 mmol of acetate per g). t-BuO₂C—CH₂-(Boc)-(D)-Chg-Pyr-NH—CH₂-5-(2-C=NH(SCH₃))-thioph×HI (3.0 g, 4.0 mmol; see Example 1d) was added to this methanolic solution, and the reaction mixture was stirred at 50° C. for 15 min (TLC check (methylene chloride/acetone: 9/1)). The residue after concentration in vacuo was purified by chromatography on silica gel, it being possible to isolate 1.0 g of the required product as a pale yellow solid.

b) N-(Hydroxycarbonylmethyl)-(D)-cyclohexylglycyl-3.4-dehydroproline 2-(N-methoxyamidino)-5-thienylmethylamide hydrochloride The product obtained in a), t-BuO₂C—CH₂-(Boc)-(D)-Chg-Pyr-NH—CH₂-5-(2-C=NH(NHOCH₃))-thioph (0.9 g, 1.42 mmol), was stirred in a mixture of 10 ml of methylene chloride and 5 ml of 5 N hydrochloric acid solution in ether at room temperature with exclusion of moisture for 24 h, and then 60 ml of ether were added and the precipitated solid was filtered off. The latter was dissolved in 20 ml of water, and the aqueous phase was extracted 3 times with ethyl acetate and freeze dried. 0.7 g of the title compound was obtained as a white powder.

FAB-MS (M+H⁺): 478

Example 9

N-(Hydroxycarbonylmethyl)-(D)-cyclohexylglycyl-3.4-dehydroproline 2-(N-isobutyloxyamidino)-5-thienylmethylamide hydrochloride: FAB-MS (M+H⁺): 520

Preparation took place in analogy to Example 8 by reacting t-BuO₂C—CH₂-(Boc)-(D)-Chg-Pyr-NH—CH₂-5-(2-C=NH(SCH₃))-thioph×HI with O-isobutylhydroxylamine and subsequently eliminating protective groups.

Example 10

N-(Hydroxycarbonylmethyl)-(D)-cyclohexylglycyl-3.4-dehydroproline 2-(N-(p-methylbenzyloxy)amidino)-5-thienylmethylamide hydrochloride: FAB-MS (M+H⁺): 568

Preparation took place in analogy to Example 8 by reacting t-BuO₂C—CH₂-(Boc)-(D)-Chg-Pyr-NH—CH₂-5-(2-C=NH(SCH₃))-thioph×HI with O-(p-methylbenzyl)hydroxylamine and subsequently eliminating protective groups.

Example 11

N-(Ethoxycarbonylmethyl)-(D)-cyclohexylglycyl-3,4-dehydroproline 2-(N-(p-methylbenzyloxy)amidino)-5-thienylmethylamide hydrochloride: FAB-MS (M+H⁺): 596

Preparation took place in analogy to Example 8 by reacting t-BuO₂C—CH₂-(Boc)-(D)-Chg-Pyr-NH—CH₂-5-(2-C=NH(SCH₃))-thioph×HI with O-(p-methylbenzyl)hydroxylamine and subsequently eliminating protective groups in ethanol, there being simultaneous esterification to give the ethyl ester.

Example 12

N-(Hydroxycarbonylmethyl)-(D)-cyclohexylglycyl-3.4-dehydroproline 2-hydroxyamidino-5-thienylmethylamide hydrochloride

FAB-MS (M+H$^+$): 464

Preparation took place in analogy to Example 8 by reacting t-BuO$_2$C—CH$_2$-(Boc)-(D)-Chg-Pyr-NH—CH$_2$-5-(2-C=NH(SCH$_3$))-thioph×HI with hydroxylamine hydrochloride in methylene chloride with the aid of diisopropylethylamine as base. The protective groups were eliminated in 2N aqueous hydrochloric acid at 60° C. within 35 min.

Example 13

N-(Hydroxycarbonylmethyl)-(D)-cyclohexylglycyl-3.4-dehydroproline 4-(N-methoxyamidino)-2-thienylmethylamide hydrochloride a) 3,4-Dehydroproline 4-cyano-2-thienylmethylamide hydrochloride This compound was prepared in analogy to Example 1a), employing 2-aminomethyl-4-cyanothiophene (WO 98/06741).

b) N-(tert-Butoxycarbonylmethyl)-(Boc)-(D)-cyclohexylglycyl-3,4-dehydroproline 4-cyano-2-thienylmethylamide This compound was prepared in analogy to Example 1b).

c) N-(tert-Butoxycarbonylmethyl)-(Boc)-(D)-cyclohexylglycyl-3,4-dehydroproline 4-methylthioiminomethyl-2-thienylmethylamide hydroiodide This compound was prepared in analogy to Example 1c) and d).

d) N-(tert-Butoxycarbonylmethyl)-(Boc)-(D)-cyclohexylglycyl-3,4-dehydroproline 4-(N-methoxyamidino)-2-thienylmethylamide This compound was prepared in analogy to Example 8a).

e) N-(Hydroxycarbonylmethyl)-(D)-cyclohexylglycyl-3,4-dehydroproline 4-(N-methoxyamidino)-2-thienylmethylamide hydrochloride The protective groups were eliminated with dioxane/HCl f) FAB-MS (M+H$^+$): 478

Example 14

N-(Cyclohexyloxycarbonylmethyl)-(D)-cyclohexylglycyl-3,4-dehydroproline 4-(N-methoxyamidino)-2-thienylmethylamide hydrochloride This compound was synthesized by reacting the compound detailed in Example 13d) with cyclohexanol in 5M hydrochloric acid in dioxane at 50° C., which achieved elimination of the protective groups and transesterification/esterification of the carboxyl function to give the cyclohexyl ester.

FAB-MS (M+H$^+$): 560

Example 15

N-(Methoxycarbonylmethyl)-(D)-cyclohexylglycyl-3,4-dehydroproline 4-(N-methoxyamidino)-2-thienylmethylamide hydrochloride Preparation took place in analogy to Example 14.
FAB-MS (M+H$^+$): 492

Example 16

N-(Isopropyloxycarbonylmethyl)-(D)-cyclohexylglycyl-3,4-dehydro-proline 4-(N-methoxyamidino)-2-thienylmethylamide hydrochloride Preparation took place in analogy to Example 14.
FAB-MS (M+H$^+$): 520

Example 17

N-(tert-Butoxycarbonylmethyl)-(D)-cyclohexylglycyl-3,4-dehydro-proline 4-hydroxyamidino-2-thienylmethylamide a) (D)-cyclohexylglycyl-3,4-dehydroproline 4-cyano-2-thienylmethylamide hydrochloride H-Pyr-NH—CH$_2$-5-(3-CN)-thioph hydrochloride (Example 13a) and Boc-(D)Chg-OH were reacted in analogy to Example 1b) to give Boc-(D)-Chg-Pyr-NH—CH$_2$-5-(3-CN)-thioph and the Boc protective group was then eliminated with hydrochloric acid in ether/ethyl acetate, resulting in H-(D)-Chg-Pyr-NH—CH$_2$-5-(3-CN)-thioph hydrochloride as a white solid.

b) N-(tert-Butoxycarbonylmethyl)-(D)-cyclohexylglycyl-3,4-dehydroproline 4-cyano-2-thienylmethylamide The product obtained in a), H-(D)-Chg-Pyr-NH—CH$_2$-5-(3-CN)-thioph hydrochloride (4.8 g, 11.7 mmol), was suspended in 10 ml of methylene chloride and, after addition of 40 ml of ammonia-saturated methylene chloride solution, stirred for 20 min, and then magnesium sulfate was added and the solids were filtered off. Evaporation of the filtrate in vacuo was followed by codistillation with methylene chloride several times until ammonia was completely removed. H-(D)-Chg-Pyr-NH—CH$_2$-5-(3-CN)-thioph as base was dissolved in 60 ml of methylene chloride, followed by addition of diisopropylethylamine (6.1 g, 8.0 ml, 47 mmol) and then, while cooling, dropwise tert-butyl bromoacetate (2.3 g, 11.7 mmol) in 10 ml of methylene chloride. After 24 h, TLC (methylene chloride/methanol: 9/1) showed 90% of the precursor had reacted. The reaction solution was adjusted to pH 3 with aqueous hydrochloric acid and extracted with methylene chloride, with unreacted precursor remaining in the aqueous phase. The residue after drying of the organic phase and evaporation in vacuo was dissolved in a little methylene chloride and precipitated with n-hexane and the solid was filtered off. 5.2 g of the title compound were obtained as a white solid.

c) N-(tert-Butoxycarbonylmethyl)-(D)-cyclohexylglycyl-3,4-dehydroproline 4-hydroxyamidino-2-thienylmethylamide The product obtained in b), t-BuO$_2$C—CH$_2$-(D)-Chg-Pyr-NH—CH$_2$-5-(3-CN)-thioph (5.2 g, 10.7 mmol), was dissolved in 60 ml of methanol and, after addition of hydroxylamine hydrochloride (1.86 g, 26.7 mmol) and diisopropylethylamine ((6.9 g, 9.15 ml, 53.4 mmol), stirred at room temperature overnight. The reaction solution was evaporated in vacuo and then the residue was taken up in aqueous hydrochloric acid at pH 3 and extracted with ethyl acetate, the aqueous phase was adjusted to pH 8 with sodium bicarbonate and again extracted several times with ethyl acetate, and this organic phase was dried over magnesium sulfate and concentrated in vacuo. The resulting product was dissolved in the minimum amount of methylene chloride and reprecipitated with ether. 2.9 g of the title compound were obtained as a white solid.

FAB-MS (M+H$^+$): 520

Example 18

N-(Hydroxycarbonylmethyl)-(D)-cyclohexylglycyl-3,4-dehydroproline 4-(1,2,4-oxadiazol-5-on-3-yl)-2-thienylmethylamide hydrochloride a) N-(tert-Butoxycarbonylmethyl)-N-(Boc)-(D)-cyclohexylglycyl-3,4-dehydroproline 4-hydroxyamidino-2-thienylmethylamide A solution of 5.0 g (8.5 mmol) of the product obtained in Example 13b), t-BuO$_2$C—CH$_2$—N-Boc-(D)-Chg-Pyr-NH—CH$_2$-5-(3-CN))-thioph, 1.3 g (17 mmol) of hydroxylamine hydrochloride, and 1.98 g (15.3 mmol) of diisopropylethylamine in 50 ml of ethanol was heated at 55 to 60° C. for five hours. The solution was then concentrated in vacuo, and the residue was taken up in 50 ml of ethyl acetate and washed twice with saturated brine. Drying over magnesium sulfate was followed by removal of the solvent by distillation. 4.6 g (87%) of a pale yellowish amorphous residue were obtained.

b) N-(tert-Butyloxycarbonylmethyl)-N-(Boc)-(D)-cyclohexylglycyl-3,4-dehydroproline 4-(1,2,4-oxadiazol-5-on-3-yl)-2-thienylmethylamide hydrochloride 4.6 g (7.4 mmol) of the amide oxime obtained in a) were dissolved in 30 ml of pyridine and, after addition of 1.3 g (8.0 mmol) of carbonyldiimidazole, refluxed for three hours. The pyridine was distilled off in vacuo, and the residue was taken up in tert-butyl methyl ether and washed with 5% strength citric acid solution and saturated brine. The residue after drying over magnesium sulfate and distilling off the solvent was purified by column chromatography (dichloromethane/methanol/glacial acetic acid 95/5/1) to give 3.8 g (79%) of amorphous residue.

c) N-(Hydroxycarbonylmethyl)-(D)-cyclohexylglycyl-3,4-dehydroproline 4-(1,2,4-oxadiazol-5-on-3-yl)-2-thienylmethylamide hydrochloride The 1,2,4-oxadiazol-5-one obtained in b) (3.8 g, 5.9 mmol) was dissolved in 40 ml of glacial acetic acid and, after addition of 40 ml of 4N hydrochloric acid in 1,4-dioxane, left to stand at room temperature overnight. The solvent was distilled off as far as possible and toluene was added several times in order to be able to remove even the last residues of the solvent by distillation in a rotary evaporator. Purification by column chromatography (ethanol/25% strength aqueous ammonia solution 50:2.5) resulted in an amorphous powder which was taken up in a dioxane/water (7:3) mixture. One equivalent of 32% strength hydrochloric acid was added, and the residue after evaporation to dryness was digested with acetonitrile to result in 1.9 g (62%) of a white powder. FAB-MS (M+H$^+$): 489

Example 19

N-(Methoxycarbonylmethyl)-(D)-cyclohexylglycyl-3,4-dehydroproline 4-(1,2,4-oxadiazol-5-on-3-yl)-2-thienylmethylamide hydrochloride 0.8 g (1.5 mmol) of the product obtained in Example 18 c) was dissolved in 50 ml of methanol and, after addition of 5 ml of a solution of 4N hydrochloric acid in 1,4-dioxane, refluxed for eight hours. The solvent was distilled off as far as possible and toluene was added several times in order to be able to remove even the last residues of the solvent by distillation in a rotary evaporator. The residue was digested with acetonitrile and filtered. 0.65 g (79%) of a white powder was obtained.

FAB-MS (M+H$^+$): 503

Example 20

N-(Cyclohexyloxycarbonylmethyl)-(D)-cyclohexylalanyl-3,4-dehydro-proline 4-amidino-2-thiazolylmethylamide dihydrochloride HO$_2$C—CH$_2$-(D)-Cha-Pyr-NH—CH$_2$-2-(4 am)-thiaz (1.5 g, 3.24 mmol; preparation: WO 9806741, Example 21) was dissolved in 20 ml of cyclohexanol and, after addition of hydrochloric acid in ether (5N, 10 ml), stirred at 60° C. for 6 h. Since the reaction was still incomplete according to TLC (methylene chloride/methanol/acetic acid: 100/20/5), a further 15 ml of 5N hydrochloric acid in ether were added and the mixture was stirred at 60° C. for 4 h. After concentration of the reaction mixture in vacuo it was codistilled several times with methylene chloride and ether to remove adherent hydrochloric acid. The product was then dissolved in a little methylene chloride and precipitated with ether, and the residue was filtered off with suction and dried in vacuo. 1.85 g of the title compound were obtained as a white hygroscopic solid.

FAB-MS (M+H$^+$): 545

Example 21

N-(Hexadecyloxycarbonylmethyl)-(D)-cyclohexylalanyl-3,4-dehydroproline 4-amidino-2-thiazolylmethylamide dihydrochloride Preparation took place in analogy to Example 20 by esterification of HO$_2$C—CH$_2$-(Boc)-(D)-Cha-Pyr-NH—CH$_2$-2-(4-am))-thiaz with 1-hexadecanol, the reaction taking place at 135° C. for 4 h, and the subsequent purification of the reaction mixture taking place by column chromatography (silica gel/methylene chloride with increasing methanol content).

FAB-MS (M+H$^+$): 687

Example 22

N-(Undecyloxycarbonylmethyl)-(D)-cyclohexylalanyl-3,4-dehydroproline 4-amidino-2-thiazolylmethylamide diacetate Preparation took place in analogy to Example 20 by esterification of HO$_2$C—CH$_2$-(Boc)-(D)-Cha-Pyr-NH—CH$_2$-2-(4-am))-thiaz with 1-undecanol, the reaction mixture being purified by RP-HPLC (acetonitrile, water, acetic acid gradient).

FAB-MS (M+H$^+$): 617

Example 23

N-((O-Methyltetraethoxy)-oxycarbonylmethyl)-(D)-cyclohexylalanyl-3,4-dehydroproline 4-amidino-2-thiazolylmethylamide diacetate Preparation took place in analogy to Example 20 by esterification of H$_2$C—CH$_2$-(Boc)-(D)-Cha-Pyr-NH—CH$_2$-2-(4 am))-thiaz with tetraethylene glycol monomethyl ether and subsequent purification of the crude product by RP-HPLC (acetonitrile, water, acetic acid gradient).

FAB-MS (M+H$^+$): 653

Example 24

N-(Cyclohexyloxycarbonylmethyl)-(D)-cyclohexylalanyl-3,4-dehydroproline 4-hydroxyamidino-2-thiazolylmethylamide hydrochloride a) Boc-2-aminomethyl-thiazole-4-carboxamide

Ethyl bromopyruvate (386 g, 1.98 mol) was added dropwise to a solution of Boc-glycinethioamide (370 g, 1.94 mol) in 3.9 liters of ethanol at 10° C., and the mixture was then stirred at 20°–25° C. for 5 h. 299 ml of a 25% strength aqueous ammonia solution were then added. 940 ml of this mixture (corresponds to 19.9% of the total volume) were distilled to remove 380 ml of ethanol and, after addition of a further 908 ml of a 25% strength aqueous ammonia solution, stirred at 20 to 25° C. for 110 h. After cooling to 0° C., the solid was filtered off, washed twice with water and dried. 60.1 g of the Boc-protected thiazolecarboxamide were obtained with an HPLC purity of 97.9% area, corresponding to a yield over these two stages of 60.5%.

$^1$H-NMR (DMSO-d$_6$, in ppm): 8.16 (s, 1H, Ar—H), 7.86 (t, broad, 1H, NH), 7.71 and 7.59 (2× s, broad, 1H each, NH$_2$), 4.42 (d, 2H, CH$_2$), 1.41 (s, 9H, tert butyl)

b) 2-Aminomethyl-4-cyanothiazole hydrochloride

Boc-2-aminomethylthiazole-4-carboxamide (75.0 g, 0.29 mol) was suspended in 524 ml of methylene chloride and, at −5 to 0° C., triethylamine (78.9 g, 0.78 mol) and 79.5 g (0.38 mol) of trifluoroacetic anhydride were added. The mixture was stirred for 1 h and then allowed to warm to 20 to 25° C., 1190 ml of water were added and the phases were separated. 160 ml of 5-6N isopropanolic hydrochloric acid were added to the organic phase, which was boiled for 3 h, left to stir at 20°–25° C. overnight, cooled at −5 to 0° C. for 2.5 h and filtered to remove solid. This was washed with methylene chloride and dried. 48.1 g of 2-aminomethyl-4-cyanothiazole were obtained with an HPLC purity of 99.4% area, corresponding to a yield over these two stages of 94.3%.

$^1$H-NMR (DMSO-d$_6$, in ppm): 8.98 (s, broad, 2H, NH$_2$), 8.95 (s, 1H, Ar—H), 4.50 (s, 2H, CH$_2$)

c) 3,4-Dehydroproline 4-cyano-2-thiazolylmethylamide hydrochloride

Preparation took place in analogy to Example 1a) by coupling Boc-3,4-dehydroproline to 2-aminomethyl-4-cyanothiazole hydrochloride and then eliminating the protective group.

d) N-(tert-Butoxycarbonylmethyl)-(Boc)-(D)-cyclohexylalanyl-3,4-dehydroproline 4-cyano-2-thiazolylmethylamide Preparation took place in analogy to Example 1b) by coupling t-BuO$_2$C—CH$_2$-(Boc)-(D)-Cha-OH (WO 9806741) to H-Pyr-NH—CH$_2$-2-(4-CN)-thiaz hydrochloride.

e) N-(tert-Butoxycarbonylmethyl)-(Boc)-(D)-cyclohexylalanyl-3,4-dehydroproline 4-hydroxyamidino-2-thiazolylmethylamide t-BuO$_2$C—CH$_2$-(Boc)-(D)-Cha-Pyr-NH—CH$_2$-2-(4-CN)-thiaz (22.2 g, 36.7 mmol) was dissolved in ethanol (250 ml), and hydroxylamine hydrochloride (6.41 g, 92.2 mmol) was added and, while this suspension was cooled (waterbath), diisopropylethylamine (23.8 g, 31.6 ml, 184.5 mmol) was slowly added dropwise. The reaction solution was stirred at room temperature for 3 h and then concentrated in vacuo and taken up in methylene chloride/water, and the aqueous phase was adjusted to pH 3 with 2N hydrochloric acid and extracted. The organic phase was washed several times with water, dried over magnesium sulfate and concentrated in vacuo. The residue was extracted by stirring with n-hexane, resulting in 22.5 g of t-BuO$_2$C—CH$_2$-(Boc)-(D)-Cha-Pyr-NH—CH$_2$-2-(4-ham)-thiaz as an almost pure white solid.

f) N-(Cyclohexyloxycarbonylmethyl)-(D)-cyclohexylalanyl-3,4-dehydroproline 4-hydroxyamidino-2-thiazolylmethylamide hydrochloride t-BuO$_2$C—CH$_2$-(Boc)-(D)-Cha-Pyr-NH—CH$_2$-2-(4-ham)-thiaz (2.0 g, 3.15 mmol) was dissolved in cyclohexanol (25 ml) and, after addition of 10 ml of 5N hydrochloric acid in ether, stirred at 60° C. for 6 h.

Since TLC (methylene chloride/methanol/acetic acid: 100/20/5) showed that the reaction was not yet complete, a further 10 ml of 5N hydrochloric acid in ether were added, and the mixture was stirred at 60° C. for 4 h. Evaporation of the reaction mixture in vacuo was followed by codistillation several times with methylene chloride and ether to remove adherent hydrochloric acid. The product was then dissolved in a little methylene chloride and precipitated with ether, and the residue was filtered off with suction and dried in vacuo. 1.81 g of the title compound were obtained as a white hygroscopic solid.

FAB-MS (M+H$^+$): 561

Example 25

N-(Hexadecyloxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in hexadecanol/dioxane with 5M hydrochloric acid at 135° C., and the subsequent purification of the reaction mixture by column chromatography (silica gel/methylene chloride with increasing methanol content (0-10%)).

FAB-MS (M+H$^+$): 703

Example 26

N-(Undecyloxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in undecanol/dioxane with 5M hydrochloric acid at 65° C., and the subsequent purification of the reaction mixture by column chromatography (silica gel/methylene chloride with increasing methanol content (0–10%)).

FAB-MS (M+H$^+$): 633

Example 27

N-(Methoxyethoxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in ethylene glycol monomethyl ether/dioxane with 5M hydrochloric acid at 65° C., and the subsequent purification of the reaction mixture by column chromatography (silica gel/methylene chloride with increasing methanol content (0–10%)).

FAB-MS (M+H$^+$): 537

Example 28

N-((O-Methyldiethoxy)oxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in diethylene glycol monomethyl ether/dioxane with 5M hydrochloric acid at 65° C., and the subsequent purification of the reaction mixture by column chromatography (silica gel/methylene chloride with increasing methanol content (0–10%)).

FAB-MS (M+H$^+$): 581

Example 29

N-(Hexyloxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in hexanol/dioxane with 5M hydrochloric acid at 60° C., and precipitating the product from ether after concentration in vacuo.

FAB-MS (M+H$^+$): 563

Example 30

N-(Ethoxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in ethanol/dioxane with 5M hydrochloric acid at 60° C., and precipitating the product from ether after concentration in vacuo.

FAB-MS (M+H$^+$): 507

Example 31

N-(3-Fluoropropyloxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in 3-fluoropropanol/dioxane with 5M hydrochloric acid at 60° C., and precipitating the product from ether after concentration in vacuo.

FAB-MS (M+H$^+$): 539

Example 32

N-(Isopropyloxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in isopropanol/dioxane with 5M hydrochloric acid at 60° C., and precipitating the product from ether after concentration in vacuo.

FAB-MS (M+H$^+$): 521

Example 33

N-(3,3-Dimethylpropyloxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups and the transesterification/esterification of the carboxyl function in 3,3-dimethylpropyl alcohol/dioxane with 5M hydrochloric acid at 60° C., and precipitating the product from ether after concentration in vacuo.

FAB-MS (M+H$^+$): 549

Example 34

N-(Hydroxycarbonylmethyl)-(D)-cyclohexylalanyl-3,4-dehydroproline 4-hydroxyamidino-2-thiazolylmethylamide hydrochloride Preparation took place in analogy to Example 24, carrying out the elimination of the protective groups with 1M hydrochloric acid at 60° C. and precipitating the product from ether after concentration in vacuo.

FAB-MS (M+H$^+$): 479

Example 35

N-(Hydroxycarbonylmethyl)-N-(cyclohexyloxycarbonyl)-(D)-cyclohexylalanyl-3,4-dehydroproline 4-amidino-2-thiazolylmethylamide hydrochloride HO$_2$C—CH$_2$-(D)-Cha-Pyr-NH—CH$_2$-2-(4 am)-thiaz (0.5 g, 1.08 mmol; preparation: WO 9806741, Example 21) was suspended in a mixture of 2.5 ml of acetone and 2.5 ml of water, and cyclohexyl chloroformate (0.18 g, 1.08 mmol) and then, dropwise, diisopropylethylamine (0.14 g, 0.19 ml, 1.08 mmol) were added (pH 6–7), whereupon the precursor dissolved. After stirring at room temperature overnight, acetone was removed by distillation in vacuo, the residue was mixed with water, adjusted to pH 3 with dilute hydrochloric acid and extracted with methylene chloride, and the organic phase was dried over magnesium sulfate and concentrated in vacuo. The residue was dissolved in a little methylene chloride and precipitated with ether. 0.6 g of the title compound was obtained as a white solid.

FAB-MS (M+H$^+$): 589

Example 36

N-(Propyloxycarbonylmethyl)-(D)-cyclohexylalanyl-3,4-dehydroproline 4-(N-methoxycarbonyl)amidino-2-thiazolylmethylamide a) N-(tert-Butoxycarbonylmethyl)-(Boc)-(D)-cyclohexylalanyl-3,4-dehydroproline 4-amidino-2-thiazolylmethylamide t-BuO$_2$C—CH$_2$-(Boc)-(D)-Cha-Pyr-NH—CH$_2$-2-(4-CN)-thiaz (2.0 g, 3.3 mmol, Example 24d)) was dissolved in methanol (20 ml) and, after addition of N-acetyl-L-cysteine (0.6 g, 3.66 mmol), refluxed while passing in ammonia until the precursor had completely reacted (about 12 h, TLC check: methylene chloride/methanol: 95/5 and methylene chloride/methanol/acetic acid: 100/20/5). The reaction solution was concentrated in vacuo, the residue was taken up in dilute hydrochloric acid (pH 3) and extracted with ether, the aqueous phase was made alkaline with dilute sodium hydroxide solution (pH 9) and extracted with methylene chloride, and this organic phase was dried over magnesium sulfate and concentrated in vacuo. This resulted in 1.8 g of the title compound as a white solid.

b) N-(tert-Butoxycarbonylmethyl)-(Boc)-(D)-cyclohexylalanyl-3,4-dehydroproline 4-(N-methoxycarbonyl)amidino-2-thiazolylmethylamide The crude product obtained in a), t-BuO$_2$C—CH$_2$-(Boc)-(D)-Cha-Pyr-NH—CH$_2$-2-(4-C=NH(NH$_2$))-thiaz (2.0 g, 3.32 mmol) was dissolved in 50 ml of methylene chloride, and diisopropylamine (4.2 g, 32.32 mmol) was added and then, while cooling with a waterbath, methyl chloroformate (0.34 g, 3.56 mmol) in 5 ml of methylene chloride was added dropwise, and the mixture was stirred at room temperature for 1 h. The residue after concentration in vacuo was mixed with n-hexane, water and dilute hydrochloric acid (pH 3), and extracted, the aqueous phase was then extracted with ethyl acetate, and the ethyl acetate phase was dried over magnesium sulfate and concentrated in vacuo. 2.0 g of crude title compound were obtained as a colorless foam, which was reacted further without further purification.

c) N-(Propyloxycarbonylmethyl)-(D)-cyclohexylalanyl-3,4-dehydroproline 4-(N-methoxycarbonyl)amidino-2-thiazolylmethylamide The crude product obtained in b), t-BuO$_2$C—CH$_2$-(Boc)-(D)-Cha-Pyr-NH—CH$_2$-2-(4-C=NH(NH—COOCH$_3$))-thiaz (2.0 g, 2.95 mmol), was dissolved in a mixture of 35 ml of n-propanol and 20 ml of 4.5N hydrochloric acid in ether and stirred with exclusion of moisture overnight. The reaction solution was concentrated in vacuo, the residue was taken up in water and rapidly extracted with ethyl acetate, the aqueous phase was treated with alkali to pH 7 and extracted several times with ethyl acetate, and these ethyl acetate phases were dried over magnesium sulfate and concentrated in vacuo. Purification of the product by column chromatography on silica gel (short column, diluent: methylene chloride with increasing methanol content) resulted in 1.4 g of the title compound as a white solid.

FAB-MS (M+H$^+$): 563

Example 37

N-(Cyclohexyloxycarbonylmethyl)-(D)-cyclohexylalanyl-3,4-dehydroproline 4-(N-methoxycarbonyl)amidino-2-thiazolylmethylamide Preparation took place in analogy to Example 36c) from t-BuO$_2$C—CH$_2$-(Boc)-(D)-Cha-Pyr-NH—CH$_2$-2-(4-C=NH(NH—COOCH$_3$))-thiaz by elimination of protective groups and subsequent transesterification/esterification of the carboxyl function in cyclohexanol with 4.5M hydrochloric acid in ether.

FAB-MS (M+H$^+$): 603

Example 38

N-(Methoxycarbonylmethyl)-(D)-cyclohexylalanyl-3,4-dehydroproline 4-(N-methoxycarbonyl)amidino-2-thiazolylmethylamide Preparation took place in analogy to Example 36c) from t-BuO$_2$C—CH$_2$-(Boc)-(D)-Cha-Pyr-NH—CH$_2$-2-(4-C=NH(NH—COOCH$_3$))-thiaz by elimination of protective groups and subsequent transesterification/esterification of the carboxyl function in methanol with 4.5 M hydrochloric acid in ether.
FAB-MS (M+H$^+$): 535

Example 39

N-(Methoxycarbonylmethyl)-(D)-cyclohexylalanyl-3,4-dehydroproline 4-(N-cyclohexyloxycarbonyl)amidino-2-thiazolylmethylamide Preparation took place in analogy to Example 36b) and c) from t-BuO$_2$C—CH$_2$-(Boc)-(D)-Cha-Pyr-NH—CH$_2$-2-(4-C=NH(NH$_2$))-thiaz by reaction with cyclohexyl chloroformate and subsequent elimination of protective groups and transesterification/esterification of carboxyl function in methanol.
FAB-MS (M+H$^+$): 603

Example 40

N-(tert-Butyloxycarbonylmethyl)-(D)-cyclohexylalanyl-3,4-dehydroproline 4-hydroxyamidino-2-thiazolylmethylamide a) (D)-cyclohexylalanyl-3,4-dehydroproline 4-cyano-2-thiazolylmethylamide H-Pyr-NH—CH$_2$-2-(4-CN)-thiaz-hydrochloride (Example 24c) and Boc-(D)-Cha-OH were reacted in analogy to Example 1b) to give Boc-(D)-Cha-Pyr-NH—CH$_2$-2-(4-CN)-thiaz, and the Boc protective group was then eliminated with hydrochloric acid in isopropanol, resulting in H-(D)-Cha-Pyr-NH—CH$_2$-2-(4-CN)-thiaz hydrochloride as a white solid. The product was converted into the base H-(D)-Cha-Pyr-NH—CH$_2$-2-(4-CN)-thiaz in analogy to Example 17b) with ammonia in methylene chloride.

b) N-(tert-Butyloxycarbonylmethyl)-(D)-cyclohexylalanyl-3,4-dehydroproline 4-cyano-2-thiazolylmethylamide The product obtained in a), H-(D)-Cha-Pyr-NH—CH$_2$-2-(4-CN)-thiaz, was converted in analogy to Example 17b) by alkylation with bromoacetic acid into t-BuO$_2$C—CH$_2$-(D)-Cha-Pyr-NH—CH$_2$-2-(4-CN)-thiaz.

c) N-(tert-Butyloxycarbonylmethyl)-(D)-cyclohexylalanyl-3,4-dehydroproline 4-hydroxyamidino-2-thiazolylmethylamide The product obtained in b), t-BuO$_2$C—CH$_2$-(D)-Cha-Pyr-NH—CH$_2$-2-(4-CN)-thiaz, and hydroxylamine were reacted in analogy to Example 24e) to give t-BuO$_2$C—CH$_2$-(D)-Cha-Pyr-NH—CH$_2$-2-(4-ham)-thiaz.
FAB-MS (M+H$^+$): 535

Example 41

N-(Adamantyloxycarbonylmethyl)-(D)-cyclohexylalanyl-3,4-dehydroproline 4-hydroxyamidino-2-thiazolylmethylamide a) Adamantyl bromoacetate 1-Adamantol (3.0 g, 20.0 mmol) was dissolved in 30 ml of methylene chloride and, after addition of pyridine (9.5 g, 9.6 ml, 120 mmol) and cooling to −10° C., bromoacetyl bromide (4.4 g, 22.0 mmol) in 15 ml of methylene chloride was added dropwise to this solution with stirring. Warming to room temperature (2 h) was followed by addition of aqueous citric acid solution (pH 2) and extraction, and the organic phase was washed with water, dried over magnesium sulfate and concentrated in vacuo. The resulting crude product Ada-O$_2$C—CH$_2$—Br was employed without further purification in the subsequent alkylation.)

b) N-(Adamantyloxycarbonylmethyl)-(D)-cyclohexylalanyl-3,4-dehydroproline 4-cyano-2-thiazolylmethylamide Ada-O$_2$C—CH$_2$-(D)-Cha-Pyr-NH—CH$_2$-2-(4-CN)-thiaz was prepared in analogy to Example 40 starting from H-(D)-Cha-Pyr-NH—CH$_2$-2-(4-CN)-thiaz and Ada-O$_2$C—CH$_2$—Br.

c) N-(Adamantyloxycarbonylmethyl)-(D)-cyclohexylalanyl-3,4-dehydroproline 4-hydroxyamidino-2-thiazolylmethylamide Ada-O$_2$C—CH$_2$-(D)-Cha-Pyr-NH—CH$_2$-2-(4-ham)-thiaz was prepared in analogy to Example 24e) starting from Ada-O$_2$C—CH$_2$-(D)-Cha-Pyr-NH—CH$_2$-2-(4-CN)-thiaz and hydroxylamine.
FAB-MS (M+H$^+$): 613

Example 42

N-(Adamantyloxycarbonylmethyl)-(D)-cyclohexylalanyl-3,4-dehydroproline 4-amidino-2-thiazolylmethylamide diacetate Ada-O$_2$C—CH$_2$-(D)-Cha-Pyr-NH—CH$_2$-2-(4-CN)-thiaz (Example 41b) was converted in analogy to Example 36a) with ammonia and acetylcysteine into Ada-O$_2$C—CH$_2$-(D)-Cha-Pyr-NH—CH$_2$-2-(4-am)-thiaz and the resulting crude product was purified by RP-HPLC.
FAB-MS (M+H$^+$): 597

Example 43

N-(Hydroxyethyl)-(D)-cyclohexylalanyl-3,4-dehydroproline 4-hydroxyamidino-2-thiazolylmethylamide hydrochloride a) N-(Hydroxyethyl)-(D)-cyclohexylalanyl-3,4-dehydroproline 4-cyano-2-thiazolylmethylamide H-(D)-Cha-Pyr-NH—CH$_2$-2-(4-CN)-thiaz (4.0 g, 10.3 mmol, Example 40a)) was stirred together with iodoethanol (1.5 ml) in an oil bath at 100° C. for 5 h. Since TLC (methylene chloride/methanol/acetic acid: 100/20/5) showed precursor still present, the mixture was cooled and the base was liberated with ammoniacal methylene chloride solution, and the reaction mixture was again heated at 100° C. with iodoethanol (1.5 ml) for 2 h. Volatiles were then removed in vacuo, and the residue was extracted by stirring with ether three times. 5.3 g of the title compound were obtained as a pale yellow solid which was employed without further purification in the following reaction.)

b) N-(Hydroxyethyl)-(D)-cyclohexylalanyl-3,4-dehydroproline 4-hydroxyamidino-2-thiazolylmethylamide hydrochloride The crude product obtained in a), HO—$CH_2$—$CH_2$-(D)-Cha-Pyr-NH—$CH_2$-2-(4-CN)-thiaz, was converted in analogy to Example 24e) with hydroxylamine hydrochloride into the corresponding hydroxyamidine compound, which was then converted with hydrochloric acid in ether into the hydrochloride HO—$CH_2$—$CH_2$-(D)-Cha-Pyr-NH—$CH_2$-2-(4-ham)-thiaz hydrochloride.
FAB-MS (M+H$^+$): 465

Example 44

N-(Hydroxyethyl)-(D)-cyclohexylalanyl-3,4-dehydroproline 4-amidino-2-thiazolylmethylamide diacetate HO—$CH_2$—$CH_2$-(D)-Cha-Pyr-NH—$CH_2$-2-(4-CN)-thiaz (Example 43a) was reacted in analogy to Example 36a) with ammonia and N-acetyl-L-cysteine to give HO—$CH_2$—$CH_2$-(D)-Cha-Pyr-NH—$CH_2$-2-(4-am)-thiaz, and the resulting crude product was then purified by column chromatography (silica gel; methylene chloride/methanol/acetic acid: 80/20/1), resulting in the title compound as a colorless solid.
FAB-MS (M+H$^+$): 449

Example 45

N-(Hexyloxycarbonylmethyl)-(D)-cyclohexylalanyl-3,4-dehydroproline 4-(N-methoxyamidino)-2-thiazolylmethylamide hydrochloride a) N-(tert-Butoxycarbonylmethyl)-(Boc)-(D)-cyclohexylalanyl-3,4-dehydroproline 4-aminothiocarbonyl-2-thiazolylmethylamide t-$BuO_2$C—$CH_2$-(Boc)-(D)-Cha-Pyr-NH—$CH_2$-2-(4-CN)-thiaz (Example 24d)) was reacted in analogy to Example 1c) with hydrogen sulfide in pyridine/triethylamine to give the corresponding thioamide t-$BuO_2$C—$CH_2$-(Boc)-(D)-Cha-Pyr-NH—$CH_2$-2-(4-$CSNH_2$)-thiaz.

b) N-(tert-Butoxycarbonylmethyl)-(Boc)-(D)-cyclohexylalanyl-3,4-dehydroproline 4-methylthioiminomethyl-2-thiazolylmethylamide hydroiodide The product obtained from a), t-$BuO_2$C—$CH_2$-(Boc)-(D)-Cha-Pyr-NH—$CH_2$-2-(4-$CSNH_2$)-thiaz, was reacted in analogy to Example 1d) with methyl iodide to give t-$BuO_2$C—$CH_2$-(Boc)-(D)-Cha-Pyr-NH—$CH_2$-2-(4-C=NH($SCH_3$))-thiaz HI.

c) N-(tert-Butoxycarbonylmethyl)-(Boc)-(D)-cyclohexylalanyl-3,4-dehydroproline 4-(N-methoxyamidino)-2-thiazolylmethylamide The product obtained from b), t-$BuO_2$C—$CH_2$-(Boc)-(D)-Cha-Pyr-NH—$CH_2$-2-(4-C=NH($SCH_3$))-thiaz was reacted in analogy to Example 8a) with methoxylamine to give t-$BuO_2$C—$CH_2$-(Boc)-(D)-Cha-Pyr-NH—$CH_2$-2-(4-methoxyamidino)-thiaz.

d) N-(Hexyloxycarbonylmethyl)-(D)-cyclohexylalanyl-3,4-dehydroproline 4-(N-methoxyamidino)-2-thiazolylmethylamide hydrochloride The elimination of protective groups and the transesterification/esterification of the carboxyl function in t-$BuO_2$C—$CH_2$-(Boc)-(D)-Cha-Pyr-NH—$CH_2$-2-(4-C=NH($NHOCH_3$))-thiaz was carried out in analogy to Example 24f) in hexanol with 5M hydrochloric acid in ether at 60° C., and the resulting crude product was purified by extraction (methylene chloride/water) and subsequent precipitation from ether, resulting in the title compound as a white solid.
FAB-MS (M+H$^+$): 577

Example 46

N-(Ethoxycarbonylmethyl)-(D)-cyclohexylalanyl-3,4-dehydroproline 4-(N-methoxyamidino)-2-thiazolylmethylamide hydrochloride The elimination of protective groups and the transesterification/esterification of the carboxyl function in t-$BuO_2$C—$CH_2$-(Boc)-(D)-Cha-Pyr-NH—$CH_2$-2-(4-C=NH($NHOCH_3$))-thiaz was carried out in analogy to Example 24f) in ethanol with 5M hydrochloric acid in ether at 60° C., and the resulting crude product was purified by extraction (methylene chloride/a little water) and subsequent precipitation from ether, resulting in the title compound as a white solid.
FAB-MS (M+H$^+$): 521

Example 47

N-(Cyclohexyloxycarbonylmethyl)-(D)-cyclohexylalanyl-3,4-dehydroproline 4-(N-methoxyamidino)-2-thiazolylmethylamide hydrochloride The elimination of protective groups and the transesterification/esterification of the carboxyl function in t-$BuO_2$C—$CH_2$-(Boc)-(D)-Cha-Pyr-NH—$CH_2$-2-(4-C=NH($NHOCH_3$))-thiaz was carried out in analogy to Example 24f) in cyclohexanol with 5M hydrochloric acid in ether at 60° C., and the resulting crude product was purified by extraction (methylene chloride/a little water) and subsequent precipitation from ether, resulting in the title compound as a white solid.
FAB-MS (M+H$^+$): 575

Example 48

N-(Hydroxycarbonylmethyl)-(D)-cyclohexylalanyl-3,4-dehydroproline 4-(1,2,4-oxadiazol-5-on-3-yl)-2-thiazolylmethylamide hydrochloride Preparation took place starting from t-$BuO_2$C—$CH_2$-(Boc)-(D)-Cha-Pyr-NH—$CH_2$-2-(4-ham)-thiaz (Example 24d) in analogy to Example 18), resulting in the title compound as a white amorphous powder.
FAB-MS (M+H$^+$): 505

Example 49

N-(Methoxycarbonylmethyl)-(D)-cyclohexylalanyl-3,4-dehydroproline 4-(1,2,4-oxadiazol-5-on-3-yl)-2-thiazolylmethylamide hydrochloride Preparation took place starting from t-BuO$_2$C—CH$_2$-(Boc)-(D)-Cha-Pyr-NH—CH$_2$-2-(4-ham)-thiaz (Example 24d) in analogy to Example 19), resulting in the title compound as a white amorphous powder.

FAB-MS (M+H$^+$): 519

Example 50

N-(Hydroxycarbonylmethyl)-(D)-cyclohexylglycyl-3,4-dehydroproline 4-(N-tert-butyloxycarbonylmethyleneamidino)-2-thienylmethylamide hydrochloride This compound was prepared by dissolving 2.47 g (3.24 mmol) of the product obtained in 13c), N-(tert-butoxycarbonylmethyl)-(Boc)-(D)-cyclohexylglycyl-3,4-dehydroproline 4-methylthioiminomethyl-2-thienylmethylamide hydroiodide, in 40 ml of methanol and, at room temperature, adding 2.86 g (19.43 mmol) of tert-butyl aminoxyacetate, and heating at 40° C. for 20 min. The residue after concentration was taken up in ethyl acetate and washed twice with 10% strength sodium thiosulfate solution and once each with 20% strength sodium bisulfate solution and saturated sodium chloride solution. The residue (2.5 g) after drying over magnesium sulfate and concentrating the solution was purified by column chromatography (eluent: hexane/ethyl acetate 1:1). 2.3 g of a yellowish oil were obtained. The protective groups were eliminated with dioxane/HCl at room temperature within three hours.

FAB-MS (M+H$^+$): 522

Example 51

N-(n-Hexyloxycarbonylmethyl)-(D)-cyclohexylgycyl-3,4-dehydroproline 5-(3-hydroxyamidino)thienylmethylamide 10 ml (40 mmol) of a 4 molar solution of hydrogen chloride in 1,4-dioxane were added to a solution of 2.5 g (4 mmol) of the product N-(tert-butoxycarbonylmethyl)-(N-Boc)-(D)-cyclohexylglycyl-3,4-dehydroproline 5-(3-hydroxyamidino)thienylmethylamide obtained according to Example 18a in 25 ml 1-hexanol and the reaction mixture was heated to 40° C. The reaction mixture was stirred for 8 hours at this temperature and overnight at room temperature. Although no complete conversion was observed, the reaction mixture was concentrated to dryness on a rotary evaporator, was taken up in diethyl ether and stirred. The precipitate was filtered off, washed with ether, dissolved in methanol and transferred into the acitic acid salt via an ion exchange. The residue was purified by column chromatography (normal phase-MPLC, eluent: dichloromethane/methanol=95:5). 1.8 g (73%) of the title compound were obtained as a white solid.

ESI-MS (M+H$^+$): 548

Example 52

N-(Ethoxycarbonylmethyl)-(D)-cyclohexylglycyl-3,4-dehydroproline 5-(3-hydroxyamidino)thienylmethylamide 10 ml (40 mmol) of a 4 molar solution of hydrogen chloride in 1,4-dioxane were added to a solution of 2.5 g (4 mmol) of the product N-(tert-butoxycarbonylmethyl)-(N-Boc)-(D)-cyclohexylglycyl-3,4-dehydroproline 5-(3-hydroxyamidino)thienylmethylamide obtained according to Example 18a in 25 ml ethanol and the reaction mixture was heated to 40° C. The reaction mixture was stirred for 8 hours at this temperature and overnight at room temperature. Although no complete conversion was observed, the reaction mixture was concentrated to dryness on a rotary evaporator, was taken up in diethyl ether and stirred. The precipitate was filtered off, washed with ether, dissolved in methanol and transferred into the acetic acid salt using an ion exchanger. The residue was purified by column chromatography (normal phase-MPLC, eluent: dichloromethane/methanol=95:5). 0.59 g (27%) of the title compound were obtained as a white solid.

ESI-MS (M+H$^+$): 492

Example 53

N-(Cyclopentyloxycarbonylmethyl)-(D)-cyclohexylglycyl-3,4-dehydroproline 5-(3-hydroxyamidino)thienylmethylamide 10 ml (40 mmol) of a 4 molar solution of hydrogen chloride in 1,4-dioxane were added to a solution of 2.5 g (4 mmol) of the product N-(tert-butoxycarbonylmethyl)-(N-Boc)-(D)-cyclohexylglycyl-3,4-dehydroproline 5-(3-hydroxyamidino)thienylmethylamide obtained according to Example 18a in 25 ml cyclopentanol and the reaction mixture was heated to 40° C. The reaction mixture was stirred for 2 days at this temperature. Although no complete conversion was observed, the reaction mixture was concentrated to dryness on a rotary evaporator, was taken up in diethyl ether and stirred. The precipitate was filtered off, washed with ether, dissolved in methanol and transferred into the acetic acid salt using an ion exchanger. The residue was purified by column chromatography (normal phase-MPLC, eluent: ethyl acetate/n-hexane=8:2). 1.38 g (58%) of the title compound was obtained as a white solid.

ESI-MS (M+H$^+$): 532

Example 54

N-(Cyclohexyloxycarbonylmethyl)-(D)-cyclohexylglycyl-3,4-dehydroproline 5-(3-hydroxyamidino)thienylmethylamide Preparation took place by using t-BuO$_2$C—CH$_2$—(Boc)-(D)-Chg-Pyr-NH—CH$_2$-5-(3-ham)-thioph (Example 18a) and cyclohexanol in analogy to Example 53, whereby the title compound was obtained as a white amorphous powder.

ESI-MS (M+H$^+$): 546

Example 55

N-(Cyclopropylmethyloxycarbonylmethyl)-(D)-cyclohexylalanyl-3,4-dehydroproline 2-(4-hydroxyamidino)thiazolylmethylamide hydrochloride Preparation took place in analogy to Example 53, starting from N-(hydroxycarbonylmethyl)-(D)-cyclohexylalanyl-3,4-dehydroproline 2-(4-hydroxyamidino)thiazolylmethylamide hydrochloride (Example 34) and cyclopropyl methanol, whereby the title compound was obtained as a white amorphous powder.
ESI-MS (M+H$^+$): 533

Example 56

N-(Cyclopentyloxycarbonylmethyl)-(D)-cyclohexylalanyl-3,4-dehydroproline 2-(4-hydroxyamidino)thiazolylmethylamide hydrochloride Preparation took place in analogy to Example 53, starting from N-(hydroxycarbonylmethyl)-(D)-cyclohexylalanyl-3,4-dehydroproline 2-(4-hydroxyamidino)thiazolylmethylamide hydrochloride (Example 34) and cyclopentanol, whereby the title compound was obtained as a white amorphous powder.
ESI-MS (M+H$^+$): 547

Example 57

N-(5-Methyl-2-oxo-1,3-dioxol-4-yl)methyloxycarbonylmethyl-(D)-cyclohexylalanyl-3,4-dehydroproline 2-(4-hydroxyamidino)-thiazolylmethylamide hydrochloride a) 4-Bromomethyl-5-methyl-2-oxo-1,3-dioxolon 4-Bromomethyl-5-methyl-2-oxo-1,3-dioxolon was prepared according to Sakamoto, Ikeda and Tsukamoto (Chem. Pharm. Bull. 1984, 32, 6, 2241–2248) via radical bromination from 11.4 g 4,5-dimethyl-2-oxo-1,3-dioxolon and 17.6 g bromine.

b) 4-Hydroxymethyl-5-methyl-2-oxo-1,3-dioxolon

4-Bromomethyl-5-methyl-2-oxo-1,3-dioxolon obtained in a) was converted to the title compound via the formylester as the intermediate in analogy to Alexander et al. (J. Med. Chem. 1996, 39, 480–86).

c) Methyl 5-methyl-2-oxo-1,3-dioxolon-4-yl bromoacetate

4-Hydroxymethyl-5-methyl-2-oxo-1,3-dioxolon (0.44 g, 3.4 mmol) was dissolved in 5 ml dichloromethane mixed with pyridine (0.27 g, 0.3 ml, 3.4 mmol), cooled to 0° C. and subsequently bromoacetic acid bromide (0.68 g, 3.4 mmol) dissolved in 3 ml dichloromethane was added dropwise whilst stirring. The reaction mixture was diluted with ethyl acetate after warming to room temperature (1.5 h) and was extracted several times with a little water to separate pyridine. The combined organic extracts were dried over magnesium sulphate and concentrated in vacuo after filtering off the drying agent. The obtained crude product 1,3-Dioxol-2-on-4-yl-O$_2$C—CH$_2$—Br was used without further purification in the subsequent alkylation.

d) N-(5-Methyl-2-oxo-1,3-dioxol-4-yl)methyloxycarbonylmethyl-(D)-cyclohexylalanyl-3,4-dehydroproline 2-(4-cyano)-thiazolylmethylamide Starting from H-(D)-Cha-Pyr-NH—CH$_2$-2-(4-CN)-thiaz and 1,3-dioxol-2-on-4-yl-O$_2$C—CH$_2$—Br, 1,3-dioxol-2-on-4-yl-O$_2$C—CH$_2$-(D)-Cha-Pyr-NH—CH$_2$-2-(4-CN)-thiaz was prepared in analogy to Example 40.

e) N-(5-Methyl-2-oxo-1,3-dioxol-4-yl)methyloxycarbonylmethyl-(D)-cyclohexylalanyl-3,4-dehydroproline 2-(4-hydroxyamidino)-thiazolylmethylamide Starting from 1,3-dioxol-2-on-4-yl-O$_2$C—CH$_2$-(D)-Cha-Pyr-NH—CH$_2$-2-(4-CN)-thiaz and hydroxylamine, 1,3-dioxol-2-on-4-yl-O$_2$C—CH$_2$-(D)-Cha-Pyr-NH—CH$_2$-2-(4-ham)-thiaz was prepared in analogy to Example 24e).
ESI-MS (M+H$^+$): 591

Example 58

N-(Hydroxycarbonylmethyl)-N-(methyloxycarbonyl)-(D)-cyclohexylalanyl-3,4-dehydroproline 2-(4-amidino)thiazolylmethylamide hydrochloride Preparation took place in analogy to Example 35, starting from HO$_2$C—CH$_2$-(D)-Cha-Pyr-NH—CH$_2$-2-(4-am)-thiaz and methyl chloroformiate whereby the title compound was obtained as a white amorphous powder.
FAB-MS (M+H$^+$): 521

Example 59

N-(Hydroxycarbonylmethyl)-N-(hexyloxycarbonyl)-(D)-cyclohexylalanyl-3,4-dehydroproline 2-(4-amidino)thiazolylmethylamide hydrochloride Preparation took place in analogy to Example 35, starting from HO$_2$C—CH$_2$-(D)-Cha-Pyr-NH—CH$_2$-2-(4-am)-thiaz and hexyl chloroformiate whereby the title compound was obtained as a white amorphous powder.
FAB-MS (M+H$^+$): 591

Example 60

N-(Methoxyethoxycarbonylmethyl)-(D)-cyclohexylalanyl-3,4-dehydroproline 2-(4-amidino)thiazolylmethylamide dihydrochloride Preparation took place in analogy to Example 20 by esterification of HO$_2$C—CH$_2$-(Boc)-(D)-Cha-Pyr-NH—CH$_2$-2-(4-am)-thiaz with ethyleneglycol monomethyl ether whereby the conversion took place at about 60-65° C. and the subsequent purification of the reaction mixture was conducted using column chromatography (silica gel/dichloromethane with increasing amount of methanol).
FAB-MS (M+H$^+$): 521

Example 61

N-((O-Methyldiethoxy)-oxycarbonylmethyl)-(D)-cyclohexylalanyl-3,4-dehydroproline 2-(4-amidino)thiazolylmethylamide dihydrochloride Preparation took place in analogy to Example 20 by esterification of HO$_2$C—CH$_2$-(Boc)-(D)-Cha-Pyr-NH—CH$_2$-2-(4-am)-thiaz with diethyleneglycol monomethyl ether whereby the conversion took place at about 60–65° C. After exchanging the chloride ions with acetate ions using an ion exchanger, the purification of the reaction mixture was conducted using HPLC (RP Phase, Lyophilising the aqueous solution with addition of hydrochloric acid) and the product was obtained as a white solid.
FAB-MS (M+H$^+$): 565

Example 62

N-(6-Aminohex-1-yl-oxycarbonylmethyl)-(D)-cyclohexylalanyl-3,4-dehydroproline 2-(4-amidino)thiazolylmethylamide×acetic acid Preparation of BOC-NH—$(CH_2)_6$—$O_2C$—$CH_2$-(D)-Cha-Pyr-NH—$CH_2$-2-(4-CN)-thiaz took place at first in analogy to Example 41a, by conversion of BOC-NH—$(CH_2)_6$—OH with bromoacetic acid bromide to BOC-NH—$(CH_2)_6$—OCO—$CH_2$—Br which was subsequently used in an analogy to Example 17b or 40b, respectively, in the alkylation with H-(D)-Cha-Pyr-NH—$CH_2$-2-(4-CN)-thiaz. After conversion of the obtained intermediate BOC-NH—$(CH_2)_6$—$O_2C$—$CH_2$-(D)-Cha-Pyr-NH—$CH_2$-2-(4-CN)-thiaz with $(BOC)_2O$ to BOC-NH—$(CH_2)_6$—$O_2C$—$CH_2$-(BOC)-(D)-Cha-Pyr-NH—$CH_2$-2-(4-CN)-thiaz, the nitrile function was converted to the amidine function in an analogy to WO 9806741. After removal of the protecting group with hydrochloric acid in dioxane, exchange of the chloride ions with acetate ions using an ion exchanger and subsequent chromatographic purification (HPLC: RP phase, lyophilising the aqueous solution) the title compound $H_2N$—$(CH_2)_6$—$O_2C$—$CH_2$ (D)-Cha-Pyr-NH—$CH_2$-2-(4-am)-thiaz×$CH_3COOH$ was obtained as a white powder.

FAB-MS (M+H$^+$): 562

Example 63

N-(Decahydro-2-naphthyloxycarbonylmethyl)-(D)-cyclohexylalanyl-3,4-dehydroproline 2-(4-amidino)thiazolylmethylamide hydrochloride Preparation took place in analogy to Example 24, whereby the removal of the protecting groups and the transesterification/esterification of the carboxy function was conducted in decahydro-2-naphthol/dioxane with 5 M hydrochloric acid at 60° C. After concentrating in vacuo, the residue was stirred with ether to remove excess hydrochloric acid and alcohol, the residue was dissolved in aqueous potassium carbonate solution (pH 8), extracted several times with dichloromethane, the organic phases were dried over magnesium sulphate, etheral hydrochloric acid was added and the residue was concentrated. The residue was co-distilled several times with ether and subsequently stirred with ether whereby $C_{10}H_{17}$—$O_2C$—$CH_2$(D)-Cha-Pyr-NH—$CH_2$-2-(4-ham)-thiaz×HCl was obtained as a white solid substance.

FAB-MS (M+H$^+$): 615

Example 64

N-(Cyclohexylmethyloxycarbonylmethyl)-(D)-cyclohexylalanyl-3,4-dehydroproline 2-(4-amidino)thiazolylmethylamide hydrochloride Preparation took place in analogy to Example 24, whereby the removal of the protecting groups and the transesterification/esterification of the carboxy function was conducted in cyclohexylmethyl alcohol/dioxane with 5 M hydrochloric acid at 60° C. The work-up was conducted as described in Example 63, whereby $C_6H_{11}$—$CH_2$—$O_2C$—$CH_2$(D)-Cha-Pyr-NH—$CH_2$-2-(4-ham)-thiaz×HCl was obtained as a white solid substance.

FAB-MS (M+H$^+$): 575

Example 65

N-(4-tert-Butylcyclohexylcarbonylmethyl)-(D)-cyclohexylalanyl-3,4-dehydroproline 2-(4-amidino)thiazolylmethylamide hydrochloride Preparation took place in analogy to Example 24, whereby the removal of the protecting groups and the transesterification/esterification of the carboxy function was conducted in 4-tert-butyl cyclohexanol/dioxane with 5 M hydrochloric acid at 60° C. The work-up was conducted as described in Example 63, whereby 4-$(CH_3)_3C$—$C_6H_{10}$—$O_2C$—$CH_2$ (D)-Cha-Pyr-NH—$CH_2$-2-(4-ham)-thiaz×HCl was obtained as a white solid substance which according to HPLC or NMR is a mixture of 75% of the trans and 25% of the cis ester.

FAB-MS (M+H$^+$): 617

Example 66

N-(Adamant-1-ylmethyloxycarbonylmethyl)-(D)-cyclohexylalanyl-3,4-dehydroproline 2-(4-amidino)thiazolylmethylamide hydrochloride Preparation took place in analogy to Example 24, whereby the removal of the protecting groups and the transesterification/esterification of the carboxy function was conducted in adamantyl-1-methyl alcohol/dioxane with 5 M hydrochloric acid at 60° C. The work-up was conducted as described in Example 63, whereby $C_{10}H_{15}$—$CH_2$—$O_2C$—$CH_2$(D)-Cha-Pyr-NH—$CH_2$-2-(4-ham)-thiaz×HCl was obtained as a white substance.

FAB-MS (M+H$^+$): 627

Example 67

N-(4-tert-Butylcyclohexylmethyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in 4-tert-butyl cyclohexylmethyl alcohol/dioxane with 5 M hydrochloric acid at 60° C. The work-up was conducted as described in Example 63, whereby 4-$(CH_3)_3C$—$C_6H_{10}$—$CH_2$—$O_2C$—$CH_2$(D)-Cha-Pyr-NH—$CH_2$-2-(4-ham)-thiaz×HCl was obtained as a white solid substance.

FAB-MS (M+H$^+$): 631

Example 68

N-(4-Methoxycyclohexyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in 4-methoxy cyclohexanol/dioxane with 5 M hydrochloric acid at 60° C. The work-up was conducted as described in Example 63, whereby 4-$CH_3O$—$C_6H_{10}$—$O_2C$—$CH_2$(D)-Cha-Pyr-NH—$CH_2$-2-(4-ham)-thiaz×HCl was obtained as a white solid substance.

FAB-MS (M+H$^+$): 591

Example 69

N-(4-Cycloheptyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification was conducted in cycloheptanol/dioxane with 5 M hydrochloric acid at 60° C. The work-up was conducted as described in Example 63, whereby $C_7H_{13}$—$O_2C$—$CH_2$(D)-Cha-Pyr-NH—$CH_2$-2-(4-ham)-thiaz×HCl was obtained as a white solid substance.

FAB-MS (M+H$^+$): 575

Example 70

N-(3.3.5.5-Tetramethylcyclohexyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in 3.3.5.5-Tetramethyl cyclohexanol/dioxane with 5 M hydrochloric acid at 60° C. The work-up was conducted as described in Example 63, whereby 3.3.5.5-$(CH_3)_4$—$C_6H_{10}$—$O_2C$—$CH_2$(D)-Cha-Pyr-NH—$CH_2$-2-(4-ham)-thiaz×HCl was obtained as a white solid substance.

FAB-MS (M+H$^+$): 617

Example 71

N-(4-Pyranyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in 4-pyranylalcohol/dioxane with 5 M hydrochloric acid at 60° C. The work-up was conducted as described in Example 63, whereby 4-pyranyl-$O_2C$—$CH_2$(D)-Cha-Pyr-NH—$CH_2$-2-(4-ham)-thiaz×HCl was obtained as a white solid substance.

FAB-MS (M+H$^+$): 563

Example 72

N-(Methyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in methanol/dioxane with 5 M hydrochloric acid at 60° C. $CH_3$—$O_2C$—$CH_2$(D)-Cha-Pyr-NH—$CH_2$-2-(4-ham)-thiaz×HCl was obtained as a white solid substance by stirring with ether.

FAB-MS (M+H$^+$): 493

Example 73

N-(n-Propyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in propanol/dioxane with 5 M hydrochloric acid at 60° C. After stirring with ether $CH_3$—$CH_2$—$CH_2$—$O_2C$—$CH_2$(D)-Cha-Pyr-NH—$CH_2$-2-(4-ham)-thiaz×HCl was obtained as a white solid substance.

FAB-MS (M+H$^+$): 521

Example 74

N-(n-Butyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in n-butanol/dioxane with 5 M hydrochloric acid at 60° C. After stirring with ether $CH_3$—$CH_2$—$CH_2$—$CH_2$—$O_2C$—$CH_2$(D)-Cha-Pyr-NH—$CH_2$-2-(4-ham)-thiaz×HCl was obtained as a white solid substance.

FAB-MS (M+H$^+$): 535

Example 75

N-(i-Butyloxycarbonylmethyl)-(D)-cyclohexylalanyl-3,4-dehydroproline 2-(4-hydroxyamidino)thiazolylmethylamide hydrochloride Preparation took place in analogy to Example 24, whereby the removal of the protecting groups and the transesterification/esterification of the carboxy function was conducted in iso-butanol/dioxane with 5 M hydrochloric acid at 60° C. After stirring with ether $CH_3$—$CH(CH_3)$—$CH_2$—$O_2C$—$CH_2$(D)-Cha-Pyr-NH—$CH_2$-2-(4-ham)-thiaz×HCl was obtained as a white solid substance.

FAB-MS (M+H$^+$): 535

Example 76

N-(2.4-Dimethylpent-3-yloxycarbonylmethyl)-(D)-cyclohexylalanyl-3,4-dehydroproline 2-(4-hydroxyamidino)thiazolylmethylamide a) 2.4-Dimethylpent-3-yl bromoacetate 2.4-dimethylpentan-3-ol (4.0 g, 4.8 ml, 34.4 mmol), n-pentane (40 ml) and pyridine (16.3 g, 16.6 ml, 206.5 mmol) were placed in a flask, cooled to −10° C. and bromoacetyl bromide (9.0 g, 3.9 ml, 44.75 mmol) was slowly added to the solution. After stirring for 5 h at room temperature more pentane was added, the organic solution was subsequently dried over a magnesium sulphate and carefully concentrated in vacuo. 7.2 g of $[(CH_3)_2CH]_2CH$—$O_2C$—$CH_2$—Br was obtained as a colorless liquid.

b) [(CH₃)₂CH]₂CH—O₂C—CH₂(D)-Cha-Pyr-NH—CH₂-2-(4-ham)-thiaz

H-(D)-Cha-Pyr-NH—CH₂-2-(4-CN)-thiaz (Example 40a) was alkylated in analogy to Example 40b with [(CH₃)₂CH]₂CH—O₂C—CH₂—Br to [(CH₃)₂CH]₂CH—O₂C—CH₂(D)-Cha-Pyr-NH—CH₂-2-(4-CN)-thiaz and subsequently converted with hydroxylamine in analogy to Example 24e to [(CH₃)₂CH]₂CH—O₂C—CH₂(D)-Cha-Pyr-NH—CH₂-2-(4-ham)-thiaz. After concentrating the reaction mixture in vacuo, the residue was taken up in dichloromethane, extracted with a solution of hydrochloric acid (pH 1–2), the aqueous phase containing the title compound was subsequently set to pH 5 and again extracted with dichloromethane. After drying over magnesium sulphate and concentrating the solution in vacuo, [(CH₃)₂CH]₂CH—O₂C—CH₂(D)-Cha-Pyr-NH—CH₂-2-(4-ham)-thiaz was obtained as a white solid substance.
FAB-MS (M+H⁺): 577

Example 77

N-(1-Methylcyclopentyloxycarbonylmethyl)-(D)-cyclohexylalanyl-3,4-dehydroproline 2-(4-hydroxyamidino)thiazolylmethylamide 1-Methylcyclopentyl bromoacetate prepared in analogy to 76a was converted with H-(D)-Cha-Pyr-NH—CH₂-2-(4-CN)-thiaz (Example 40a) to (1-CH₃)C₅H₈—O₂C—CH₂(D)-Cha-Pyr-NH—CH₂-2-(4-CN)-thiaz which was in turn subsequently converted to (1-CH₃)C₅H₈—O₂C—CH₂(D)-Cha-Pyr-NH—CH₂-2-(4-ham)-thiaz in analogy to Example 24e. The isolation of the product was conducted in analogy to Example 76b.
FAB-MS (M+H⁺): 561

Example 78

N-(áá-Dicyclohexylmethyloxycarbonylmethyl)-(D)-cyclohexylalanyl-3,4-dehydroproline 2-(4-hydroxyamidino)thiazolylmethylamide áá-Dicyclohexylmethyl bromoacetate prepared in analogy to 76a was converted with H-(D)-Cha-Pyr-NH—CH₂-2-(4-CN)-thiaz (Example 40a) to $(C_6H_{11})_2$CH—O₂C—CH₂(D)-Cha-Pyr-NH—CH₂-2-(4-CN)-thiaz which in turn was subsequently converted to $(C_6H_{11})_2$CH—O₂C—CH₂(D)-Cha-Pyr-NH—CH₂-2-(4-ham)-thiaz in analogy to Example 24e. The isolation of the product was conducted in analogy to Example 76b.
FAB-MS (M+H⁺): 657

Example 79

N-(tert-Butylaminocarbonylmethyl)-(D)-cyclohexylalanyl-3,4-dehydroproline 2-(4-hydroxyamidino)thiazolylmethylamide a) N-(Hydroxycarbonylmethyl)-(D)-cyclohexylalanyl-3,4-dehydroproline 2-(4-cyano)thiazolylmethylamide (CH₃)₃C—O₂C—CH₂-(BOC)-(D)-Cha-Pyr-NH—CH₂-2-(4-CN)-thiaz (7.0 g, 11.6 mmol; Example 24d) was dissolved in dichloromethane (70 ml), dioxane/hydrochloric acid (14.4 ml, 4 M) was added and the mixture was stirred overnight at room temperature. The intermediate which had formed an oil was taken from the walls of the flask and the mixture was again stirred for 4 h. Subsequently, the solution was concentrated in vacuo and co-distilled several times with ether. The product was purified by column chromatography (silica gel; eluent: dichloromethane with increasing amount of methanol).

b) N-(Hydroxycarbonylmethyl)-(BOC)-(D)-cyclohexylalanyl-3,4-dehydroproline 2-(4-cyano)thiazolylmethylamide HO₂C—CH₂-(D)-Cha-Pyr-NH—CH₂-2-(4-CN)-thiaz (4.2 g, 8.7 mmol; see a)) was suspended in dichloromethane (40 ml), diisopropyl ethylamine (11.3 g, 14.9 ml, 87.2 mmol) was added and (BOC)₂O (3.8 g, 54.5 mmol) in dichloromethane (5 ml) was dropwise added to the solution at room temperature. After stirring for 5 h at room temperature the conversion was complete (monitored by TLC). The reaction solution was concentrated in vacuo, aqueous hydochloric acid (pH 3) was added to the residue, the residue was extracted several times with ether, the organic phases were dried over magnesium sulphate and to the residue, the residue was extracted several times with ether, the organic phases were dried over magnesium sulphate and concentrated in vacuo, whereby the title compound was obtained as a white solid substance.

c) N-(tert-Butylaminocarbonylmethyl)-(BOC)-(D)-cyclohexylalanyl-3,4-dehydroproline 2-(4-cyano)thiazolylmethylamide HO₂C—CH₂-(BOC)-(D)-Cha-Pyr-NH—CH₂-2-(4-CN)-thiaz (1.0 g, 1.8 mmol; see b)) was dissolved together with tert-butylamine (5 ml, 47 mmol) in dichloromethane (47 ml), cooled to 5° C. and propylphosphonic acid anhydride solution in ethyl acetate (50% solution, 1.7 ml, 2.16 mmol) was slowly added at 5° C. After stirring for 1 h at 10° C. conversion was complete according to TLC analysis. The residue was concentrated in vacuo, taken up in ether, consecutively washed in water, 0.3 N hydrochloric acid and water, dried over magnesium sulphate and concentrated in vacuo, whereby the title compound was obtained as a white foam.

d) N-(tert-Butylaminocarbonylmethyl)-(D)-cyclohexylalanyl-3,4-dehydroproline 2-(4-hydroxyamidino)thiazolylmethylamide (CH₃)₃C—NH—CO—CH₂-(BOC)-(D)-Cha-Pyr-NH—CH₂-2-(4-CN)-thiaz was converted with hydroxylamine to (CH₃)₃C—NH—CO—CH₂-(BOC)-(D)-Cha-Pyr-NH—CH₂-2-(4-ham)-thiaz in analogy to Example 24e, from which the title compound was obtained as a white solid substance by removal of the protecting group with hydrochloric acid in dioxane/dichloromethane.
FAB-MS (M+H⁺): 534

Example 80

N-(n-Hexylaminocarbonylmethyl)-(D)-cyclohexylalanyl-3,4-dehydroproline 2-(4-hydroxyamidino)thiazolylmethylamide Preparation took place by coupling HO₂C—CH₂-(BOC)-(D)-Cha-Pyr-NH—CH₂-2-(4-CN)-thiaz (Example 79b) with n-hexylamine, subsequent conversion with hydroxylamine to CH₃—(CH₂)₅—NH—CO—CH₂-(BOC)-(D)-Cha-Pyr-NH—CH₂-2-(4-ham)-thiaz which by cleavage of the protection group was converted to CH₂—(CH₂)₃—NH—CO—CH₂—(D)—Cha-Pyr-NH—CH₂-(4-ham)-thiaz.

Example 81

N-(Hydroxyaminocarbonylmethyl)-(D)-cyclohexylalanyl-3,4-dehydroproline 2-(4-hydroxyamidino)thiazolylmethylamide CH₃—O₂C—CH₂(D)-Cha-Pyr-NH—CH₂-2-(4-ham)-thiaz×HCl (1.8 g, 3.4 mmol, Example 72), methanol (20 ml), hydroxylamine hdrochloride (3.6 g, 54 mmol) and diisopropyl ethylamine (10.5 g, 13.9 ml, 81 mmol) were stirred overnight at room temperature. After filtering the reaction mixture, concentrating under high vacuum (preferably complete removal of diisopropyl ethylamine), dissolving the residue in water, the reaction mixture was converted into the acetate using an ion exchange column. The later fractions contained the desired product with only a little content of diisopropyl ethylammonium acetate which was removed by lyophilisation of the solution. HONH—OC—CH₂-(D)-Cha-Pyr-NH—CH₂-2-(4-ham)-thiaz (1.0 g) was obtained as a white solid substance.

FAB-MS (M+H⁺): 494

Example 82

N-(Hydroxycarbonylmethyl)-(D)-cyclohexylalanyl-3,4-dehydroproline 2-(4-hydroxyamidino)thienylmethylamide hydrochloride Preparation took place starting from (CH₃)₃C—O₂C—CH₂-(D)-Chg-Pyr-NH—CH₂-5-(3-ham)-thioph by removal of the protecting group with 1 M hydrochloric acid at 60° whereby the product was precipitated from ether after concentration in vacuo.

FAB-MS (M+H⁺): 464

We claim:

1. Compounds of the formula I or II

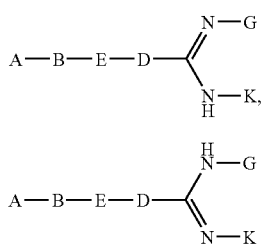

in which A, B, D, E, G and K have the following meanings:

A: $R^1OOC—CH_2—$, $R^1OOC—CH_2—CH_2—$, $R^1OOC—CH(CH_3)—$, $R^1OOC—C(CH_3)_2—$, $C_{1-4}$-alkyl-$SO_2$—$(CH_2)_{2-6}$, 5-tetrazyolyl-$(CH_2)_{1-6}$—, $C_{1-4}$-alkyl-O—$(CH_2)_{2-6}$—, $H_2N$—$(CH_2)_{2-3}$—, $CH_3$—NH—$(CH_2)_{2-3}$—, $(CH_3)_2N$—$(CH_2)_{2-3}$—, $H_2NSO_2$—$(CH_2)_{2-4}$—, $CH_3$—NHSO_2—$(CH_2)_{2-4}$—, in which $R^1$: is H—, $C_1$–$C_8$-alkyl-, $C_5$–$C_8$-cycloalkyl-, $C_5$–$C_8$-cycloalkyl-$C_1$–$C_3$-alkyl-, it being possible for all the radicals mentioned apart from H to carry optionally up to four identical or different radicals selected from $CH_3$, $CF_3$, F, Cl, or methoxy radicals, or $R^1$ is 2-oxo-1,3-dioxo-4-yl-methyl which may be substituted in the 5-position by $C_1$–$C_3$-alkyl or aryl, or $R^1$: is $R^{1b}$—C(O)O—CH_2—, $R^{1b}$—C(O)O—CH(CH_3)—, where $R^{1b}$ can be $C_1$–$C_4$-alkyl-, $C_5$–$C_8$-cycloalkyl-, $C_1$–$C_4$-alkyloxy- or $C_5$–$C_8$-cycloalkyloxy-,

B

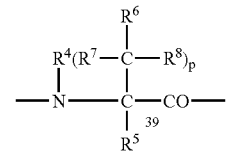

in which p is 0,1,
$R^4$ is H—,
$R^5$ is H—,
$R^6$ is cyclopentyl, cyclohexyl, cycloheptyl,
$R^7$ is H,
$R^8$ is H,

E

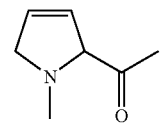

D

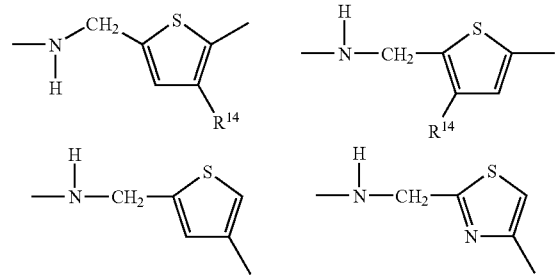

in which $R^{14}$: is H, $CH_3$, Cl,

G: is —OH, —C(O)OR²⁰, in which $R^{20}$ is —$C_{1-8}$-alkyl, —$C_1$–$C_3$-alkyl-$C_5$–$C_8$-cycloalkyl, —$C_5$–$C_8$-cycloalkyl, K is H, where the following applies, with retention of the meanings of D:

(i)
when E is II, and G is —OH, C(O)OR$^{20}$, where R$^{20}$ has the same meaning as above, and K is H, then A and B have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$—, C$_{1-4}$-alkyl-SO$_2$—(CH$_2$)$_{2-4}$—, 5-tetrazyolyl-(CH$_2$)$_{1-3}$—, C$_{1-4}$-alkyl-O—(CH$_2$)$_{2-4}$—, H$_2$N—(CH$_2$)$_{2-3}$, CH$_3$—NH—(CH$_2$)$_{2-3}$, (CH$_3$)$_2$N—(CH$_2$)$_{2-3}$, H$_2$N—SO$_2$—(CH$_2$)$_{2-4}$, CH$_3$—NH—SO$_2$—(CH$_2$)$_{2-4}$, in which R$^1$: is H—, C$_1$–C$_8$-alkyl-, C$_5$–C$_8$-cycloalkyl-, C$_5$–C$_8$-cycloalkyl-C$_1$–C$_3$-alkyl-, it being possible for all the radicals mentioned apart from H to carry optionally up to four identical or different radicals selected from CH$_3$, CF$_3$, F, Cl, or methoxy radicals, or R$^1$ is 2-oxo-1,3-dioxol-4-yl-methyl which may be substituted in position 5 by C$_1$–C$_{16}$-alkyl or aryl, or R$^1$: is R$^{1b}$—C(O)O—CH$_2$—, R$^{1b}$—C(O)O—CH(CH$_3$)—, where R$^{1b}$ can be C$_1$–C$_4$-alkyl, C$_5$–C$_8$-cycloalkyl, C$_1$–C$_4$-alkyloxy, C$_5$–C$_8$-cycloalkoxy,

B

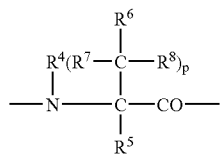

in which p: is 0, 1,

R$^4$: is H—,

R$^5$: H,

R$^6$: cyclopentyl, cyclohexyl, cycloheptyl,

R$^7$: H, and

R$^8$: H, (ii)
when E is VI, and G is OH and K is H, then A and B have the following meanings:

A: R$^1$OOC—CH$_2$, R$^1$OOC—CH$_2$—CH$_2$, R$^1$OOC—CH(CH$_3$), R$^1$OOC—C(CH$_3$)$_2$, in which R$^1$: is C$_7$–C$_8$-alkyl, C$_5$–C$_8$-cycloalkyl, C$_5$–C$_8$-cycloalkyl-C$_1$–C$_3$-alkyl, it being possible for all the radicals mentioned apart from H to carry optionally up to three identical or different radicals selected from CH$_3$, CF$_3$, F, Cl, or methoxy radicals, or 2-oxo-1,3-dioxol-4-yl-methyl- which may be substituted in position 5 by C$_1$–C$_{16}$-alkyl or aryl, or R$^1$: is R$^{1b}$—C(O)O—CH$_2$, R$^{1b}$—C(O)O—CH(CH$_3$)—, where R$^{1b}$ can be C$_1$–C$_4$-alkyl, C$_5$–C$_8$-cycloalkyl, C$_1$–C$_4$-alkyloxy, C$_5$–C$_8$-cycloalkoxy,

B

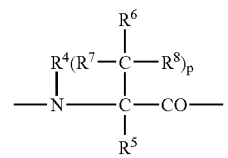

in which p: 0, 1,

R$^4$: is H—,

R$^5$: H,

R$^6$: cyclopentyl, cyclohexyl, cycloheptyl,

R$^7$: H, and

R$^8$: H, (iii)
when E is VI, and G is —C(O)OR$^{20}$, where R$^{20}$ has the same meaning as above, and K is H, then A and B have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$,— in which

R$^1$: is H—, C$_1$–C$_8$-alkyl-, C$_5$–C$_8$-cycloalkyl-, C$_5$–C$_8$-cycloalkyl-C$_1$–C$_3$-alkyl-, it being possible for all the radicals mentioned apart from H to carry optionally up to three identical or different radicals selected from CH$_3$, CF$_3$, F, Cl, or methoxy radicals, or R$^1$ is 2-oxo-1,3-dioxol-4-yl-methyl which may be substituted in position 5 by C$_1$–C$_{16}$-alkyl or aryl, or R$^1$ is R$^{1b}$—C(O)O—CH$_2$—, R$^{1b}$—C(O)O—CH(CH$_3$)—, where R$^{1b}$ can be C$_1$–C$_4$-alkyl, C$_5$–C$_8$-cycloalkyl, C$_1$–C$_4$-alkyloxy, C$_5$–C$_8$-cycloalkoxy,

B

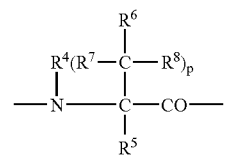

in which p: is 0, 1,

R$^4$: is H,

R$^5$: H,

R$^6$: cyclopentyl, cyclohexyl, cycloheptyl,

R$^7$H, and

R$^8$: H, and the physiologically tolerated salts thereof.

2. Compounds of the formula as claimed in claim 1, wherein A, B, D, E, G and K have the following meanings:

A: R$^1$OOC—CH$_2$—, R$^1$OOC—CH$_2$—CH$_2$—, R$^1$OOC—CH(CH$_3$)—, R$^1$OOC—C(CH$_3$)$_2$— in which

R$^1$: is C$_1$–C$_8$-alkyl-, C$_5$–C$_8$-cycloalkyl-, C$_5$–C$_8$-cycloalkyl-CH$_2$-alkyl-, it being possible for all the radicals mentioned to carry optionally up to four identical or different radicals selected from CH$_3$ or methoxy radicals,

B

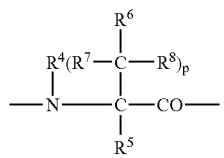

in which
p is 0, 1,
$R^4$ is H—,
$R^5$ is H—,
$R^6$ is cyclohexyl,
$R^7$ is H,
$R^8$ is H,

E

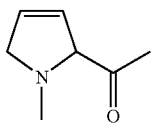     II

D

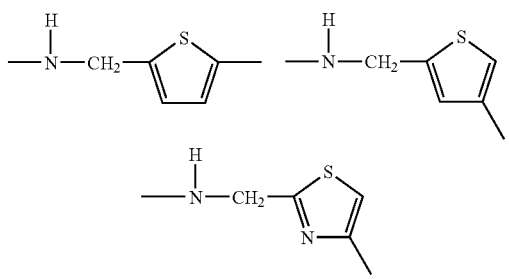

G is —OH,
K is H,
where the following applies, with retention of the meanings of D:
(i)
when E is II and G is —OH, then A and B have the following meanings:
A: $R^1OOC-CH_2-$, $R^1OOC-CH_2-CH_2-$, $R^1OOC-CH(CH_3)-$, $R^1OOC-C(CH_3)_2-$,
in which
$R^1$: is $C_1-C_8$-alkyl-, $C_5-C_8$-cycloalkyl-, $C_5-C_8$-cycloalkyl-$C_1$-alkyl-, it being possible for all the radicals mentioned apart from H to carry optionally up to four identical or different radicals selected from $CH_3$ or methoxy radicals,

B

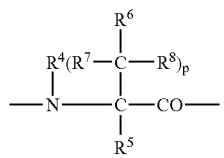

in which
p: is 0, 1,
$R^4$: is H—,
$R^5$: H,
$R^6$: cyclohexyl,
$R^7$: H, and
$R^8$: H,
(ii)
when E is VI, and G is OH and K is H, then A and B have the following meanings:
A: $R^1OOC-CH_2-$, $R^1OOC-CH_2-CH_2-$, $R^1OOC-CH(CH_3)-$, $R^1OOC-C(CH_3)_2-$,
in which
$R^1$: is $C_7-C_8$-alkyl, $C_5-C_8$-cycloalkyl, $C_5-C_8$-cycloalkyl-$C_1$-alkyl, it being possible for all the radicals mentioned apart from H to carry optionally up to three identical or different radicals selected $CH_3$ or methoxy radicals,

B

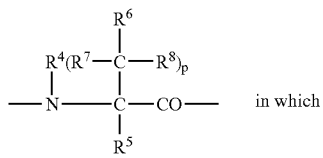    in which in which
p: 0, 1,
$R^4$: is H,
$R^5$: H,
$R^6$: cyclohexyl,
$R^7$: H, and
$R^8$: H and the physiologically tolerated salts thereof.

3. A pharmaceutical composition comprising compounds of the formula I as claimed in claim 1 in addition to conventional carriers and excipients.

4. A method of treating a disease selected from the groups consisting of deep vein thrombosis; pulmonary embolism, Alzheimer's disease; myocardial or cerebral infarction; atrial fibrillation and bypass occlusion that comprises administering an effective amount of a compound of claim 1 to a patient in need thereof.

* * * * *